United States Patent [19]

Toda et al.

[11] Patent Number: 5,047,847
[45] Date of Patent: Sep. 10, 1991

[54] ENDOSCOPE USING LIQUID CRYSTAL DEVICES DIFFERENT IN THE RESPONSE FREQUENCY IN THE IMAGE FORMING OPTICAL SYSTEM

[75] Inventors: Akitoshi Toda, Kunitachi; Hisanari Shimazu, Akishima; Akira Takano, Oume; Hirofumi Miyanaga, Hachioji; Susumu Takahashi, Kunitachi; Yoshinao Ohaki, Hachioji; Yoshisada Aoki, Hachioji, all of Japan

[73] Assignee: Olympus Optical Co., Ltd., Tokyo, Japan

[21] Appl. No.: 396,159

[22] Filed: Aug. 21, 1989

[30] Foreign Application Priority Data

Oct. 19, 1988 [JP] Japan .................. 63-263377

[51] Int. Cl.$^5$ .............. H04N 7/18; A61B 1/04
[52] U.S. Cl. ................... 358/98; 358/225; 359/53; 359/40; 359/92; 359/94
[58] Field of Search .......... 358/98, 211, 209, 225, 358/227, 228, 93; 340/784; 350/331 R, 346; 128/4, 6

[56] References Cited

U.S. PATENT DOCUMENTS

| | | | |
|---|---|---|---|
| 4,698,668 | 10/1987 | Milgram | 358/92 |
| 4,792,850 | 12/1988 | Lipton et al. | 358/92 |
| 4,831,452 | 5/1989 | Takanashi et al. | 358/225 X |
| 4,836,654 | 6/1989 | Fujimura et al. | 350/346 |
| 4,919,520 | 4/1990 | Okada et al. | 350/335 |

FOREIGN PATENT DOCUMENTS 60-54575 3/1985 Japan .

Primary Examiner—Victor R. Kostak
Attorney, Agent, or Firm—Armstrong, Nikaido, Marmelstein, Kubovcik & Murray

[57] ABSTRACT

At least a part of an image forming optical system is formed of a liquid crystal assembly consisting of a plurality of liquid crystals having a refractive index anisotropy and having different response frequencies of molecule orientation so that the transmittivity and refractive index of the plurality of liquid crystals may be independently controlled with few signal lines by varying the frequency of the driving signal applied to the liquid crystal assembly.

20 Claims, 33 Drawing Sheets

VIB. DIREC. OF POLAR

INPUT SIG. TO COMP.

OUTPUT OF COMP. 361

OUTPUT OF COMP. 362

OUTPUT OF EX-OR GATE 364

INVERTED SIG. OF EX-OR GATE

OUTPUT OF FF.

ENDOSCOPE USING LIQUID CRYSTAL DEVICES DIFFERENT IN THE RESPONSE FREQUENCY IN THE IMAGE FORMING OPTICAL SYSTEM

BACKGROUND OF THE INVENTION

1. Field of the Invention and Related Art Statement

This invention relates to an endoscope using, in the image forming optical system, a plurality of liquid crystals having different response frequencies of molecule orientation for a driving signal.

Recently, it is suggested to reduce mechanical moving parts by incorporating liquid crystal devices such as liquid crystal irises and liquid crystal lenses in an image forming optical system or the like for an endoscope.

In the case of incorporating a plurality of liquid crystal devices, there have been problems that it is uneconomical to provide a driving power source for each individual liquid crystal device and therefore a single power source is preferable but, on the other hand, it is necessary to separately control the individual liquid crystal devices and therefore the power source lines are so many as to be complicated.

Therefore, it has been considered to have a part of the power source lines common.

FIG. 1 shows an example wherein the reference numerals 1, 2 and 3 represent respectively a liquid crystal lens, liquid crystal iris and lens group arranged within the tip part of an endoscope (not illustrated) and forming an objective optical system and the reference symbols P, VR, SW1 and SW2 represent respectively a driving power source, variable resistance, liquid crystal lens switch and liquid crystal iris switch arranged in a hand base operating part (not illustrated). The liquid crystal lens 1 is connected with the resistance VR switch $SW_1$ and power source p through power source lines $l_1$ and $l_2$ and the liquid crystal iris 2 is connected with the switch SW2 and power source P through the power source lines $l_2$ and $l_3$. Thus, the power source line $l_2$ is used as a common line.

For the above mentioned formation, if the number of liquid crystal devices incorporated in the tip part of endoscope increases, the number of the common lines will also increase. This is very insufficient for an endoscope in which the insertable part, through which the power source lines are to be passed, and particularly insufficient for the flexible intermediate part since the parts are desired to be as small as possible in diameter.

OBJECTS AND SUMMARY OF THE INVENTION

An object of the present invention is to provide an endoscope wherein, even in case a plurality of liquid crystal devices are used, a small number of power source lines may be used and particularly the intermediate part of the insertable part can be made small in diameter.

Another object of the present invention is to provide an endoscope wherein, even in case the distance to an object to be imaged is varied, a clear endoscope image having no dulling will always be obtained.

According to the present invention, when at least a part of an image forming optical system is formed of a) a liquid crystal assembly consisting of a plurality of liquid crystals having a refractive index anisotropy and which have different response frequencies of molecule orientation depending on the frequency of a driving signal and b) a means of varying the frequency or the like of the driving signal applied to the liquid crystal assembly, the transmittivity and refractive index of the plurality of crystal liquids will be able to be independently controlled with a small number of signal lines.

BRIEF DESCRIPTION OF THE DRAWINGS

FIGS. 2 to 9 relate to the first embodiment of the present invention.

FIG. 2 is a formation view showing an entire endoscope apparatus of the first embodiment.

FIG. 3 is a formation view showing a scheme of a liquid crystal assembly and its driving system.

FIG. 4 is a formation view showing a liquid crystal assembly and its driving system.

FIG. 5 is an elevation of a liquid crystal iris.

FIG. 6 is a characteristic diagram showing dielectric characteristics against frequencies of liquid crystals used respectively for a liquid crystal lens and liquid crystal iris.

FIGS. 7 and 8 are characteristic diagrams showing refractive indices against applied voltages.

FIGS. 19 to 34 relate to an apparatus which can vary the illuminating range or visual field range.

FIG. 19 is a formation diagram of a fiber-scope provided with a parallax preventing function.

FIG. 20 is a formation diagram of a liquid crystal lens.

FIGS. 22 to 25 are formation diagrams respectively showing structures of the objective lens shown in FIG. 19.

FIG. 26 is a perspective view showing a Fresnel surfaced transparent plate.

FIG. 27 is an explanatory diagram showing the relation with an imaged field depth for focusing with two distances.

FIG. 28 is a explanatory diagram of varying the diaphragming amount as operatively connected with varying the focus.

FIGS. 29 to 32 are formation diagrams showing formation examples of illuminating lenses.

FIG. 34 is an elevation showing a light deflecting plate provided within an illuminating lens.

FIGS. 35 to 41 relate to apparatus for coping with the breaks or the like of driving signal transmitting lines.

FIG. 35 is a formation diagram of an endoscope apparatus of an embodiment of the same.

FIGS. 36 and 37 are formation diagrams of devices using liquid crystals.

FIG. 38 is a block diagram of a driving system for a device using liquid crystals.

FIG. 39 is a circuit diagram showing a formation of this driving system.

FIG. 41 is a formation diagram of an endoscope apparatus of another embodiment.

FIG. 43 is a formation diagram of an apparatus of another embodiment of the same.

FIG. 44 is an elevation of a liquid crystal iris.

FIG. 45 is a formation diagram of an apparatus of another embodiment.

FIG. 46 is a formation diagram of an essential part of a modification of the embodiment shown in FIG. 45.

FIG. 47 is a circuit diagram of an iris voltage producing circuit in FIG. 46.

FIG. 48 is a circuit diagram of an essential part of another modification of the embodiment in FIG. 45.

FIG. 49 is a formation diagram of an apparatus of another embodiment.

FIG. 50 is a formation diagram of an apparatus of another embodiment preventing the tone variation on the light source apparatus side.

FIG. 51 is a formation diagram of an endoscope apparatus provided with an iris using an electrochromic device.

FIG. 52 is an explanatory view showing the structure of an iris using an electrochromic device.

FIG. 53 is a formation view of a color imaging apparatus using liquid crystal devices.

FIG. 54 is a formation view of a liquid crystal device provided with iris and lens functions.

FIG. 55 is a formation diagram of a luminance adjusting circuit.

FIG. 56 is a general formation diagram of a fiberscope to which the color imaging apparatus in FIG. 53 is applied.

FIG. 57 is a characteristic diagram showing the transmittive characteristics of a correcting filter.

DETAILED DESCRIPTION OF THE PREFERRED EMBODIMENTS

Figure 2:
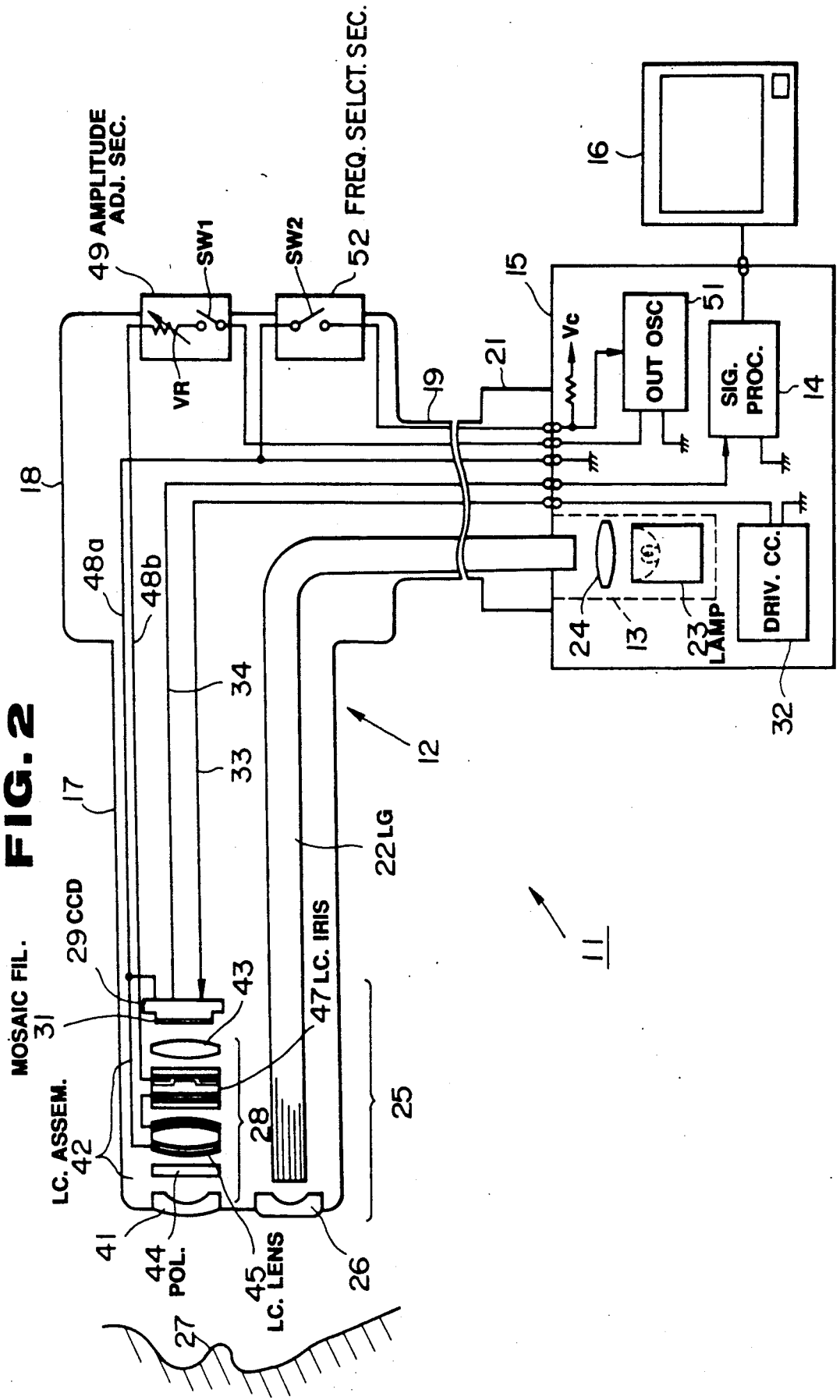

As shown in FIG. 2, an electronic endoscope apparatus 11 comprises an electronic scope 12, a video processor 15 having a built-in light source part 13 feeding an illuminating light to this electronic scope 12 and a signal processing circuit 14 for processing an image signal imaged by an imaging means of the electronic scope 12 and a color monitor 16 for color-displaying a standard video signal output from the signal processing circuit 14.

The above mentioned electronic scope 12 has a flexible elongate insertable part 17, a thick operating part 18 formed on the rear end side of this insertable part 17 and a universal cable 19 extended out of this operating part 18 and having a connector 21 fitted to the end so as to be removably connectable to the video processor 15.

A light guide 22 transmitting an illuminating light is inserted through the above mentioned insertable part 17 and is further inserted through the universal cable 19 so that, when the connector 21 is connected to the video processor 15, the illuminating light will be fed to one end surface of the light guide 22.

A white color light emitted from a lamp 23 is condensed by a condenser lens 24, is fed to one end surface of the light guide 22 opposed to the light path of this lens 24, is transmitted by this light guide 22 to the other end surface arranged in the tip part 25 of the insertable part 17 and is emitted to the object 27 side through an illuminating lens 26.

The object 27 illuminated by this emitted light is made to form an optical image on a solid state imaging device as, for example, a charge coupled device (abbreviated as CCD hereinafter) arranged in the image forming position by an objective optical system 28 arranged in the tip part 25.

A mosaic color filter 31 is fitted to the imaging surface of this CCD to color-separate the respective pixels of the CCD 29. A driving signal from a CCD driving circuit 32 built-in in the video processor 15 is applied to this CCD 29 through a plurality of signal lines (one is shown in FIG. 2). By the application of this driving signal, an image signal photoelectrically converted the CCD 29 and accumulated as an electric charge corresponding to the object image is read out and is input into the signal processing circuit within the video processor 15 through the signal lines 34.

The image signal is converted by this signal processing circuit 14 to a standard video signal as, for example, an NTSC composite video signal which is color-displayed on the color monitor 16.

The objective optical system 28 arranged in the tip part 25 of the insertable part 17 is formed, for example, of a first optical lens 41, a liquid crystal device assembly (abbreviated as the LC assembly hereinafter) 42 and a second optical lens 43.

The above mentioned LC assembly 42 is formed of a liquid crystal lens 45 provided with a polarizing plate 44 on the entrance side and a liquid crystal iris 47 provided with polarizing plates 46 and 46' arranged on both sides.

The above mentioned LC assembly 42 are 48b. The driving line 48a which is one of the driving lines 48a and 48b is a ground line used in common with the ground line of the CCD 29. The other driving line 48b can be connected to a sinusoidal wave oscillator 51 as, for example, a Wien bridge type oscillator through a variable resistance VR and switch SW1 of an amplitude (voltage) adjusting section 49 provided, for example, in the operating part 18.

The above mentioned operating part 18 is also provided with a switch SW2 forming an (oscillation) frequency selecting section 52 so that, when this switch SW2 is switched on, a frequency switching signal changing "H" to "L" will be transmitted to the oscillator 51 and the resistances R1 and R2 and capacitors C1 and C2 of the oscillator 51 will be switched through analogue switches AS1 and AS2 (See FIG. 4) to switch the oscillation frequency. Therefore, when this switch SW2 is switched on/off, driving signals of different frequencies will be output from the oscillator 51.

Figure 1:
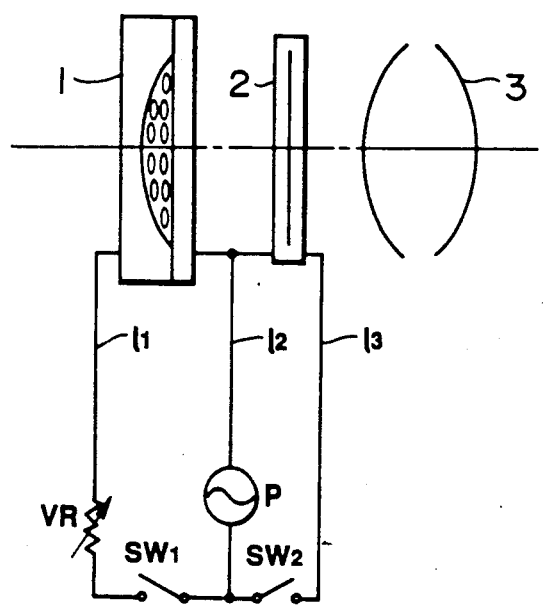
FIG. 1 is a view showing an objective optical system formed of liquid crystal devices in a prior example.
Figure 3:
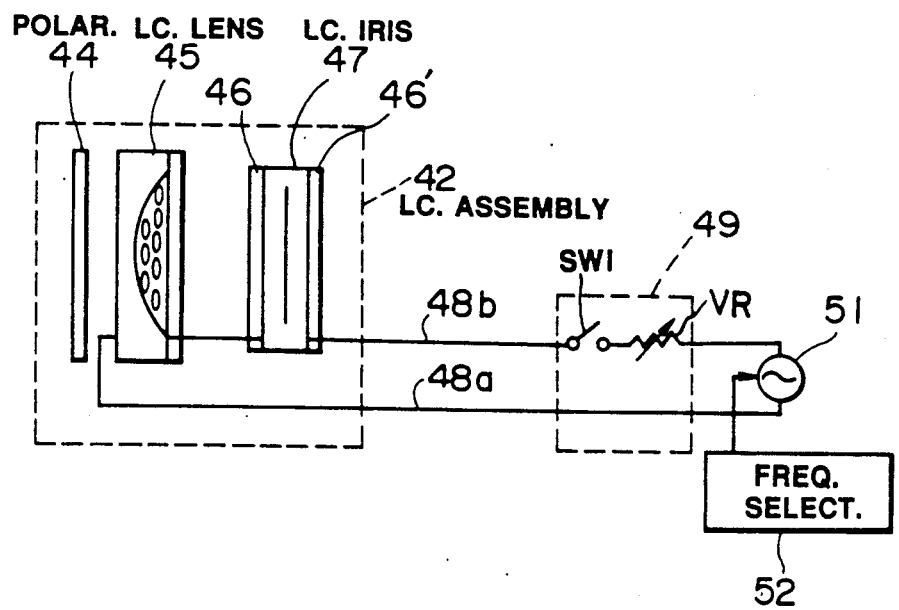
Figure 4:
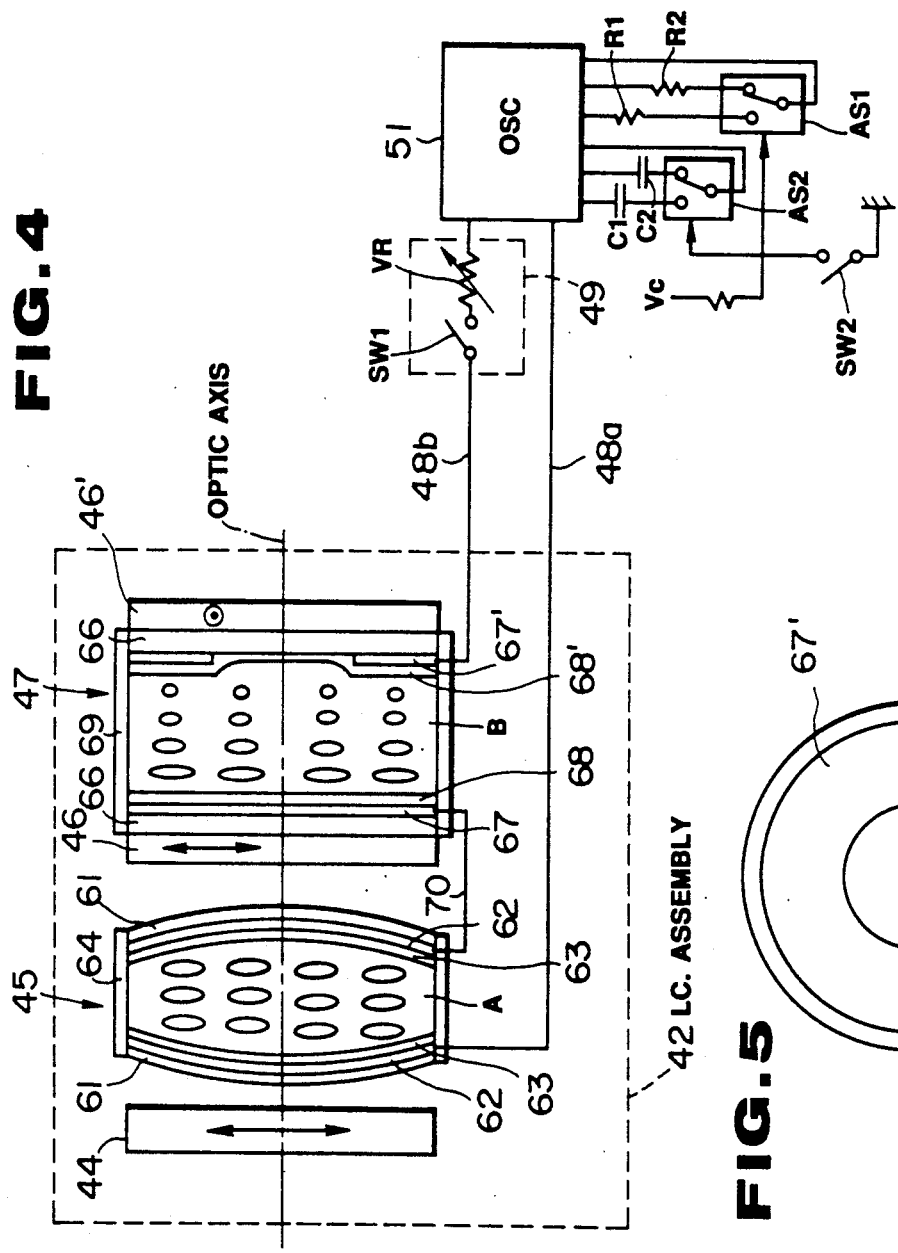

The schematic formations of the above mentioned LC assembly 42 and its driving system (control system) are shown in FIG. 3 and the more detailed formations of them are shown in FIG. 4.

As shown in FIG. 4, in the liquid crystal lens 45, transparent plates 61 such as spherical glass plates or acryl plates are arranged as opposed to each other. A transparent electrode 62 is fitted to the inside surface of each transparent plate 61. An orienting membrane 63 is formed on the inside surface of each transparent electrode 62. A convex lens-like hollow chamber (cell) is formed between the opposed orienting membranes 63. Both transparent plates 61 are fixed to an annulus 64 and and a nematic liquid crystal A is enclosed within this cell.

In the above mentioned liquid crystal A, by the orienting membranes 63, when no driving voltage is applied, the arrangement of the liquid crystal molecules will be a homogeneous arrangement in which the molecules have the major axes in the direction parallel with the planes of the orienting membranes 63 and are arranged in the polarizing direction of the polarizing plate 44, that is, in one direction as shown in FIG. 4.

Also, the liquid crystal iris 47 as the other liquid crystal device has a nematic liquid crystal B in a twisted nematic (abbreviated as TN) arrangement within the cell.

As shown in FIG. 4, transparent electrodes 67 and 67' and orienting membranes 68 and 68' are laminated respectively on the inside surfaces of two parallelly arranged transparent plates 66 which are secured at least on the peripheral edges to an annulus 69 by a bonding agent or the like to form a cell in which the nematic liquid crystal B is enclosed in the TN arrangement.

The two orienting membranes 68 and 68' are arranged as opposed to each other so that the direction of orienting the liquid crystal molecules may be different by 90 degrees, that is, may be twisted by 90 degrees. Therefore, in the enclosed nematic liquid crystal B, the liquid crystal molecules near the respective orienting membranes 68 and 68' will be directed in the orienting direction of the respective orienting membranes 68 and 68' but the liquid crystal molecules away from these orienting membranes 68 and 68' will be in a little twisted orienting direction and the arrangement of the liquid crystal as a whole will be a TN arrangement.

Figure 5:
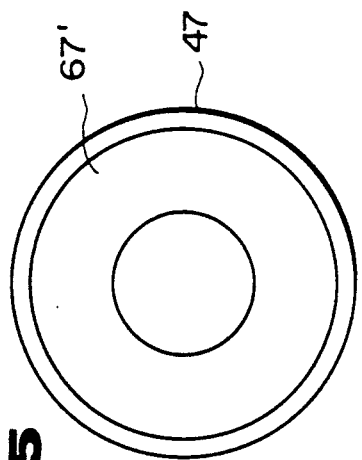

Also, in this liquid crystal iris 47, so as to have an iris function, as shown in FIG. 5, one electrode 67' is formed to be like a ring in which no electrode part is formed in the central part.

On both sides of the above mentioned transparent plates 66, two polarizing plates 46 and 46' in which the polarizing directions intersect at right angles with each other are arranged to have an iris function. The polarizing plate 46 on the liquid crystal lens 45 side is so arranged that its polarizing direction may coincide with that of the polarizing plate 44.

The electrode 62 of one of the above mentioned liquid crystal lenses 45 and the electrode 67' of one of the liquid crystal irises 47 are connected with each other through a lead wire 70 and the respective electrodes 62 and 67' of the others are output to the oscillator 51 side outside the LC assembly 42 through the signal lines 48a and 48b. That is, in this embodiment, the two liquid crystal lenses 45 and liquid crystal irises 47 are connected in series and are driven by a driving signal from the driving system through the two signal lines 48a and 48b.

The above mentioned liquid crystals A and B generally have a refractive index anisotropy the same as an optical uniaxial crystal and therefore show a double refractivity based on this refractive index anisotropy.

That is, as the refractive index n·in the case that the oscillating direction of the electric vector of the light intersects at right angles with the major axis of the liquid crystal molecule and the refractive index n∥ in the case that they are parallel are different from each other, a double refractivity is shown. In this case, the refractive index n⊥ corresponds to a refractive index $n_o$ for ordinary light and the refractive index n∥ to a refractive index $n_o$ for an abnormal light.

The refractive index anisotropy Δn, representing the size of this double refractivity, is defined by $$\Delta n = n\| - n\perp$$

and this Δn is normally positive for a nematic liquid crystal. That is $$\Delta n > 0 \ (or \ n\| > n\perp).$$

Even in this embodiment, in the refractive indices $n_A\|$, $n_a\perp$; $n_B\perp$ of the liquid crystals A and B corresponding to the above mentioned refractive indices n∥ and n⊥, the respective refractive index anisotropies $\Delta n_A$ and $\Delta n_B$ are positive.

In this embodiment, a nematic liquid crystal of different characteristics in response frequencies relating to the molecule orientation of the liquid crystals A and B for a driving signal is used so that the two liquid crystal lenses 45 and liquid crystal irises 47 may be substantially independently controlled by a common driving signal.

Figure 6:
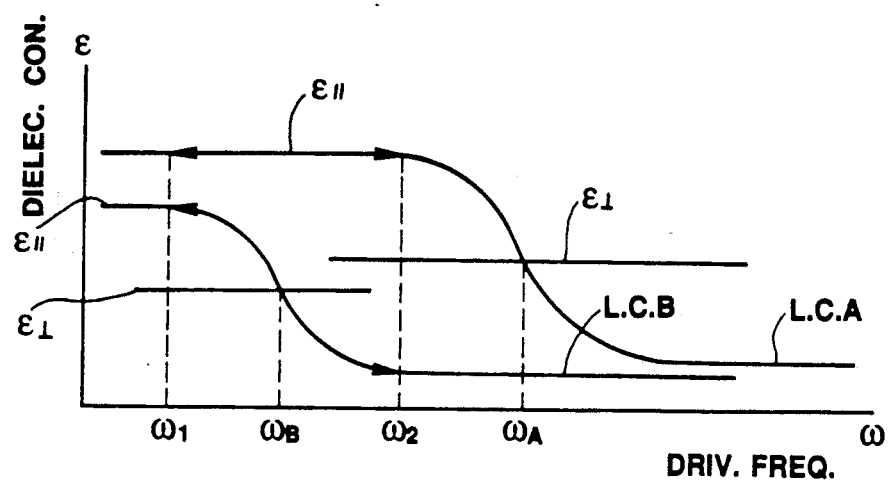

That is, as shown in FIG. 6, the liquid crystal of characteristics having the frequency responses of the dielectric constants and $\epsilon_B\perp$ of the liquid crystal B used in the liquid crystal iris 47 are lower than the frequency characteristics of the dielectric constants $\epsilon_A\|$ and $\epsilon_A\perp$ corresponding to the refractive indices $n_A\|$ and $n_A\perp$ of the liquid crystal A. In this case, it is important that the response frequencies relating to the dielectric constants $\epsilon_A\|$ and $\epsilon_B\|$ are different from each other.

That is, when a common driving signal is applied to the liquid crystals A and B (whose voltage values may be equal) and their frequencies are elevated (to be high), the liquid crystal B of the TN arrangement will be able to follow the driving signal (electric field) of a low frequency in this arrangement but will gradually become unable to follow it and will therefore reduced in the dielectric constant $\epsilon_B\|$ when the frequency becomes higher than $\omega_1$ and will not follow the signal at all when the frequency is above $\omega_2$.

At a frequency $\omega_B$ between the frequencies $\omega_1$ and $\omega_2$, the dielectric constant will be equal to the dielectric constant $\epsilon_B\perp$ when the major axes of the liquid crystal molecules are arranged in the electric field direction, that is, in a homeotropic arrangement.

In case this liquid crystal B is in the homeotropic arrangement, the frequency response of the liquid crystal molecule will not vary very much.

On the other hand, the other liquid crystal A is formed of a liquid crystal of a characteristic that the dielectric constant $\epsilon_A\|$ in the homogeneous arrangement and the dielectric constant $\epsilon_A\perp$ in the homeotropic arrangement will not substantially vary at a frequency below at least the above mentioned frequency $\omega_2$. That is, the liquid crystal A uses a liquid crystal of a dielectric characteristic that, in either of these two arrangements, until at least the frequency $\omega_2$, the liquid crystal molecule can follow the driving signal.

At a frequency higher than above mentioned frequency $\omega_2$, as shown in FIG. 6, even in this liquid crystal A, the dielectric constant $\epsilon_A \|$ will generally become smaller, for example, at a frequency $\omega_A$, the dielectric constants $\epsilon_A \|$ and $\epsilon_A \perp$ will be of equal values and, at a frequency higher than this, $\epsilon_A \| < \epsilon_A \perp$.

Generally, in response to the arrangement of the liquid crystal molecules, the liquid crystal will show a dielectric anisotropy which is not isotropic but is substantially uniaxial. This first embodiment is characterized by selectively using a nematic liquid crystal of a combination in which, of the two liquid crystals A and B, the dielectric constant $\epsilon_B \|$ of one of the liquid crystals B used for the liquid crystal irises 47 shows a frequency response lower than of the dielectric constant $\epsilon_A \|$ of one of the liquid crystals A used for the liquid crystal lenses 45.

On the other hand, the oscillator 51 forming the driving system of the LC assembly 42 using these liquid crystals A and B is made to have an oscillating frequency selectable by the frequency selecting section 52. It is so set that, for example, when the switch SW2 is off, the oscillating frequency will be $\omega_1$ and, when the switch is on, the resistance and capacitor of the oscillator 51 will be switched respectively from $R_1$ to $R_2$ and from $C_1$ to $C_2$ and the oscillating frequency will be $\omega_s$.

The oscillating output of the above mentioned oscillator 51 can be controlled by the amplitude adjusting section 49. That is, when the SW1 is off, the output will be zero and, when the switch is on, the value of the variable resistance VR will be varied and the output level (amplitude) will be varied.

The dielectric constants $\epsilon \|$ and $\epsilon \perp$ (including the liquid crystals A and B) are in the relation of the refractive indices n $\|$ and n$\perp$ with $\sqrt{\epsilon \|} = n \|$ and $\sqrt{\epsilon \perp} = n \perp$.

These relative formulae will be established inherently when the frequency for measuring the dielectric constants $\epsilon \|$ and $\epsilon \perp$ is high enough. However, in this specification, for the sake of simplification, the above described relative formulae shall be used.

The function of the LC assembly 42 in the apparatus 11 of this first embodiment shall be explained in the following.

First of all, when the switch SW1 is off, no driving signal will be applied to the two liquid crystals A and B, therefore the molecule arrangement of the liquid crystal A will be a homogeneous arrangement in which the major axes of the molecules are arranged in the polarizing direction of the polarizing plate 44 and the liquid crystal A will be a medium of a refractive index $n_A \|$ of a molecule arrangement parallel with the electric field vector direction of the incident light transmitted through the polarizing plate 44 and will therefore act as a lens medium of a refractive index larger than the refractive index $n_a \perp$ for the homeotropic arrangement and as a lens of a short focal distance.

In the liquid crystal iris 47, when the switch SW1 is off, the liquid crystal molecules will be in a TN arrangement and, when the linear polarized light incident into the (TN liquid crystal) cell through the polarizing plate 46 passes through this cell, the polarizing surface will be rotated by 90 degrees by the liquid crystal B of the TN arrangement, the linear polarized light will become light in the polarizing direction of the polarizing plate 46' and will pass through this polarizing plate 46'. That is, the liquid crystal iris 47 will pass the light independently of the electrode 67' and will be therefore fully opened.

In this state, the CCD 29 is arranged with respect to the objective optical system 28 in a position in which an object image of an object at a considerably near distance is formed clearly (without being dulled).

Therefore, for example, when the distance to the object becomes large, a defocused dulled image will be formed on the CCD 29.

In such a case, if the switch SW1 is switched on to reduce the resistance value of the variable resistance VR, the output level of the driving signal of the oscillator 51 will become high. When this output level exceeds a threshold value $V_{th}$ corresponding to the liquid crystal A, the molecule arrangement of the liquid crystal A will gradually shift from the homogeneous arrangement to a homeotropic arrangement and, when it becomes higher than a fixed level $V_{max}$, the molecule arrangement of the liquid crystal A will substantially become a homeotropic arrangement in which the major axis direction of the liquid crystal molecules intersects at right angles with the polarizing plate 44 (in other words, coincides with the electric field direction of the driving signal).

The refractive index in this homeotropic arrangement will be $n_a \perp$. That is, the refractive index of the crystal A for the incident light will become smaller and therefore the focal distance of the liquid crystal lens 45 will become longer.

Figure 7:
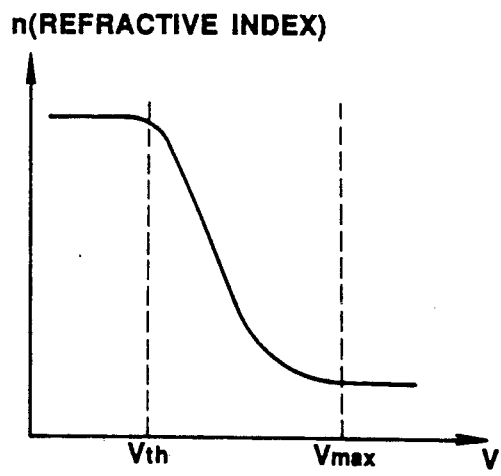

The manner in which the refractive index of the liquid crystal lens 45 varies in response to the applied voltage (driving signal level) is shown in FIG. 7. As shown in FIG. 7, by varying the size of the applied voltage, the refractive index n of the liquid crystal lens 45 can be freely controlled.

When the focal distance of the above mentioned liquid crystal lens 45 is made longer, the focal distance of the entire objective lens system will become longer so that, even for a far object, the position of the CCD 29 may be set as focused.

In this case, in order to keep the liquid crystal iris 45 opened, the switch SW2 will be switched on to make the frequency of the oscillator 51 $\omega_2$.

Even if the frequency of the oscillator 51 is selected to be either $\omega_1$ or $\omega_2$, the liquid crystal A will act as described above. On the other hand, in the liquid crystal B forming the liquid crystal iris 45, when the frequency becomes $\omega_2$, the liquid crystal molecules in the TN arrangement will not be able to follow the electric field of this frequency and will remain in the TN arrangement.

Figure 8:
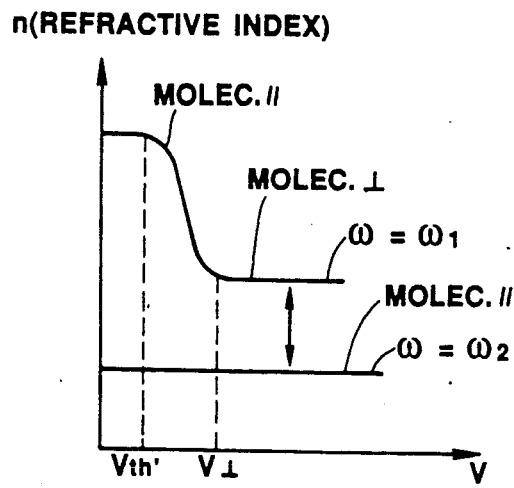

The refractive index in this case is shown in FIG. 8. As shown in FIG. 8, at the frequency of $\omega_2$, a fixed refractive index will be made. Thus, with the iris fully opened, the focal distance of the liquid crystal lens 45 can be freely varied.

On the other hand, for example, while a far object is being observed as focused, in case the fully opened iris is throttled t observe the depth of field deeply (a wide range clearly), the switch SW2 may be only switched off. When it is switched off, the frequency of the oscillator 51 will become $\omega_1$ and therefore the liquid crystal B will be able to follow the driving signal.

Therefore, in response to the level of the driving signal, the molecule orientation of the liquid crystal B will vary as shown by the refractive index in FIG. 8.

That is, when the level of the driving signal exceeds the threshold value $V_{th}$, the arrangement of the liquid crystal molecules will change from the TN arrangement (molecule ∥) to a homeotropic arrangement (molecule ⊥) and the refractive index n will also change from $n_B\|$ to $n_B\perp$. Therefore, if held above the level $V\perp$ on which a hommeotropic arrangement will be made, the liquid crystal B in the part opposed to the ring-like electrode 67' will be able to be made in a homeotropic arrangement. As the liquid crystal B in this homeotropic arrangement has no optical rotation, the polarizing plate 46' will not be able to be penetrated. Therefore, the liquid crystal part opposed to the ring-like electrode 67' will act as a light intercepting section.

Further, in a near distance state, in case it is desired to throttle the iris as in a too bright case, in the state of the frequency $\omega_1$, the level of the driving signal may be made above $V\perp$ by the variable resistance $V_R$.

As described above, in the case of making the iris function act on the liquid crystal lens 47, the frequency must be (below) $\omega_1$ and the output level of the driving signal must be above $V\perp$. This output level acts also on the liquid crystal A (which is not always on the same level). However, if the voltage level $V\perp$ varying the liquid crystal B from the TN arrangement to a homeotropic arrangement is made to be below the threshold value $V_{th}$ of the liquid crystal A, the liquid crystal A will be able to be prevented from being substantially influenced.

For example, in case the liquid crystal lens 45 is held in the shortest focal distance state and the liquid crystal iris 47 is throttled, in order to throttle at least this liquid crystal iris 47, the output level of the driving signal must be set so that the level to the liquid crystal iris 47 may be $V\perp$. However, in case this output level is applied to the liquid crystal lens 45, if it is below the threshold value $V_{th}$ at which the refractive index begins to vary, the focal distance of the liquid crystal lens 45 will not vary. If this condition is met, in the case of other focal distances, no problem will be produced.

Even in the case of a threshold value at which, for example, the liquid crystals B will not substantially vary per unit thickness, if the thickness (distance between both electrodes 67 and 67') is made smaller than on the liquid crystal lens 45 side, this condition will be able to be realized.

Therefore, in the above described explanation, for the sake of simplification, it is described that, in the case of making the focal distance shortest and keeping the iris opened, the switch SW1 may be switched off. However, as shown in FIG. 9a, even in case the resistance R1 is connected in parallel with the variable resistance VR and switch SW1 and the switch SW1 is off, a voltage of $V\perp$ may be applied to the liquid crystal iris 47 through this resistance R1.

Thus, in case the focal distance of the liquid crystal lens 45 is to be made longer, the switch SW1 may be switched on to vary the variable resistance VR and, in order to set the focal distance to be shortest, the switch SW1 may be off.

On the other hand, in case the liquid crystal iris 47 is to be opened, the switch SW2 may be on and, in case it is to be throttled, the switch SW2 may be off.

Figure 9A:
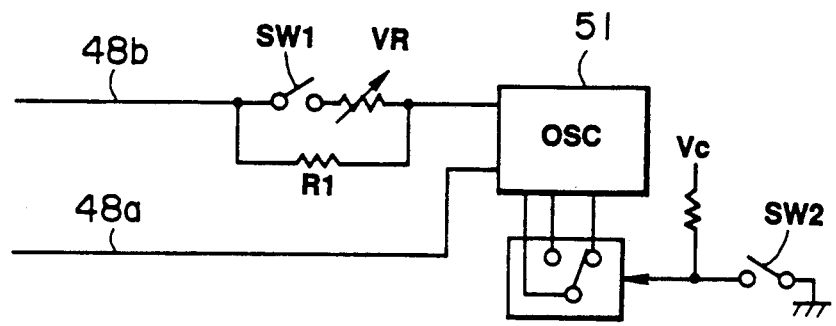
FIGS. 9A-9C are circuit diagrams showing a modification of a control system of a liquid crystal assembly.
Figure 9B:
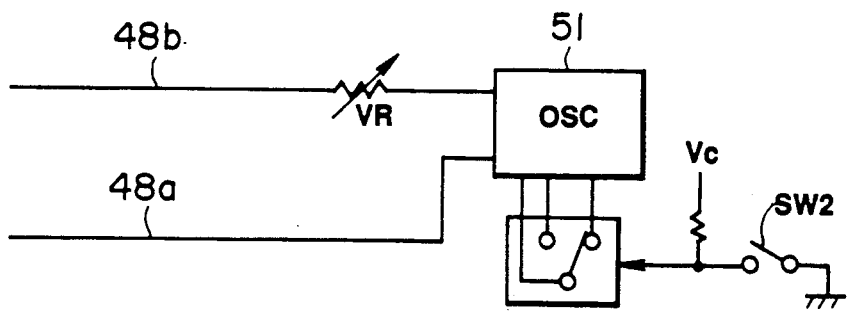

As shown in FIG. 9b which is a modification of FIG. 9a, the switch SW1 may be omitted. In this formation, the focal distance of the liquid crystal lens 45 can be varied by the variable resistance VR. On the other hand, the throttling of the liquid crystal iris 47 can be controlled by switching the switch SW2 on/off.

Thus, as the liquid crystal lens 45 and liquid crystal iris 47 can be controlled substantially independently by two driving lines 48a and 48b, the outside diameter of the insertable part 17 can be made small. Therefore, for example, in the case of a medical endoscope, the pain of the patient will be able to be reduced. Also, in the industrial field, as the insertable part can be made thin, it can be inserted in a small pipe or the like.

Figure 9C:
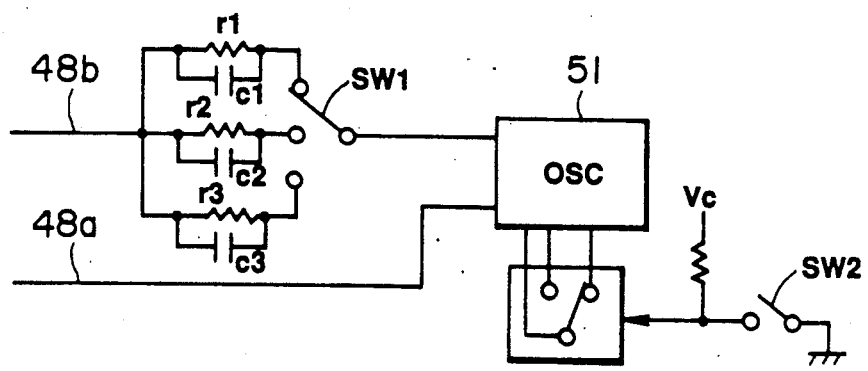

As the liquid crystal device has a property of a capacitor as an electric circuit device, if the dielectric constant $\epsilon$ varies, the capacitance will vary. Therefore, as in this embodiment, in the case of a series type, the voltage dividing ratio will vary and, in case the liquid crystal devices are respectively independently operated, the characteristics will be likely to somewhat vary. Particularly, in case the influence on the liquid crystal lens 45 whose characteristics continuously vary is large, instead of continuously varying the applied voltage with the variable resistance VR, as shown in FIG. 9c, a plurality of resistances r1, r2 and r3 may be varied step by step with a switch SW1 and the variation of the voltage dividing ratio may be compensated by capacitors c1, c2 and c3.

Even if merely the resistances r1, r2 and r3 are varied step by step, there may be no substantial trouble in some cases.

Figure 10:
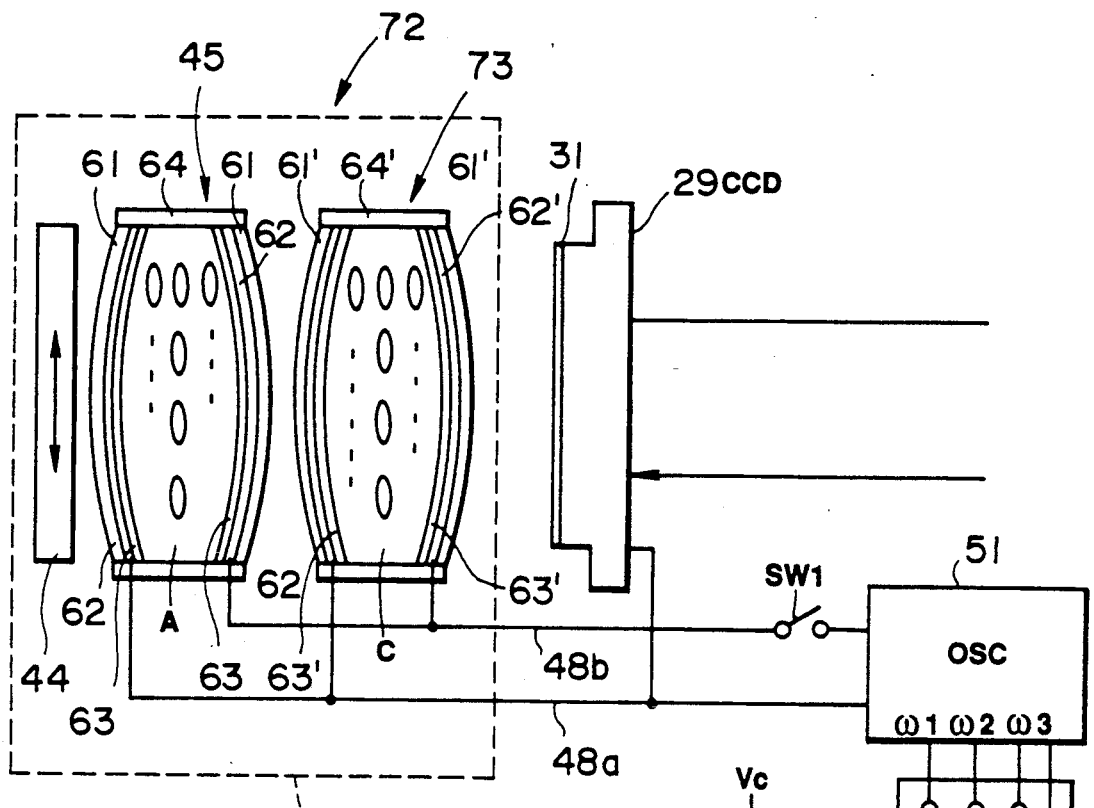
FIG. 10 is a formation diagram showing a liquid crystal assembly and its driving system in the second embodiment of the present invention.

FIG. 10 shows a liquid crystal assembly 71 in the second embodiment of the present invention. In this embodiment, an objective optical system 72 is formed of a liquid crystal assembly 61 formed of two liquid crystal lenses 45 and 73.

The above mentioned liquid crystal lens 73 is of the same structure as of the other liquid crystal lens 45 except that a TN liquid crystal C of a response frequency different from that of the liquid crystal A is used. Therefore, the same members are shown by attaching "'".

Also, in this embodiment, both liquid crystal lenses 45 and 73 have respective electrodes 62 and 62' connected in parallel respectively with driving lines 48a and 48b. which are connected with an oscillator 51 through a switch SW1.

Figure 11:
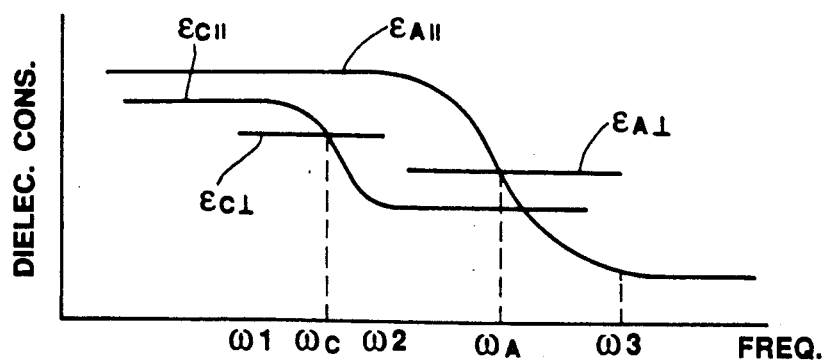
FIG. 11 is a characteristic diagram showing dielectric characteristics against the frequencies of liquid crystals used in the second embodiment.

The response characteristics of the molecule orientation against the frequency of the liquid crystals A and B of the liquid crystal lenses 45 and 73 are shown in FIG. 11. The liquid crystal C is lower than the liquid crystal A, for example, in the response frequency $\omega_c$. The oscillator 51 is set to selectively oscillate, three frequencies $\omega_1$, $\omega_2$ and $\omega_3$ by a switch 75 in response to the response characteristics of these liquid crystals A and C.

The output level of the oscillator 51 is made to be above the threshold value required to change the orientation of the molecules of the respective liquid crystals of both liquid crystal lenses 45 and 73.

In case the switch SW1 is off, both liquid crystal lenses 45 and 73 will remain in the homogeneous arrangement and will show the refractive index in this arrangement (in the case of the characteristics in FIG. 11, the refractive index will be largest).

While the switch SW1 is on, if the frequency is selected, both liquid crystal lenses 45 and 73 will be in a homeotropic arrangement and the refractive index in this arrangement will be shown. At the frequency, the liquid crystal lens 45 will show the refractive index in the homeotropic arrangement but the liquid crystal lens 73 will not be able to respond to this frequency $\omega_2$ and will therefore show the refractive index in the homogeneous arrangement. If the frequency $\omega_3$ is selected, both liquid crystal lenses 45 and 73 will not be able to respond to this frequency $\omega_3$ and will therefore show the refractive index in the homogeneous arrangement. Thus, even by only varying the frequency of the oscillator 51, the molecule orientation of the two liquid crystal lenses 45 and 73 can be controlled respectively substantially independently and by controlling the refractive index based on the molecule arrangement, the focal distance can be varied.

Also, in this embodiment, as the driving signal is applied in parallel, in case the frequency is varied, even if the impedance of the respective liquid crystal lenses 45 and 73 is varied, a driving signal of the same level will be able to be applied.

Figure 12:
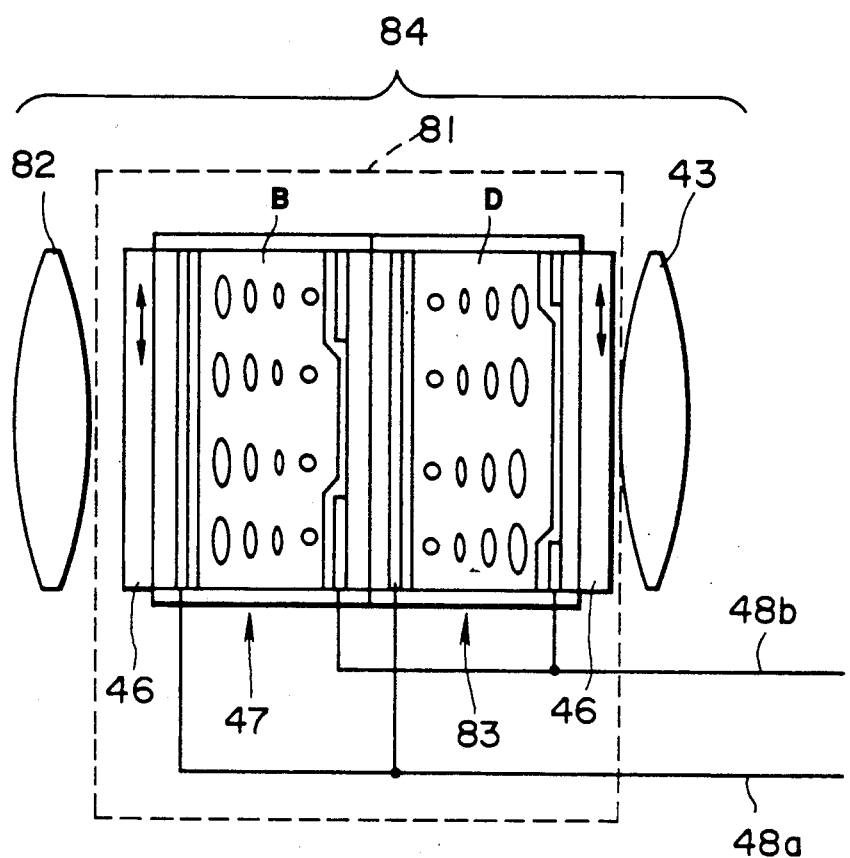
FIG. 12 is a formation diagram showing a liquid crystal assembly in the third embodiment of the present invention.

FIG. 12 shows a liquid crystal assembly 81 in the third embodiment of the present invention.

In this embodiment, a liquid crystal assembly 81 formed of two liquid crystal irises 47 and 83 i arranged between optical lenses 82 and 43 to form an objective optical system 84.

The above mentioned liquid crystal iris 83 uses a liquid crystal D different in the response frequency from a liquid crystal B of the other liquid crystal iris 47 and uses an electrode 67″ having an aperture (large in this case) different from an aperture of the electrode 67′. Also, the liquid crystal iris 83 changes further by 90 degrees the optical rotation direction of the light whose optical rotation direction has been changed by 90 degrees by the other liquid crystal iris 47 (in case the driving signal is not applied). Therefore, both liquid crystal irises 47 and 83 are held between polarizing plates 46 arranged to transmit linear polarizations in the same direction.

Figure 13:
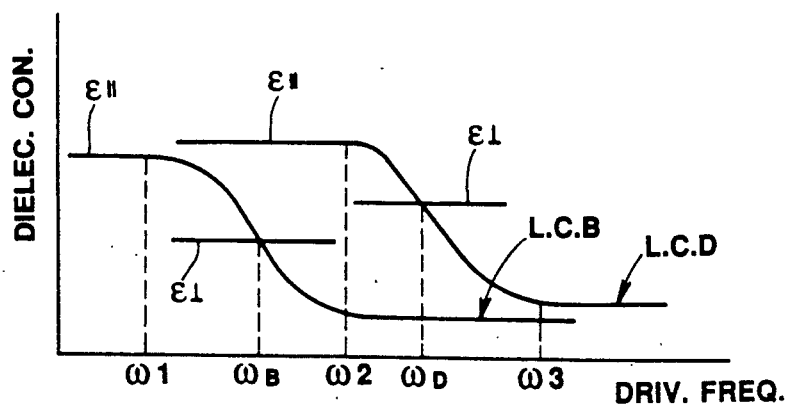
FIG. 13 is a characteristic diagram showing dielectric characteristics against the frequencies of liquid crystals in the third embodiment.

The response frequency $\omega_D$ of the molecule orientation of the liquid crystal D used in the above mentioned liquid crystal iris 83 is higher than the response frequency $\omega_B$ of the liquid crystal B as shown, for example, in FIG. 13.

Therefore, in response to these response frequencies $\omega_B$ and $\omega_D$, the oscillator can selectively output driving signals of frequencies $\omega_1$, $\omega_2$ and $\omega_3$ set as shown in FIG. 13. In this case, the driving system shown in FIG. 10 can be used. For example, in order to open the iris, the switch SW1 may be switched off or the switch SW1 may be switched on and the frequency may be made $\omega_3$.

In order to slightly throttle the opened iris, when the switch SW1 is switched on and the frequency $\omega_2$ is selected, the liquid crystal molecules in the part opposed to the electrode 67″ of the liquid crystal iris 83 will be in the homeotropic arrangement and the area part opposed to this electrode 67″ will intercept the light.

When throttling the iris, when the frequency $\omega_1$ is selected, the liquid crystal molecules in the part opposed to the electrode 67′ of the liquid crystal iris 47 will be in the homeotropic arrangement as described above and will perform the function of intercepting light.

Figure 14:
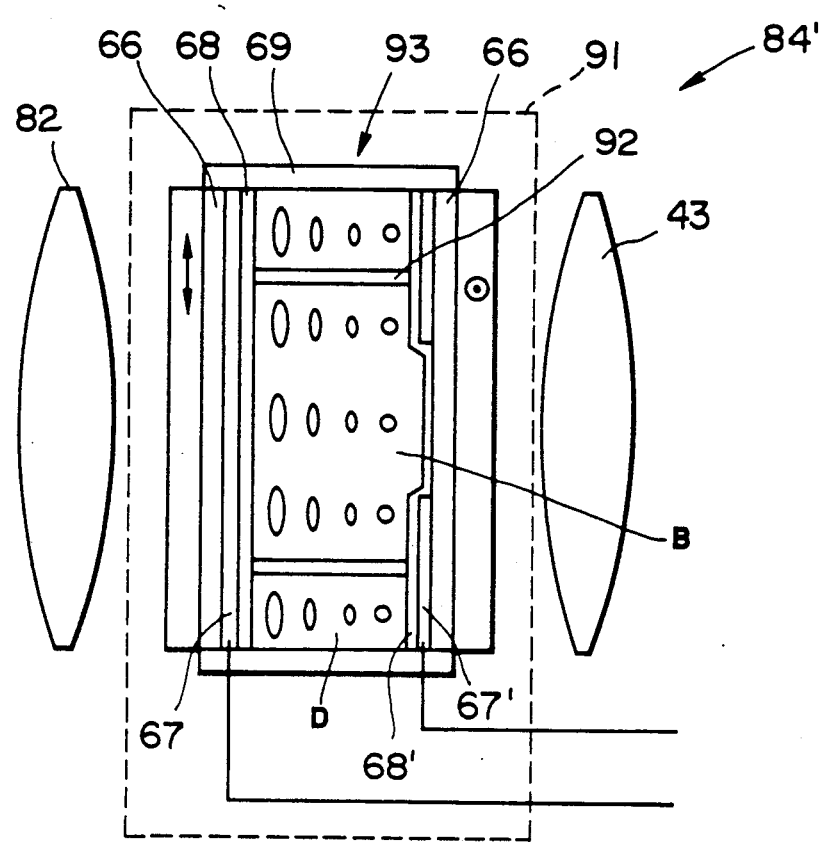
FIG. 14 is a formation diagram showing a liquid crystal assembly of a modification of the third embodiment.

FIG. 14 shows a modification of the third embodiment. This liquid crystal assembly 91 is formed of a liquid crystal iris 93 wherein, in the liquid crystal iris 47 shown, for example, in FIG. 4, a ring-like partition member 92 of a diameter larger than of the aperture of the electrode 67′ is provided, the liquid crystal D is put in a ring-like space outside this partition member 92 and the liquid crystal B is put in a space inside this partition member 92.

Figure 15:
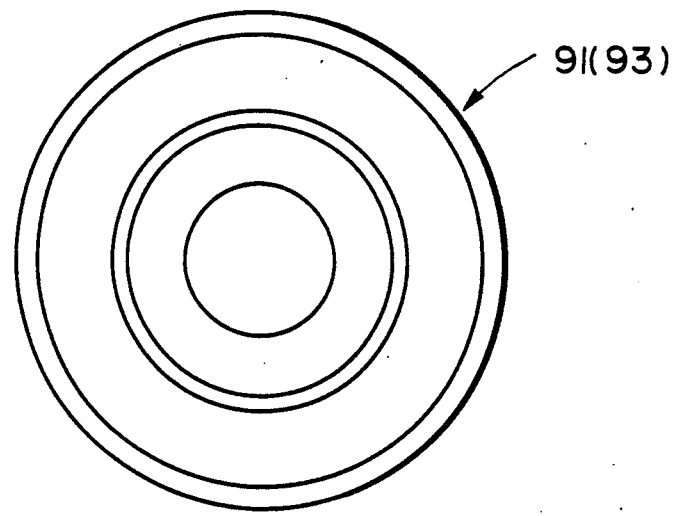
FIG. 15 is an elevation of a liquid crystal iris.

This liquid crystal assembly 91 is as in FIG. 15 as seen from the front surface.

For example, if a driving signal of the frequency $\omega_2$ is applied, the molecule arrangement of the liquid crystal D will be a homeotropic arrangement and this liquid crystal D part will intercept the light.

If a driving signal of the frequency $\omega_1$ is applied, the molecule arrangement of the liquid crystal D and the liquid crystal B in the part opposed to the electrode 67′ will be a homeotropic arrangement and will intercept the light. That is, this modification has the same function as the third embodiment. The objective optical system 84′ of this embodiment can be made smaller than the third embodiment.

In FIG. 14, two liquid crystals B and D are used. However, it is apparent that the liquid crystal may be formed of liquid crystals of further different response frequencies.

Figure 16:
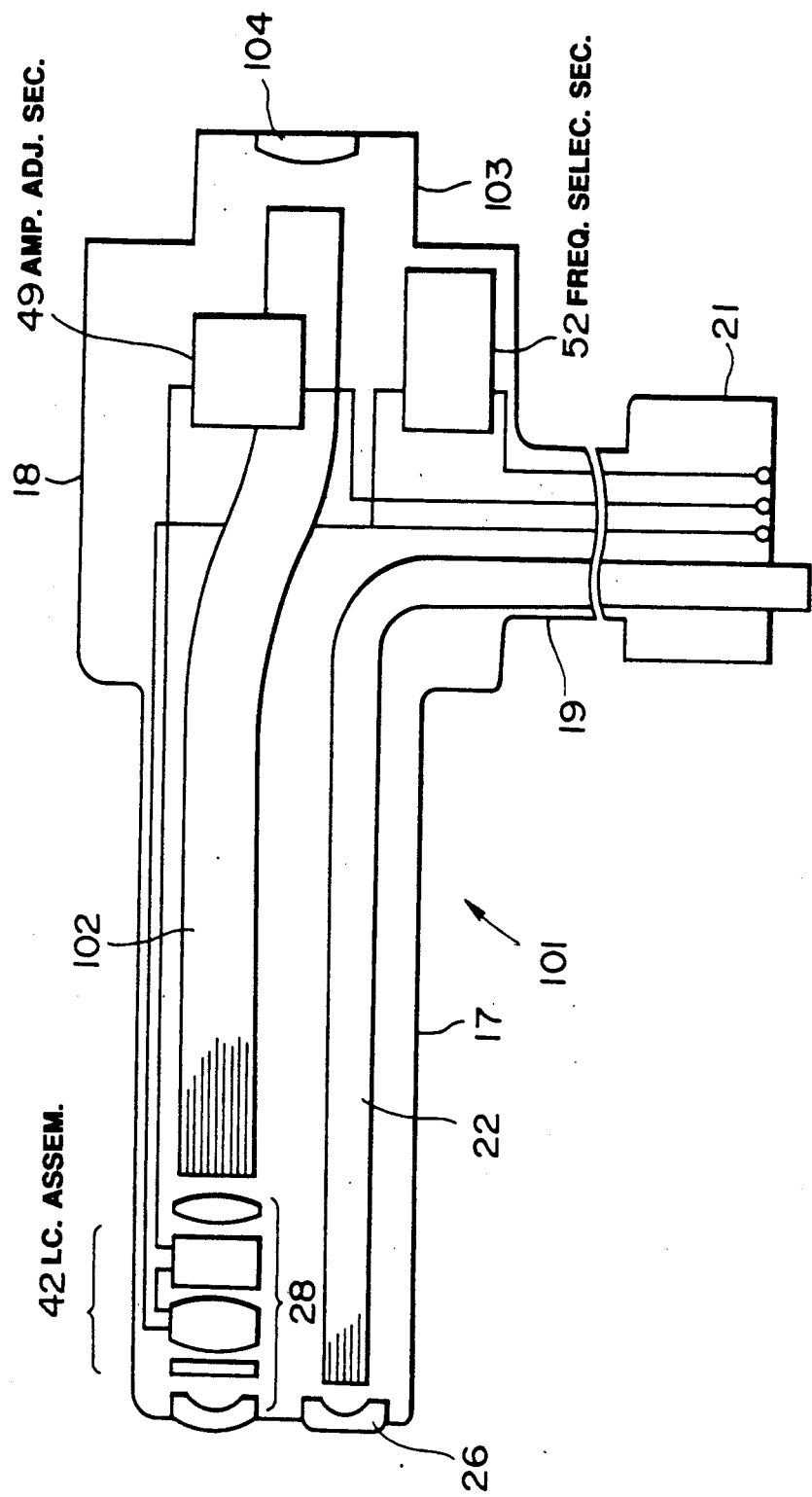
FIG. 16 is a formation diagram of a fiber-scope in the fourth embodiment of the present invention.

In the above described explanation, a liquid crystal assembly as provided in an electronic endoscope is explained. However, it may be provided in a fiber-scope 95 as shown in FIG. 16.

In this fiber-scope 101, an image guide 102 is used instead of the CCD 29 in the electronic endoscope 12 shown in FIG. 2. An optical image by an objective optical system 28 is formed on one end surface of this image guide 102 and is transmitted to the other end surface on the eyepiece part 18 side. An eyepiece lens 104 is arranged as opposed to this other end surface so that the transmitted optical image may be magnified and observed. The others are of substantially the same structure as of the electronic endoscope 12. The same members are shown by bearing the same reference numerals.

The liquid crystal can be applied in the same manner to a rigid endoscope instead of the above mentioned fiber-scope 101.

It is apparent that the liquid crystal assembly can be applied also to the optical system of a photographing apparatus such as a TV camera or still camera. It is also apparent that the liquid crystal assembly can be formed of three or more liquid crystals.

Figure 17:
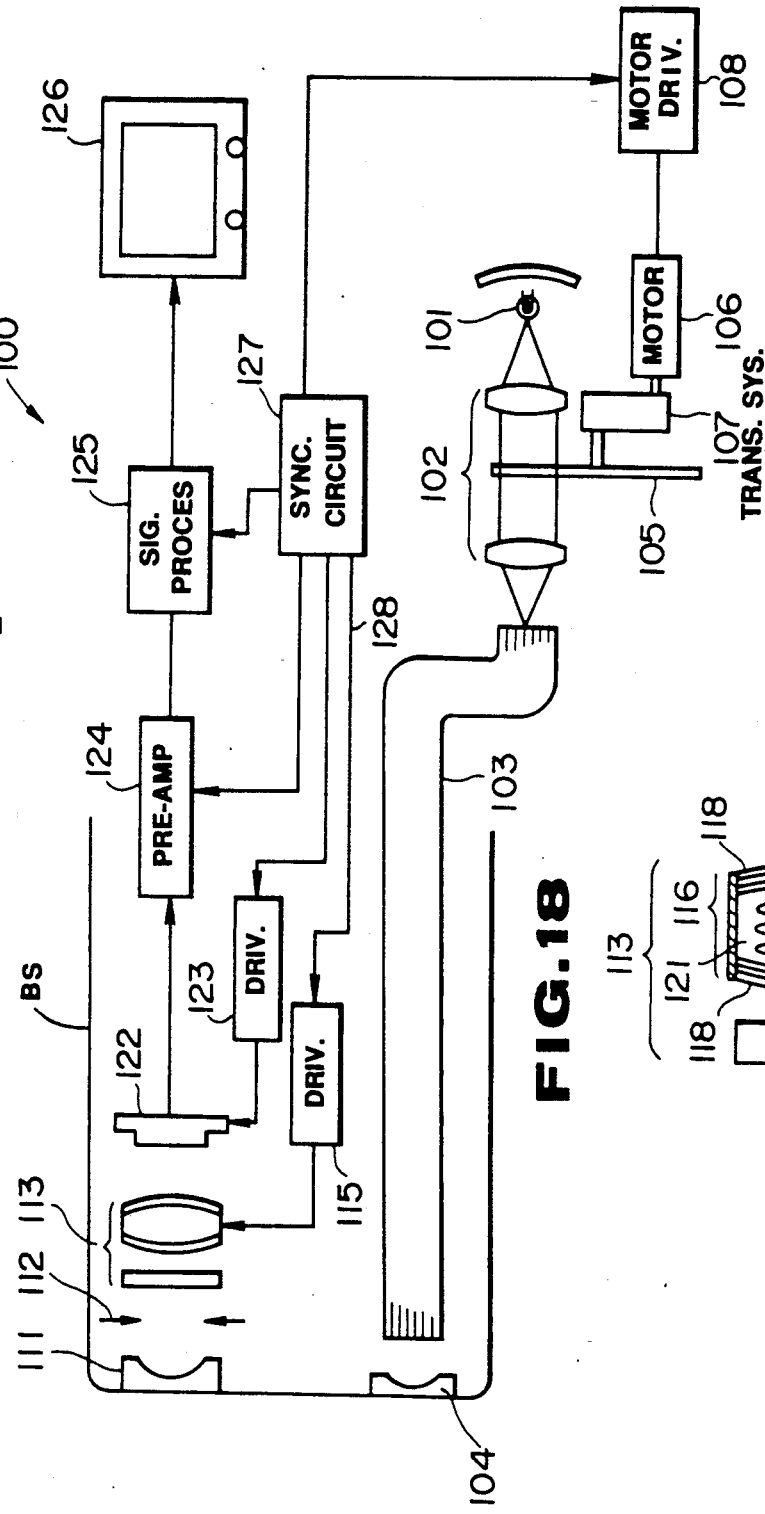
FIG. 17 is a formation diagram of a moire preventing imaging apparatus.

When an imaging apparatus provided with liquid crystal devices and an imaging means such as a CCD, if the driving means is formed as shown in FIG. 17, the production of a moire will be able to be dissolved.

An imaging apparatus 100 shown in FIG. 17 is of a frame sequential color system in which an object illuminated with illuminating lights of different wavelength regions is imaged and is made a color video image. The reference numeral 101 represents a light source lamp, 102 represents a condenser lens making the light from the light source lamp 101 once parallel light beams and then again condensing them, 103 represents a light guide fiber bundle leading to a video scope tip part BS the light condensed by the condenser lens 102, 104 represents an illuminating lens arranged on the end surface of the tip part BS and illuminating an object (not illustrated) with the light emitted from the light guide fiber bundle 103, 105 represents a rotary filter having three filter parts of R, G and B sequentially inserted into the parallel light beam part of the condenser lens 102 by rotation, 106 represents a motor rotating the rotary filter 105 through a transmitting system 107 and 108 represents a motor driving circuit driving the motor 106 at a predetermined frequency to rotate the rotary filter 105 at a predetermined speed. These form an illuminating system radiating light of R, G and B sequentially to the object surface.

The reference numeral 111 represents a concave lens which is arranged on the end surface of the video scope tip part BS and is also a cover glass, 112 represents a brightness iris arranged in the rear of the concave lens 111 and 113 represents a liquid crystal lens arranged further in the rear of it. These form an object lens system 114. The reference numeral 115 represents a driving circuit applying an alternating current voltage of a predetermined frequency to the liquid crystal lens 113 to drive it.

Figure 18:
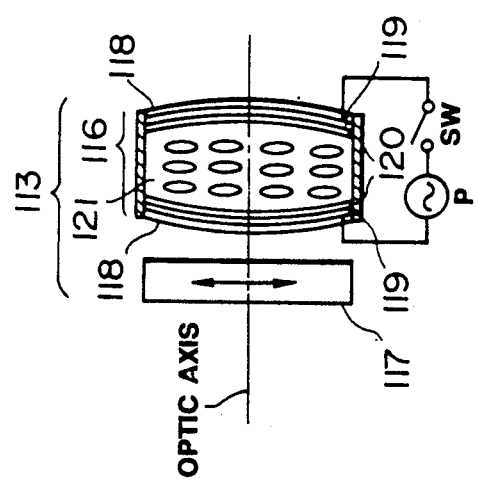
FIG. 18 is a formation diagram of a liquid crystal iris used in the apparatus shown in FIG. 17.

As shown in FIG. 18, the liquid crystal lens 113 comprises a liquid crystal cell 116 and a polarizing plate 117 and the liquid crystal cell 116 is formed by coating the opposed surfaces of two transparent plates 118 which are made of glass or acryl and at least one of which is curved respectively with a transparent electrode 119 and orienting membrane 120 and enclosing a nematic liquid crystal 121 in a convex lens-like air gap formed by these opposed surfaces.

When the switch SW is off and no voltage is applied, the molecule arrangement of the liquid crystal 121 will be a homogenous arrangement in which the direction (rubbing direction) in which the major axes of molecules are arranged is made to coincide with the oscillating direction of the polarizing plate 117. Therefore, the refractive index of the liquid crystal 21 will be high for the incident light having come through the polarizing plate 117 and the focal distance of the liquid crystal lens 113 will be short. In case the switch SW is on and a voltage above a fixed value is applied, the molecule arrangement of the liquid crystal 121 will be a homeotropic arrangement in which the major axis direction of molecules intersects at right angles with the oscillating direction of the polarizing plate 117, therefore the refractive index of the liquid crystal 121 for the incident light will be low and the focal distance of the liquid crystal lens 113 will be long.

The reference numeral 122 represents a solid state imaging device in which an image by the objective lens 114 is formed, 123 represents a driving circuit driving the solid state imaging device 122 at a predetermined frequency to output a video signal (signal of R, G and B), 124 represents a pre-amplifier amplifying the video signal from the solid state imaging device 122, 125 represent a signal processing circuit for processing the video signal from the pre-amplifier 124 to convert it to a composite video signal, 126 represents a television monitor displaying a color image by the input of the composite video signal from the signal processing circuit 125, 127 represents a synchronizing circuit connected to the driving circuits 108 and 123, pre-amplifier 124 and signal processing circuit 125 and synchronizing the operations of those circuits. These together with the above mentioned objective lens 122 form an imaging and observing system.

There has been a problem that, when the liquid crystal lens 113 is alternately driven, apart from the case that the frequency is particularly high, the focal distance of the liquid crystal lens 113 will slightly fluctuate with the frequency and, though the signal is being read out of the solid state imaging device 122 and the rotary filer 105 is being rotated at a predetermined frequency, if such other optical devices as the solid state imaging device 122 and rotary filter 105 than the liquid crystal lens 113 are driven without being synchronized at all, the slight fluctuation of the focal distance of the liquid crystal lens 113 and the variations of the signal reading out of the solid state imaging device 122 and the R, G and B of the rotary filter 105 will interfere with each other to produce moires (stripes flowing in a television image).

In order to prevent a moire pattern from appearing, a synchronizing circuit 127 is connected with the driving circuit 115 of the liquid crystal lens 113 through a signal line 128 so that the liquid crystal lens 113 may be synchronized with the solid state imaging device 122 driving circuit 123, pre-amplifier 124, signal processing circuit 125 and motor 106 driving circuit 108. For example, in case the signal reading-out frequency (field frequency) $f_1$ of the solid state imaging device 122 and the rotation number (frame frequency) $f_2$ of the rotary filter 105 are respectively 90 $H_z$ and 30 $H_z$, the driving frequency $\nu_L$ will be as follows:

$$\nu_L (H_z) = \ldots, 5, 10, 15, 20,$$
$$25, 30, 45, 60, 90,$$
$$120, 150, 180, 210,$$
$$240, 270, \ldots$$

That is, $\nu_L$ is integer times or a fraction of an integer of $f_1$ or $f_2$.

Therefore, according to this apparatus 100, as the liquid crystal lens 113 is synchronized with the drive of the optical devices such as the solid state imaging device 122 and rotary filter 105, the slight fluctuation of the focal distance of the liquid crystal lens 113 and the variation of the signal read out of the solid state imaging device 122 and the R, G and B of the rotary filter 105 will not interfere with each other and no moire will be generated.

There are ranges of $\nu_L$ practical enough even if $\nu_L$ is not an integer times or a fraction of an integer of $f_1$ or $f_2$.

One of the ranges is when $\nu_L$ is higher than $f_1$ and $f_2$, that is, when many liquid crystal lens driving waveforms enter one field and one frame. That is $$\nu_L > 2f_1 \text{ or } \nu_L > 2f_2$$

This is nothing but a condition that the beat of $\nu_L - f_1$ produced by $\nu_L$ and $f_1$ is larger than $f_1$. The same applies also to $f_2$.

On the other hand, in case $\nu_L$ is lower than $f_1$ and $f_2$, $\nu_L$ will be sampled by $f_1$ or $f_2$ in the time and therefore the beat frequency will be $$f_1 - \nu_L \text{ or } f_2 - \nu_L.$$

However, in order that this may not be felt as a flicker to the human eye, it is necessary that $$f_1 - \nu_L > 10 \text{ or } f_2 - \nu_L > 10.$$

There is a problem that, even if the visual field range and illuminating range coincide with each other when the focus is adjusted to be, for example, on the far focus side, when the focus is adjusted to be on the near focus side, a parallax will be produced between the visual field range and the illuminating range and the illuminating state will be so insufficient as to darken a part of the visual field.

In order to solve this problem, the formation may be made as in FIGS. 19 to 34.

Figure 19:
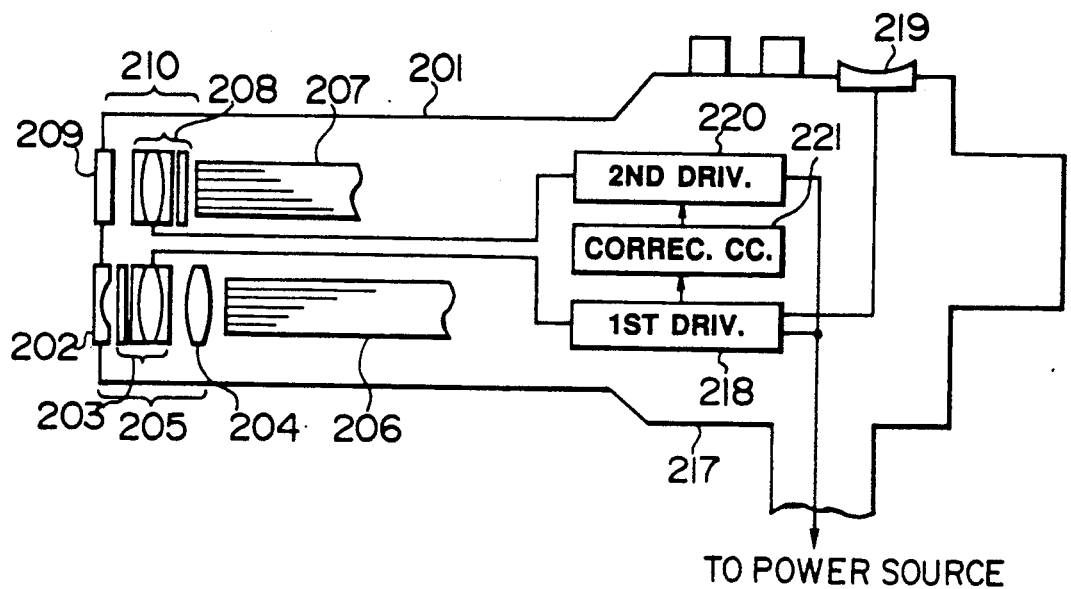

In FIG. 19, the reference numeral 201 represents an endoscope tip part, 202 represents a cover glass and also concave lens arranged on the end surface of the endoscope tip part 201, 203 represents a liquid crystal lens arranged in the rear of the concave lens 202 and 204 represents a convex lens arranged further in the rear of it and these form an objective lens 205. The reference numeral 206 represents an image guide fiber bundle arranged in the rear of the objective lens 205, 207 represents a light guide fiber bundle arranged at the exit end in the endoscope tip part 201 and leading a light from a light source (not illustrated), 208 represents a liquid crystal lens arranged in front of the exit end of the light guide fiber bundle 207 and 209 represents a cover glass arranged in front of the liquid crystal lens 208 and on the end surface of the endoscope tip part 201 and these form an illuminating lens 210.

Figure 20:
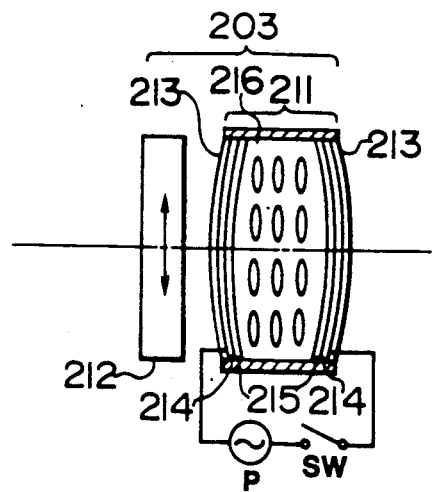

As shown in FIG. 20, the liquid crystal lens 203 comprises a liquid crystal cell 211 and a polarizing plate 212 arranged in front of it. The liquid crystal cell 211 is formed by applying a transparent electrode 214 and orienting membrane 215 to coat each of the surfaces opposed to each other of two transparent plates 213 which are made of glass or acryl and at least one of which is curved and enclosing a nematic liquid crystal 216 in a convex lens-like air gap formed by these opposed surfaces.

While the switch SW is off and no voltage is applied, the molecule arrangement of the liquid crystal 216 will be a homogeneous arrangement wherein the direction (rubbing direction) in which the major axes of molecules are arranged is made to coincide with the oscillating direction of the polarizing plate 212. Therefore, the refractive index of the liquid crystal 216 will be in the state of a high refractive index for the incident light having come through the polarizing plate 212 and the focal distance of the liquid crystal lens 203 will become short. Also, in case the switch SW is on and a voltage above a fixed value is applied, the molecule arrangement of the liquid crystal 216 will be a homeotropic arrangement in which the major axis direction of molecules intersects at right angles with the oscillating direction of the light deflecting plate 212, therefore the refractive index of the liquid crystal 216 for the incident light will be reduced and the focal distance of the liquid crystal lens 203 will become long.

The liquid crystal lens 208 has fundamentally the same structure as of the liquid crystal lens 203.

The reference numeral 217 represents a hand base operating part of the endoscope, 218 represents a first driving circuit arranged within the hand base operating part 217, electrically connected with the liquid crystal lens 203 and a power source (not illustrated) and receiving a signal from a focus adjusting see-saw switch 219 to make the focal distance of the liquid crystal lens 203 long (small in the view angle) or short (large in the view angle) and 220 represents a second driving circuit arranged within the hand base operating part 217, electrically with the liquid crystal lens 208 and a power source (not illustrated) and receiving a signal from the first driving circuit 218 through a correcting processing circuit 221 to make the radiating angle of the liquid crystal lens 208 small (long in the focal distance) or large (short in the focal distance).

Figure 21A:
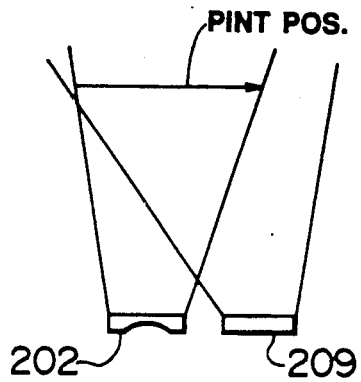
FIG. 21A-21B are explanatory views of a parallax preventing function.
Figure 21B:
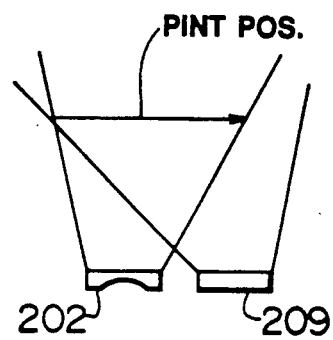

In such a formation as is described above, when the sea-saw switch 219 is operated to make the focal distance of the liquid crystal lens 203 long and th focus position of the objective lens 205 a far focus, as operatively connected with it, as shown in FIG. 21A, the view angle of the liquid crystal lens 208 will become small and the radiating angle of the illuminating lens 210 will become small but, when the focal distance of the liquid crystal lens 203 is made short and the focus position of the objective lens 205 is made a near focus, as operatively connected with it, as shown in FIG. 21B, the view angle of the liquid crystal lens 208 will become large and the radiating angle of the illuminating lens 210 will become large. Therefore, even if the observing state largely varies, the visual field range and illuminating range will be able to be always kept coinciding with each other and, as a result, an optimum illuminating state will be always obtained. If the radiating angle is made large, the illumination will become dark but, as it will be a near focus observing time, the light amount will be sufficient.

A liquid crystal iris or electrochromic iris may be incorporated into the objective lens 205.

Various concrete examples of the objective lens 205 shall be explained in the following.

Figure 22:
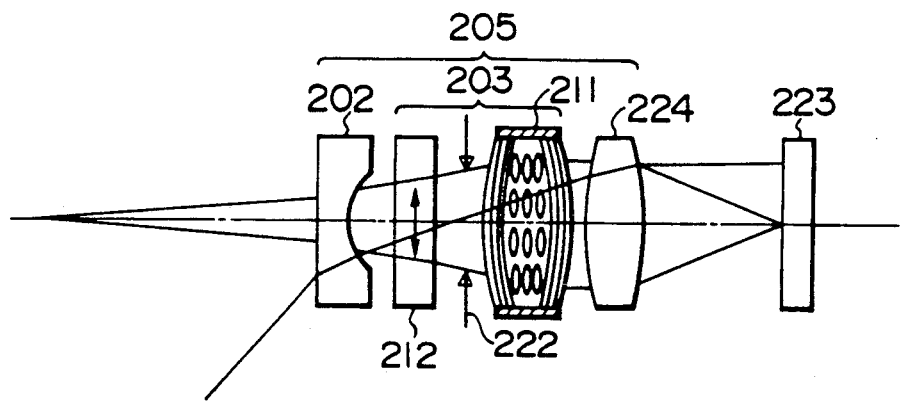

In the example shown in FIG. 22, an iris 222 is arranged between the light deflecting plate 212 of the liquid crystal lens 203 and the liquid crystal cell 211 so that the liquid crystal cell 211 may be positioned near the rear side of the iris 222. In this case, even if th focal distance of the liquid crystal lens 203 is varied and the focus position of the objective lens 205 is varied, the view angle will not substantially vary. The reference numeral 223 represents a solid state imaging device used instead of the image guide fiber bundle 206.

Figure 23:
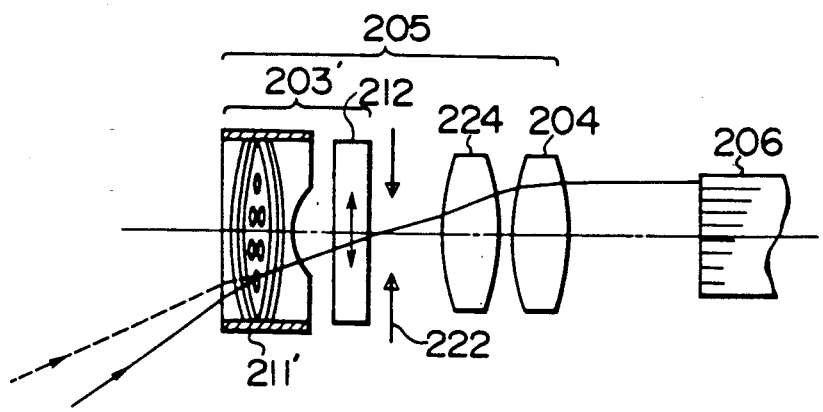
Figure 24:
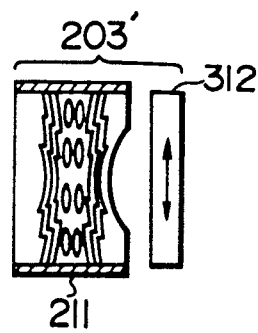

In the example shown in FIG. 23, a negative liquid crystal lens 203' instead of the concave lens 202 is arranged on the front side of the iris 222. In this case, by varying the refractive force of the liquid crystal cell 211' of the liquid crystal lens 203', the view angle can be varied without substantially varying the focus position so that the magnification power of the object image may be varied and the visual field range may be varied. Also, if another liquid crystal lens is arranged near the iris 222 and is operatively connected with the liquid crystal lens 203', the focus position will not be able to be varied at all. The reference numeral 224 represents a convex lens. Also, the liquid crystal lens 203' may be a spherical lens or may be formed of a Fresnel lens as is shown in FIG. 24.

Figure 25:
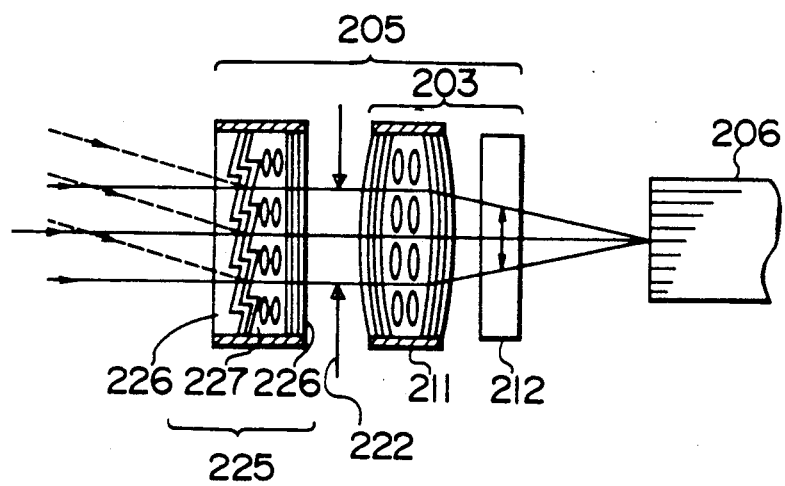
Figure 26:
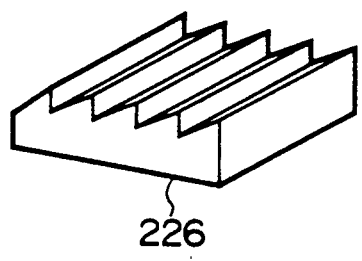

In the example shown in FIG. 25, a visual field direction changing liquid crystal prism 225 is arranged on the front side of the liquid 203 so that the visual field direction may be freely changed. In the liquid crystal prism 225, the inside surface of one transparent plate 226 is made a Fresnel surface as shown in FIG. 26 and the refractive index of a liquid crystal layer 227 is varied so that the refractive angle in the boundary of the liquid crystal layer 227 and transparent plate 226 may be varied. If the refractive index $n_p$ of the transparent plates 226 is made to coincide with the refractive index $n_o$ of the liquid crystal for ordinary rays or the refractive index $n_o$ for abnormal rays, there will be no refraction in the above mentioned boundary when the power source of the liquid crystal prism 225 is on or off and therefore the setting will be easy.

In case the liquid crystal lens is provided within the objective lens and is focused with this lens, the following may be made.

In most cases, the focusing of an optical system having an objective lens of a deep object field depth as of an endoscope is sufficient with so-called zone focusing.

Therefore, an auto-focusing in two steps of a far focus (large distance) side and near focus (small distance) side is considered.

Figure 27:
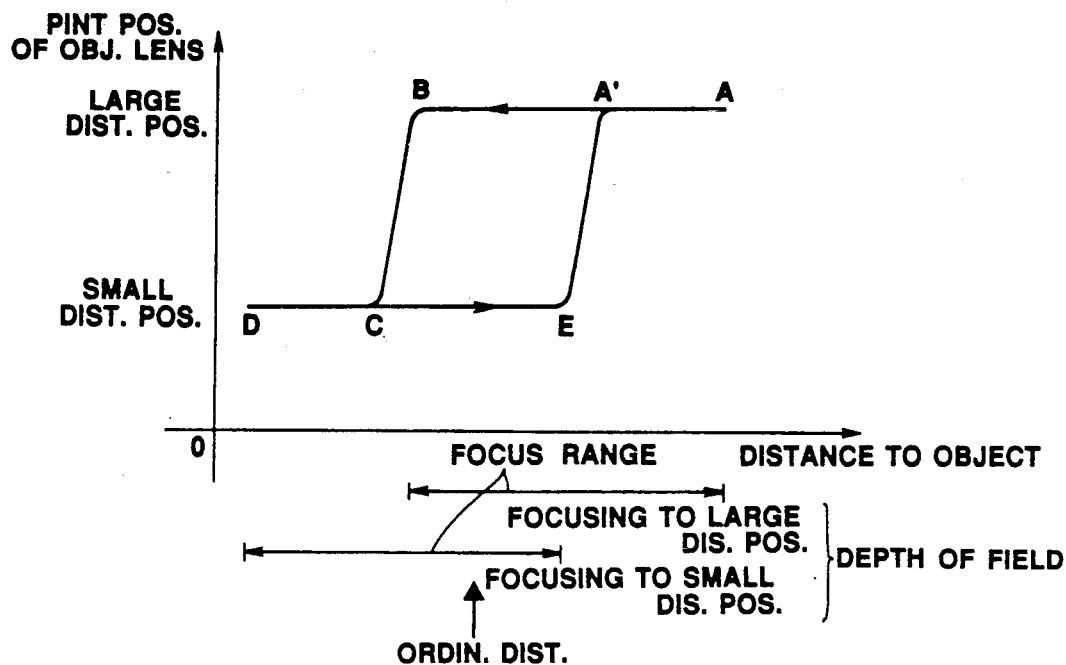

As in FIG. 27, the object field depth when focused on the near focus side and the object field depth when focused on the far focus side are kept overlapped with each other. This overlapped region is an intermediate object distance and is a frequently used distance or a so-called normally used distance. The focusing method is already known. The dulling of an object image formed on an imaging surface may be detected by the solid state imaging device 223 in the case of the electronic scope shown in FIG. 22 or by an image sensor (not illustrated) provided on the emitting side of the image guide fiber bundle 206 in the case of the fiber scope shown in FIG. 23. That is, the output signal from the image sensor is operated by using an evaluating function used for a proper contrast detection or the like of an output difference between adjacent pixels and, for example, when the dulling of the object image on the near focus side becomes larger than the limit clearly seen at the object field depth, the near focus side will be switched to the far focus side (D→C→E→A'→A). Also, on the far focus side, in the same case, on the contrary, the far focus side will be switched to the near focus side (A→A'→B→C→D). Thus, in the normally used distance, an always focused state will be made and it will be no longer necessary to wait until each focusing is made to observe a well used range.

Figure 28:
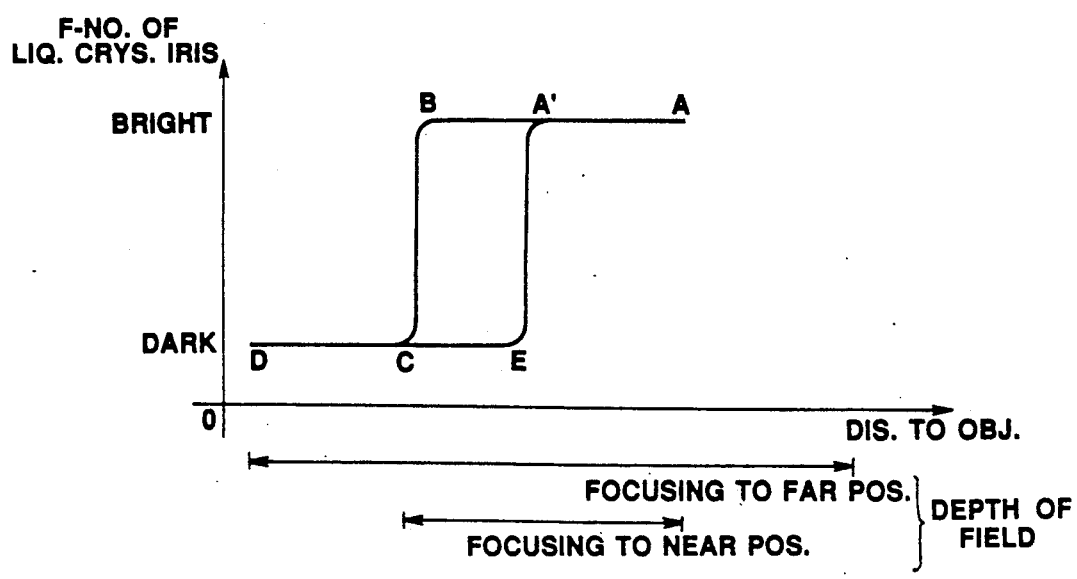

This system can be applied also to the case of automatically operating a two-step switched liquid crystal iris. That is, as shown in FIG. 28, at the time of moving away from the near focus side, $F_{NO}$ of the liquid crystal iris will be made bright (D→C→E→A→→A) and, at the time of nearing from the far focus side, $F_{NO}$ will be made dark (A→A'→B→C→D).

Various examples of the illuminating lens 210 shall be explained in the following.

Figure 29:
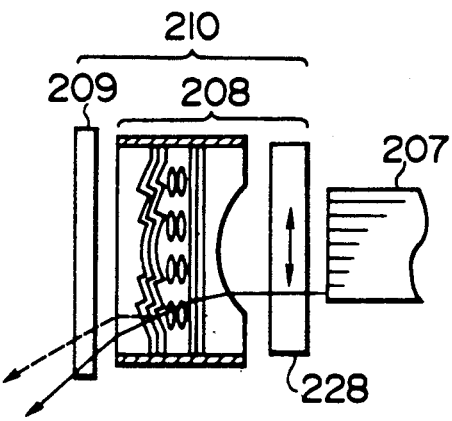

In the example shown in FIG. 29, the liquid crystal lens 208 has a negative refractive force and includes a polarizing plate 228. In this case, when the view angle of the liquid crystal lens 208 is varied, the radiating angle of the illuminating lens 210 will be varied In case the objective lens 205 includes a polarizing plate 212, the polarizing plate 228 may be omitted.

However, in such a case, it is necessary that the orienting direction of the liquid crystal of the liquid crystal lens 208 and the oscillating direction of the polarizing plate 212 of the objective lens 205 should be in a fixed relation.

Figure 30:
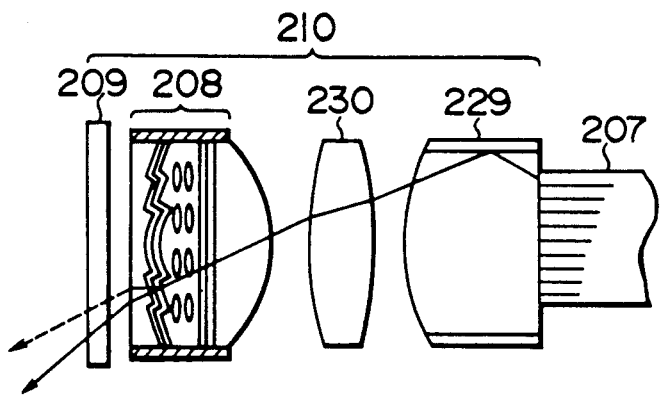

In the example shown in FIG. 30, the whole is formed as a positive lens system, the reference numeral 229 represent a single fiber secured to the exit end surface of the light guide fiber bundle 207 and 230 represents a convex lens. The liquid crystal lens 208 has a positive refractive force and includes no polarizing plate.

Figure 31:
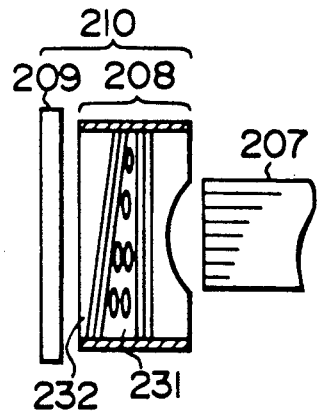

In the example shown in FIG. 31, the liquid crystal lens 208 has a negative refractive force and includes no polarizing plate and a transparent plate 232 on the front side of a liquid crystal layer 231 is wedge-shaped in cross-section so that the refractive index of the liquid crystal layer 231 may be varied, the refracting angle in the boundary of the liquid crystal layer 231 and transparent plate 232 may be varied and thereby the illuminating direction may also be varied.

Figure 32:
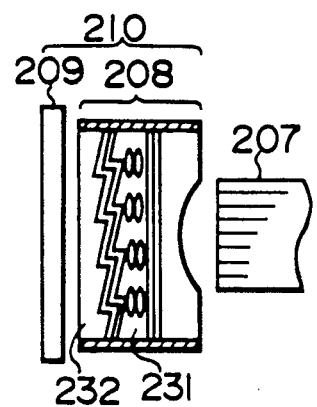

In the example shown in FIG. 32, the liquid crystal lens 208 has a negative refractive force and includes no polarizing plate and surface of the transparent plate 232 on the front side of the liquid crystal layer 231 is made a Fresnel surface as is shown in FIG. 26 so that the illuminating direction may be also varied the same as in the example in FIG. 29.

If the polarizing plate is provided within the illuminating lens 210, the illuminating direction of all the light beams will be able to be uniformly varied but the radiating light amount will become ½. Therefore, in case the objective lens 205 includes a polarizing plate, it will be utilized and its oscillating direction and the orienting direction of the liquid crystal of the liquid crystal lens 208 will be kept in a predetermined relation so that substantially the same effect (i.e., as if the polarizing plate is provided) without providing the polarizing plate within the illuminating lens 210 may be obtained. Also, if the illuminating direction of all the light beams is not required to be varied but the illuminating direction of only a part of the light beams may be varied, the polarizing plate need not be provided. That is a, in such case, depending on the orienting direction of the liquid crystal of the liquid crystal lens 208, the illuminating direction of half the light beams will vary but the illuminating direction of the other half of the light beams will remain unvaried and, if the other half of the light beams is applied at the time of the near focus observation, the light amount will be enough and therefore there will be no problem.

The relationship between the variation of the illuminating direction in the lens 210 and the orienting direction of the liquid crystal shall be explained by using a liquid crystal prism.

Figure 33A:
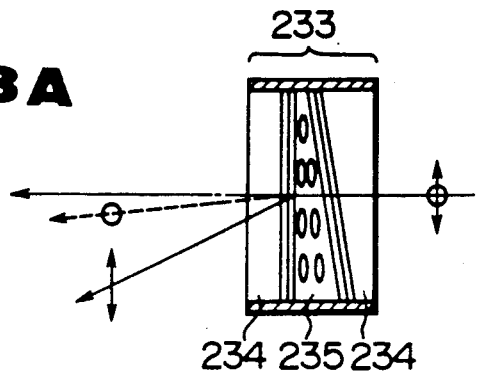
FIG. 33A-33B are explanatory diagrams showing the variation of the illuminating direction.
Figure 33B:
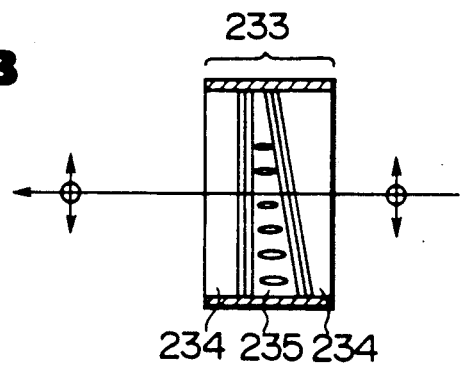

First of all, as shown in FIG. 33A, in case the wedge direction (intersecting at right angles with the optical axis and along the paper surface) of the transparent plate 234 having a wedge-like cross-section of the liquid crystal prism 233 and the orienting direction of the liquid crystal 235 are made to coincide with each other, the difference between the refractive index of the liquid crystal 235 and the refractive index of the transparent bodies 234 on both sides is so small for the polarizing component in the oscillating direction vertical to the paper surface that the polarizing component will not be substantially refracted as illustrated by the broken line. Also, the difference between the refractive index of the liquid crystal 235 and the refractive index of the transparent bodies 234 on both sides is so large for the polarizing component in the oscillating direction intersecting at right angles with the optical axis and along the paper surface that the polarizing component will be largely refracted as illustrated by the solid line. On the other hand, as shown in FIG. 33B, in case the orienting direction of the liquid crystal 235 is made to coincide with the optical axis, as the refractive index of the liquid crystal 235 and the refractive index of the transparent bodies 234 on both sides have been made to coincide with each other for either of the above mentioned polarizing component, either of the above mentioned polarizing component will proceed in the direction coinciding with the optical axis without being refracted. Therefore, as described above, if a polarizing plate in the oscillating direction coinciding with the oscillating direction of the polarizing component varying largely in the refracting angle is provided within the illuminating lens 210, the illuminating direction will be able to be largely varied. When a polarizing plate is provided within the objective lens 205 and only one polarizing component is used, if the oscillating direction of the polarizing plate is kept coinciding with the oscillating direction of the polarizing component varying largely in the refracting angle in the illuminating lens 210, even if the polarizing plate is not provided within the illuminating lens 210, substantially the same effect will be obtained. However, when the oscillating direction of the polarizing component entirely varies in the object, no effect will be obtained. As the liquid crystal lens can be considered to be a continuous body of the above mentioned liquid crystal prism 233, the above mentioned principle will be applied also to the liquid crystal and thereby the light distribution will be able to be controlled.

Figure 34:
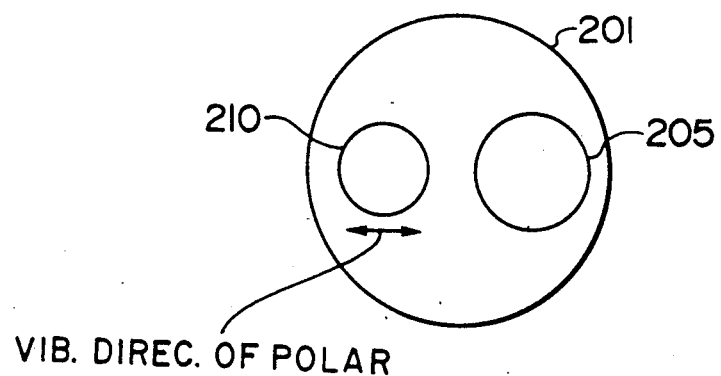

In case a polarizing plate is provided within the illuminating lens 210, as shown in FIG. 34, the oscillating direction had better be made substantially parallel with the straight line intersecting at right angles with both optical axes of the objective lens 205 and illuminating lens 210, because the reflection factor of the polarizing component in the oscillating direction (parallel with object surface) intersecting at right angles with that oscillating direction is so large as to obstruct the observation as of a bright point and therefore the reflection factor is reduced to make the object easy to see.

As in the above, since a liquid crystal lens and liquid crystal prism are provided respectively within the objective lens 205 and illuminating lens 210, the visual field direction, view angle, focus position and the like of the objective lens 205 and the illuminating direction and radiating angle of the illuminating lens 210 can be freely varied. When the liquid crystal lens and liquid crystal prism of both are operatively connected, the illuminating direction, radiating angle and the like of the illuminating lens 210 can be varied in response to the variation of the visual field direction, view angle, focus position and the like of the objective lens 205. For example, in case, of the objective lens 205, without varying the focus position, the view angle is varied, the magnification power of the object image is varied and the visual field range is varied, if the radiating angle of the illuminating lens 210 is varied in conformity with them, th illuminating efficiency will be the best. In case the focus position of the objective lens 205 is on the near focus side, the illuminating direction and radiating angle may be operatively connected with each other to remove the parallax between the visual field range and illuminating range. Also, varying the visual field direction of the objective lens 205, only the illuminating direction, only the radiating angle or the illuminating direction and radiating angle as operatively connected of the illuminating lens 210 may be varied in conformity with it.

Thus, even if the observing state varies greatly, the visual field range and illuminating range will be able to be kept always coinciding with each other and therefore an optimum illuminating state will be always obtained.

In case an electric optical such as a liquid crystal iris is used in an endoscope, a driving signal of a proper voltage and current must be fed from outside to normally operate the optical device. However, if a problem such as a line break occurs to the driving system and the electricity passed to the liquid crystal optical device is interrupted, the liquid crystal optical device will not operate. In such a case, an observing state of normal brightness will not be able to be secured. As described above, the part to be observed with the endoscope is very dark in the ordinary state as within a body cavity, the range effectively reached by the illuminating light is limited, the brightness matching the part to be observed variously greatly fluctuates and therefore, due to the above mentioned problem, the subsequent observation may not be well made. Particularly, in the endoscope inspection to observe internal organs of a living body, the necessity of securing safety is so high that it is a great problem. Such circumstances are the same also in the case of adjusting the focal distance.

In order to solve this problem, a structure as is shown in FIGS. 35 to 41 is desirable.

The above mentioned structure is summarized to be of contents as in the following. An observing optical system comprises an electric optical iris device which will be on the small caliber side when a driving signal is fed but will automatically return to the large caliber side when the feed of the driving signal is stopped, an electric optical lens device which will be on the near focus side when a driving signal is fed but will automatically return to the long focal distance side when the feed of the driving signal is stopped, a light amount detecting means for detecting the amount of the light incident upon the above mentioned observing optical system and a driving circuit adjusting the level of the driving signal fed to the above mentioned electric optical iris device and electric optical lens device on the basis of the output of this light amount detecting means and controlling the operation of the electric optical iris device and electric optical lens device.

When the driving circuit outputs a driving signal in response to the output of the light amount detecting means detecting the amount of the light incident upon the observing optical system of the endoscope, the electric optical iris device will shift to the small caliber side in response to it and the electric optical lens device will shift to the near focus side. Thereby, even when the endoscope moves away from or moves near to the object to be observed, the focus will not be out, no halation will be caused by the excess light amount and an optimum observation will be able to be made at a high magnification power. This operation is automatically made and the endoscope handling operator need not purposely make the adjusting operation. Therefore, in making various inspecting operations, as any further optical system adjusting operation need not be made, the endoscope inspecting operatability will improve.

When the applied voltage does not reach the driving level, the electric optical iris device will return to the large aperture caliber side and the electric optical lens device will shift to the long focal distance side. Therefore, even if a problem as a line break occurs to the driving system and the electricity passed to the respective liquid crystal optical devices is interrupted, a wide range of a bright visual field will be able to be observed in conformity with the far focus part. Therefore, even under the above mentioned abnormal circumstances, the observation with the endoscope can be secured and safety is secured.

Figure 35:
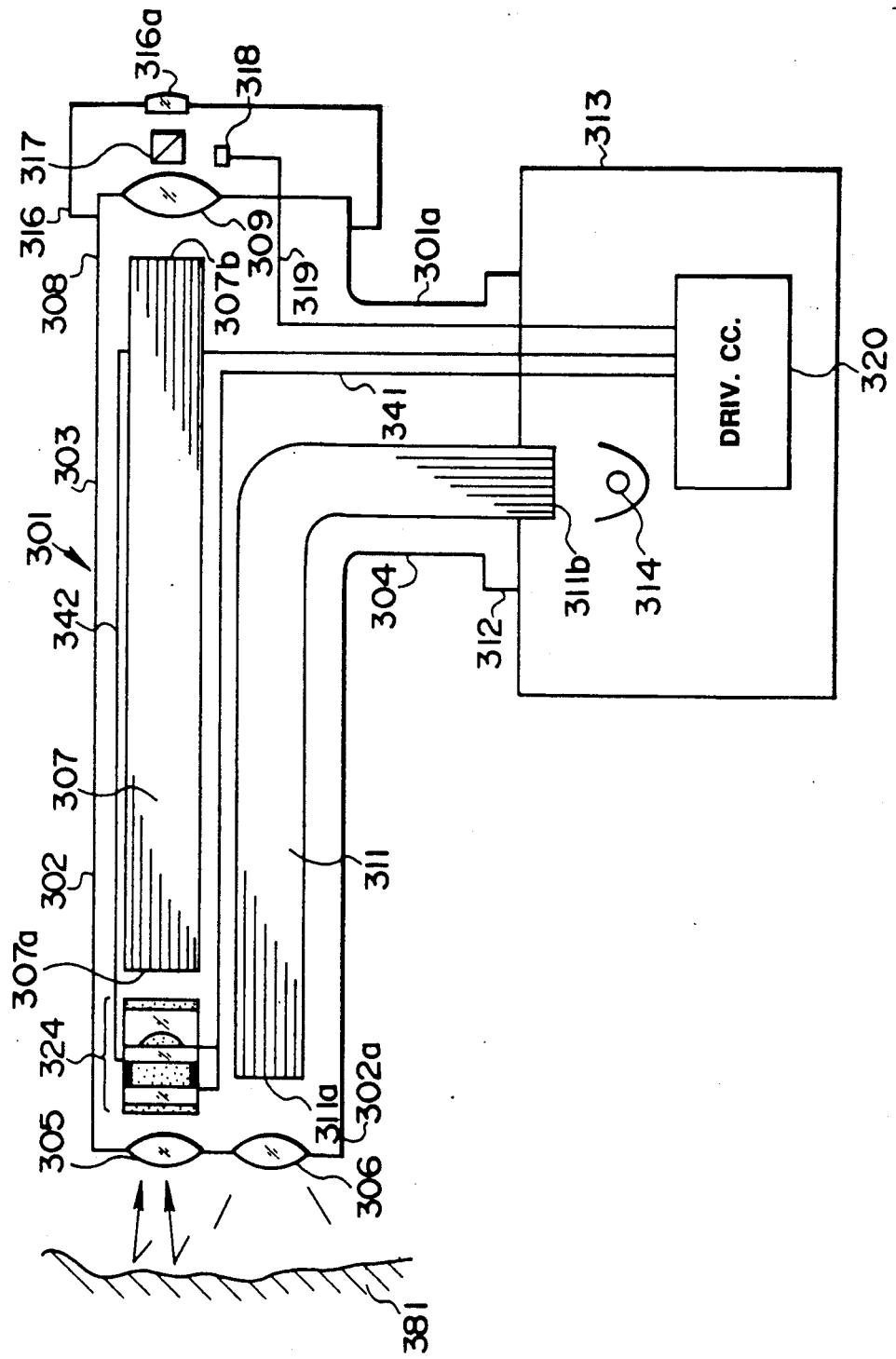

The formation shall be explained in the following with reference to FIGS. 35 an others following it. In FIG. 35 schematically showing the entire formation of an endoscope apparatus (system), the reference numeral 301 represents an endoscope forming an endoscope body 301a of an insertable part 302, hand base operating part and light guide cable 304. An objective lens 305 and illuminating window glass 306 of an objective optical system in an observing optical system are provided on the tip surface of the tip part 302a of the insertable part 302. The entrance tip surface 307a of an image guide 307 consisting of an optical fiber bundle opposed to the objective lens 305 through a later described electric optical device apparatus part 324. This image guide 307 is led to an eyepiece part 308 of the hand base operating part 303 through the respective interiors of the insertable part 302 and hand base operating part 303. The exit end surface 307b of the image guide 307 is opposed to an eyepiece lens 309 of the eyepiece part 308.

Also, the exit tip surface 311a of a light guide 311 consisting of an optical fiber bundle is opposed to the illuminating window glass 306. This light guide 311 reaches a connector 312 at the extended tip of the light guide cable 304 through the respective interiors of the insertable part 302, hand base operating part 303 and light guide cable 304. The connector 312 is removably connected to an electric light source apparatus 313. When this connector 312 is connected to the electric light source apparatus 313, the entrance end surface 311b of the light guide 311 will be opposed to a light source lamp 314.

An endoscope camera 316 is removably fitted to the eyepiece part 308 of the endoscope 301 so that the observed image by the endoscope 301 may be photographed. A prism 317 as a light dividing means is provided in the course of an entrance light path of this endoscope camera 316 and a light receiving device 318 as a later described light amount detecting means is set on the side of this prism 317 so that the light divided by the prism 317 may be incident upon the light receiving device 318. The output detected by the light receiving device 318 is transmitted to a driving circuit 320 provided in the above described electric light source apparatus 313 through a signal line 319. This signal line 319 is led to the electric light source apparatus 313 through the light guide cable 304 from the hand base operating part 303.

Figure 36:
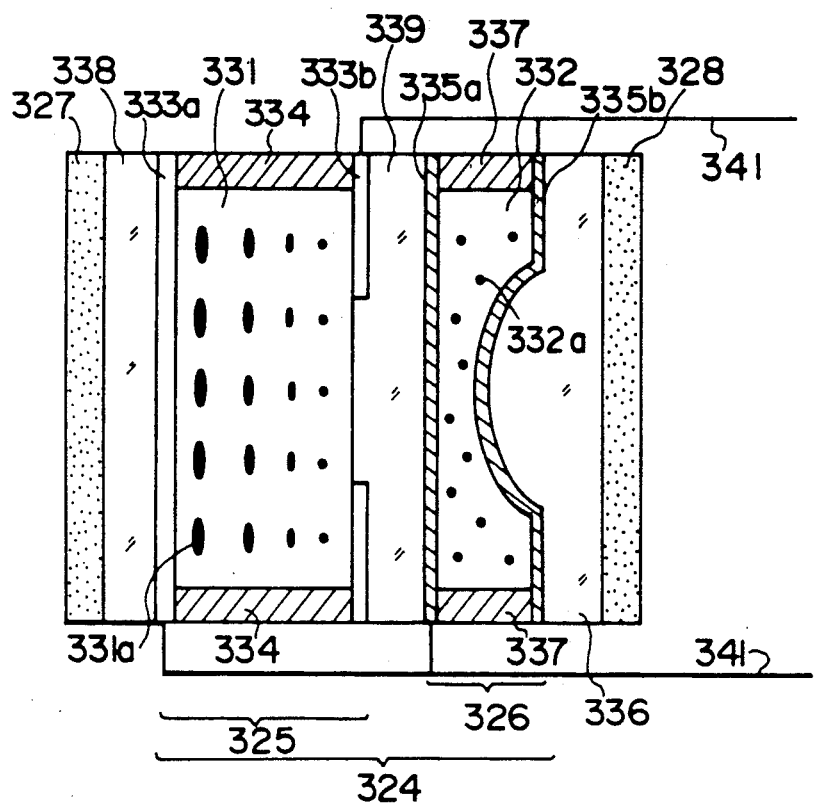

On the other hand, the above mentioned electric optical device apparatus part 324 is formed as shown in FIG. 36. That is, a liquid crystal iris part 325 as an electric optical iris device and a liquid crystal lens part 326 as an electric optical lens device positioned in the rear of this liquid crystal iris part 325 are incorporated to be formed as one unit body. Polarizing plates 327 and 328 of the liquid crystal iris part 325 and liquid crystal lens part 326 are used in common. The polarizing plates 327 and 328 are set respectively at the foremost end and rearmost end with both liquid crystal parts 331 and 332 held between them. Orienting membranes (not illustrated) and transparent electrodes 333a and 333b are arranged on both front and rear surfaces of the liquid crystal part 331 of the liquid crystal iris part 325 so that a driving voltage may be applied to the liquid crystal part 331 by the transparent electrodes 333a and 333b. The reference numeral 334 represents a spacer. Further, as shown in FIG. 36, the axial direction of the liquid crystal molecule 331a is twisted by 90 degrees in the course from one transparent electrode 333a to the other transparent electrode 333b when no voltage is applied. The transparent electrode 333b on the rear end side lacks the central part so as not to act on the liquid crystal molecules 331a corresponding to this central part.

Also, orienting membranes (not illustrated) and transparent electrodes 335a and 335b are arranged on both front and rear surfaces of the liquid crystal part 332 of the liquid crystal lens part 326 so that a driving voltage may be applied to the liquid crystal part 332 by the transparent electrodes 335a and 335b. The liquid crystal part 332 of this liquid crystal lens part 326 is arranged to be like a concave lens outside a spherical convex part 336 of a lens member 326 formed of such transparent material as glass. The reference numeral 337 represents a spacer interposed between the above mentioned transparent electrodes 335a and 335b.

If the refractive index of the material forming the liquid crystal lens part 326 is represented by n and the radius of curvature of the lens part is represented by r, the refractive force D in this liquid crystal lens part 326 will be represented as $$D=(n-1)/r.$$

Therefore, the liquid crystal lens part 326 is refractive. The second polarizing plate 328 in the rear transmits only a light having an amplitude in the direction vertical to the paper surface.

Transparent glass plates 339 and 338 are closely inserted respectively between the above mentioned liquid crystal iris part 325 and liquid crystal lens part 326 and between the liquid crystal iris part 325 and polarizing plate 327. The spaces between the respective parts are sealed with sealing materials adapted to the spaces.

Figure 37:
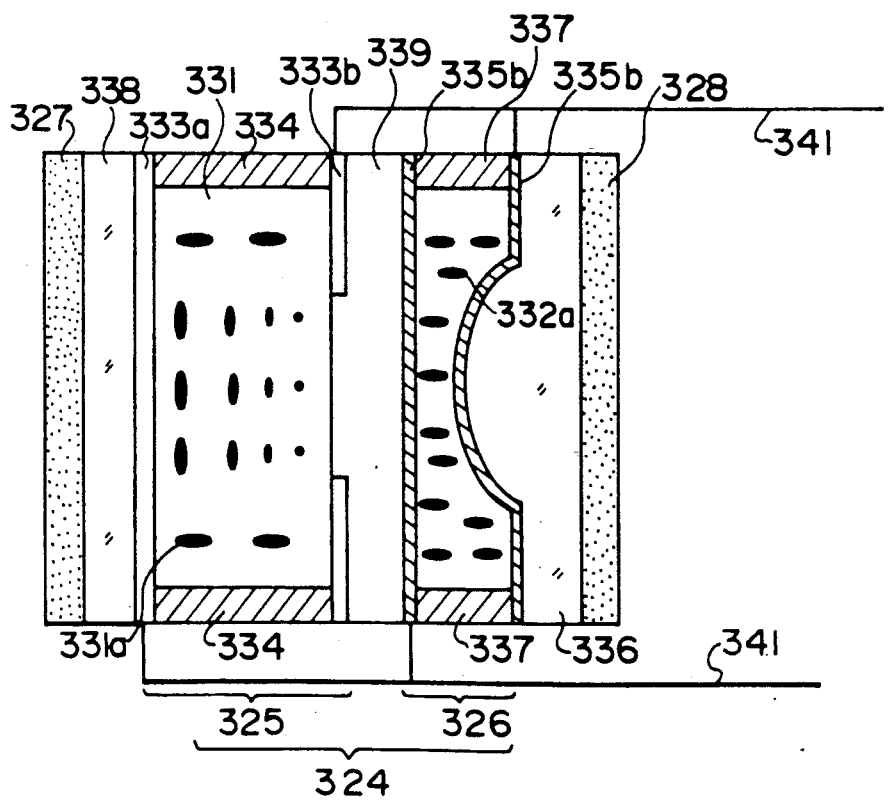

When no voltage is applied to the transparent electrodes 333a and 333b of the above mentioned liquid crystal iris part 325, as shown in FIG. 36, the oriented state of the liquid crystal molecules 331a will not vary. That is; the respective polarizing plates 327 and 28 will maintain a relative state of transmitting the light. When a voltage is applied to the transparent electrodes 333a and 333b, as shown in FIG. 37. the oriented state of the liquid crystal molecules 331a will vary to be a homeotropic arrangement. At this time, as the rear transparent electrode 333b lacks the central part, the voltage will not be applied to the liquid crystal molecules 331a in the central part and therefore the state of the liquid crystal molecules 331a in the central part will not vary. Therefore, the same light as in the above will be transmitted through this central part. However, as the liquid crystal molecules 331a in the peripheral part are held by the transparent electrodes 333a and 333b, when a voltage is applied, the arrangement will vary. Therefore, the light transmitted through this peripheral part will not be able to be transmitted through the polarizing plate 328 in the rear. That is, the transmitted light amount as a whole will be throttled (i.e., decrease).

On the other hand, when no voltage is applied to the transparent electrodes 335a and 335b of the liquid crystal lens part 326, the orientation of the liquid crystal molecules 332a will be in such a state as is shown in FIG. 36 and the focus position at this time will be on the far focus side. Therefore, in case a voltage is applied to the transparent electrodes 335a and 335b, as shown in FIG. 37, the oriented state of the liquid crystal molecules 332a will vary and the focus position will shift to the near distance side in response to the size of the applied voltage. That is, the focus position will analogously shift in response to the voltage applied to the transparent electrodes 335a and 335b.

The liquid crystal iris part 325 and liquid crystal lens part 326 of the thus formed electric optical device apparatus part 324 are driven by the driving circuit 320 provided in the electric light source apparatus 313 respectively through lead wires 341 and 342. There are considered two kinds of liquid crystal driving systems of a controlling system by the voltage (varying the optical characteristics of a liquid crystal with a large or small voltage with the threshold value voltage of the liquid crystal as a boundary) and a controlling system by the frequency (varying the optical characteristics of a liquid crystal by applying a voltage of a high or low frequency).

Figure 38:
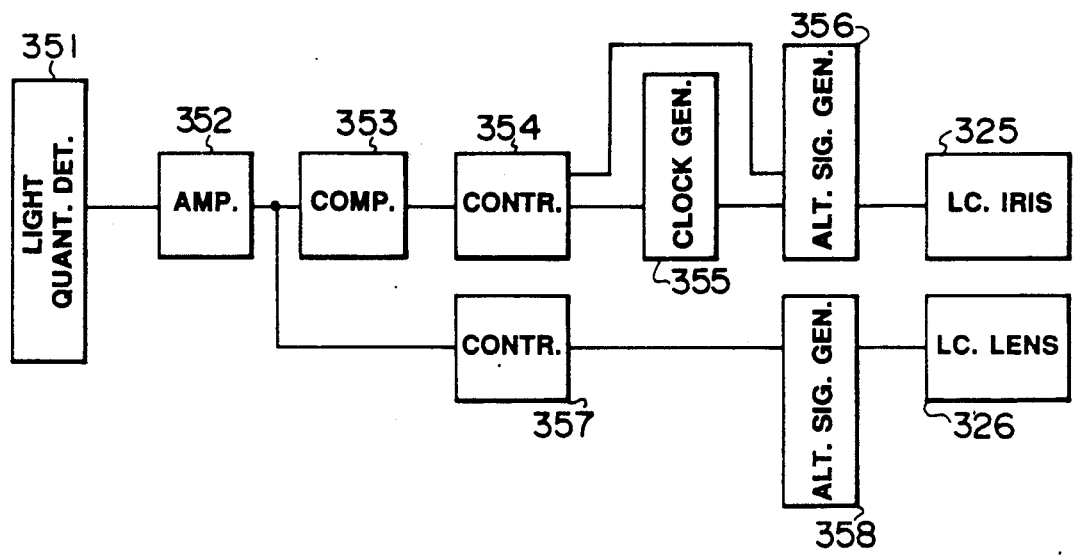

A schematic example of a driving system realizing it shall be explained with reference to FIG. 38. In the case of a liquid crystal iris part 325, there is provided an amplifying means 352 for amplifying the output of a light amount detecting means 351 for detecting the light amount in response to the light amount incident from an objective lens. The signal amplified up to a required signal level by this amplifying means is input into a comparing means 353 and is here transmitted as information of the present light level to a controlling means 354 for determining whether to switch the liquid crystal iris part 325 in order to open or close it. By the given information of the light amount level, the controlling means 354 generates a signal switching on/off the operation of a standard clock generating means 355 for voltage control or controlling the frequency of the standard clock generating means 355 to be high/low for frequency control. In an alternating signal generating means 356 receiving this signal, the clock of the standard clock generating means 355 is made an alternating signal which is given to the liquid crystal iris part 325 of the electric optical device apparatus 324 considered to be of a capacitance load.

For the liquid crystal lens part 326, a signal obtained by amplifying, to a required signal level by the amplifying, means 352 the output of the light amount detecting means 351 for detecting the light amount incident from the objective lens 305, is input into a controlling means 357. The controlling means 357 gives a controlling signal controlling the focal distance of the liquid crystal lens part 326 to be long or short in response to the present light amount level to an alternating signal generating means 358. The alternating signal generating means 358 varies the voltage for voltage control or varies the frequency to be high/low in the case of the frequency control and gives it as an alternating signal to the liquid crystal lens part 326 of the electric optical device apparatus 324 considered to be of a capacitance load.

The above mentioned standard clock may generate sinusoidal waves. In this case, inverse phase waves are made and are fed to the liquid crystal iris part 325 and liquid crystal lens part 326 through a buffer amplifier. Generally, when the temperature is low, the responding speed of a liquid crystal device will reduce with it. Therefore, in order to improve the temperature characteristic, the liquid crystal driving voltage or liquid crystal driving frequency is made variable and a sensor detecting the temperature corresponding to the temperature of the liquid crystal is incorporated. In case the temperature is low, the liquid crystal driving voltage or liquid crystal driving frequency may be shifted to the side on which the responding speed is elevated by the detecting signal by the sensor to compensate the temperature.

Figure 39:
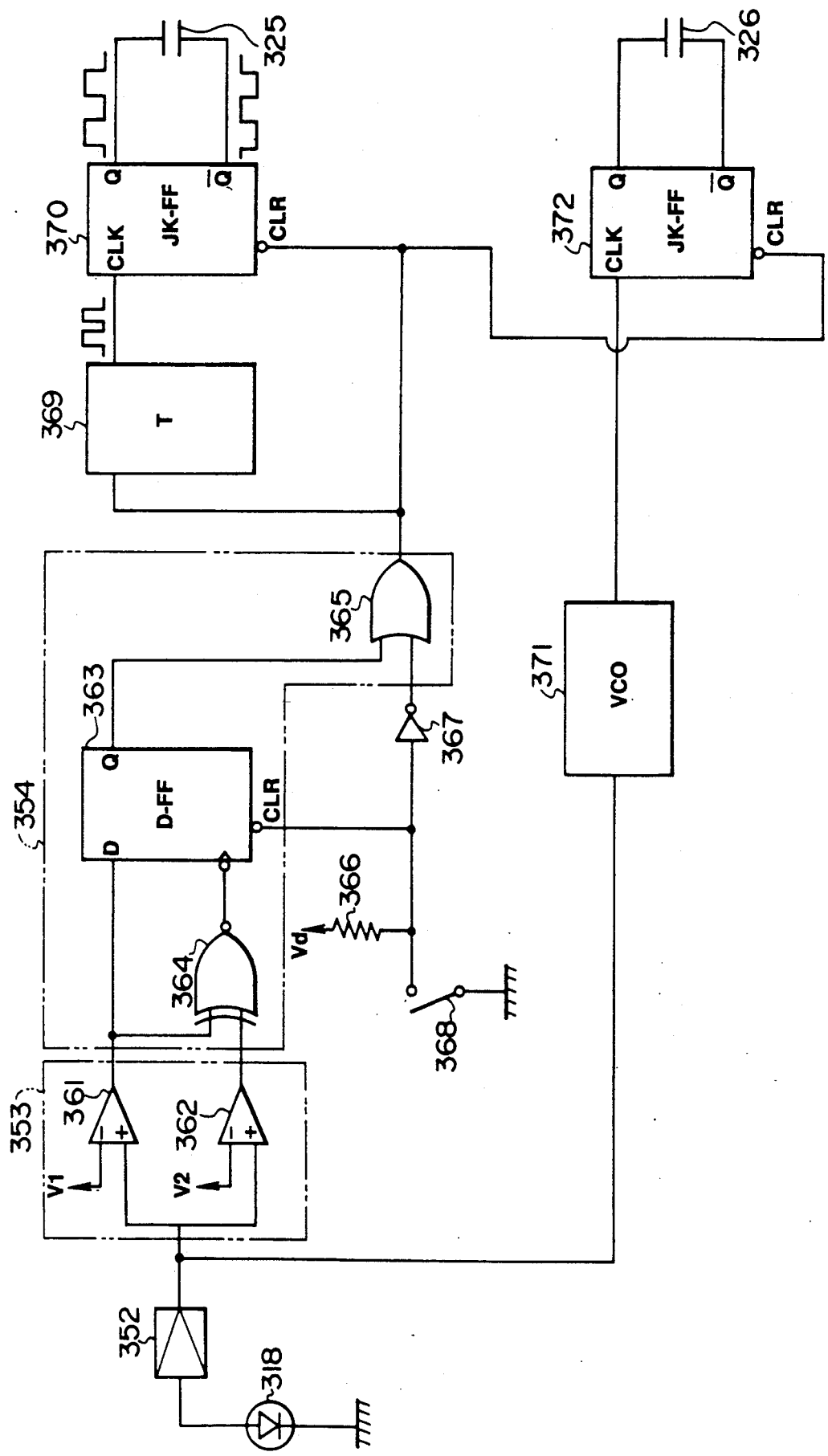

A circuit example of a liquid crystal driving system which is a system controlled by the frequency shall be explained with reference to FIG. 39 in which a light receiving device 318 is formed, for example, of a photodiode and the detecting signal of this light receiving device 318 is amplified up to a predetermined level by an amplifying means 352. An amplifying FET is used for the amplifying means 352 but an operating amplifier high in input impedance may be utilized. This amplified signal is input into respective non-inverted input terminals of a first comparator 361 and second comparator 362 forming a window comparator as a comparing means 353. A first standard voltage $V_1$ is applied to he inverted terminal of the first comparator 361 and a second standard voltage $V_2$ is applied to the inverted terminal of the second comparator 362. In this case, the relationship between the first standard voltage $V_1$ and second standard voltage $V_2$ is $V_1 < V_2$. As it has two comparing voltages $V_1$ and $V_2$, the operation of switching the liquid crystal state of the liquid crystal iris part 332 in the electric optical device apparatus part 324 as described later will not be frequently repeated and the operation will be stabilized.

The output of the first comparator 361 is input into an input terminal D of a D-type flip-flop circuit 363 and one input terminal of an exclusive NOR gate 364. The output of the second comparator 362 is input into the other input terminal of the exclusive NOR gate 364. The inverted output signal of the exclusive NOR gate 364 is input into a clock input terminal of the D-type flip-flop circuit 363.

The output of the D-type flip-flop circuit 363 is input into one input terminal of an OR gate 365. A predetermined voltage Vd is applied to a clear input terminal of the D-type of the D-type flip-flop circuit 363 through a resistance 366 and is also input into the other input terminal of the above mentioned OR gate 365 through a resistance 366 and NOT gate 367. The voltage Vd side is grounded through a manual switch 368 for forced throttling. The manual switch 368 is normally opened but, when it is closed by a manual operation, it will be a ground potential. This potential is input as a clear signal into a clear terminal of the D-type flip-flop circuit 363 is inverted by the NOT gate 367 and is input into the OR gate 365.

The output of the OR gate 365 is input into an oscillating circuit 369 as a standard clock generating means 355 and is input also into a clear input terminal of a JK-type flip-flop 370 as an alternating signal generating means 356. When the output of the OR gate 365 becomes logical "1", the oscillating circuit 369 will operate and will output a signal of a predetermined frequency. The JK-type flip-flop 370 receives and divides this signal, outputs alternating signals (for driving) of phases inverse to each other at a Q output end and $\bar{Q}$ output end and applies them between the transparent electrodes 333a and 333b of the liquid crystal iris part 325.

On the other hand, the detecting signal of the light receiving device 318 amplified up to a predetermined level by the amplifying means 352 is input into a controlling oscillating circuit 371 as a controlling means 357 for controlling the liquid crystal lens part 326. In order to adjust the focus of the liquid crystal lens part 326 to be long or short in response to the detecting level (input voltage level), this controlling oscillating circuit 371 inputs a signal varying to be high or low in response to the detecting level into the clock terminal of the JK-type flip-flop 372 as the alternating signal generating means 358. The JK-type flip-flop 372 receives and divides it, outputs alternating driving signals of phases inverse to each other from the Q output end and $\bar{Q}$ output end and applies them between the transparent electrodes 335a and 335b of the liquid crystal lens part 326 of the electric optical device apparatus 324.

The operation of the above mentioned formation shall be explained in the following. When the insertable part 302 of the endoscope 301 is inserted into a body cavity and an illuminating light is introduced through the light guide 311 from the light source lamp 314 of the electric light source apparatus 313 and is radiated toward an object 381 to be inspected from the illuminating window glass 306, the illuminating light will reflect on the object 381, will enter the electric optical device apparatus part 324 from the objective lens 305 of the objective optical system, will be transmitted under an optical action and will form an image on the entrance tip surface 307a of the image guide 307. This optical image is led through the image guide 307 and is transmitted to the endoscope camera 316 through the eyepiece lens 309 of the eyepiece part 308. The operator can photograph the image with the camera 316 and can observe through the view finder 316.

Figure 40A:
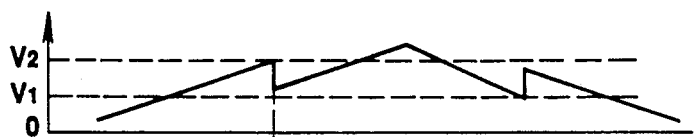
FIGS. 40A-40F show operation explaining diagrams of FIG. 39.

On the other hand, the light led to the light receiving device 318 provided within the endoscope camera 316 is photoelectrically converted there and a detected value corresponding to the light amount incident from the objective lens 305 of the endoscope 301 is obtained. The signal detected by this light receiving device 318 is amplified up to a predetermined level by the amplifying means 352 and is compared with the first standard voltage $V_1$ and second standard voltage $V_2$ respectively in the first comparator 361 and second comparator 362. The levels of the signals input into the respective comparators 361 and 362 shall be as shown in FIG. 40a.

Figure 40B:
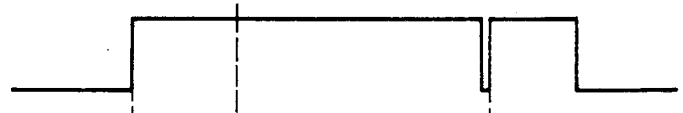
Figure 40C:
Figure 40D:
Figure 40E:
Figure 40F:

Therefore, for example, in case a magnified photograph or observation is to be made by approaching the object 381, the object 381 will become very bright, a halation or ghost will be generated and the observation will be likely to be difficult but, at this time, the input voltages to the respective comparators 361 and 362 will rise. Thus, when the input voltage exceeds $V_1$, the output of the first comparator 361 will be logic "1". When the input voltage exceeds $V_,$, the output of the second comparator 362 will be logical "1". The outputs of the respective comparators 361 and 362 are shown in FIGS. 40b and 40c. By receiving the outputs of the respective comparators 361 and 362, the output of the exclusive NOR gate 364 will be as shown in FIG. 40d and its inverted signal will be as shown in FIG. 40e. By the rise of this signal, the D-type flip-flop circuit 363 latches the output of the first comparator 361. Thus, when the output of the OR gate 365 becomes logical "1", the oscillating circuit 369 will operate and the JK-type flip-flop 370 will be set. Therefore, alternating driving signals of phases inverse to each other will be output from the Q output end and $\overline{Q}$ output end of the JK-type flip-flop 368 and will be applied the transparent electrodes 333a and 333b of the liquid crystal iris part 325 of the electric optical device apparatus part 324. That is, it will be the same as applying an apparently double voltage between the transparent electrodes 333a and 333b of the liquid crystal iris part 325. Thereby, the liquid crystal iris part 325 will be throttled as shown in FIG. 37. Therefore, the excess brightness of the surface of the inspected object 381 will be dissolved.

On the other hand, at the same time, the detecting signal of the light receiving device 318 amplified up to a predetermined level by the amplifying means 352 is input into a controlling oscillating circuit 371 for controlling the focus of the liquid crystal lens part 326 and this controlling oscillating circuit 371 elevates the frequency oscillated by the JK-type flip-flop 372. Thus, the high frequency and alternating signals of inverse phases are produced at the Q output end and $\overline{Q}$ output end of the JK-type flip-flop and are applied to the transparent electrodes 335a and 335b of the liquid crystal part 326. Therefore, the focus will be shifted to the near distance side of the liquid crystal lens part 326 and will be in a proper focus position That is, even if the inspected object 381 is approached, it will be automatically focused.

By the composite effects that, in case the endoscope 301 approaches the object 381 to be inspected, by the light adjusting function and throttling effect by the liquid crystal iris part 325, the photographed field depth will expand and the focus position by the liquid crystal lens part 326 will shift to the short focus side, the magnified observation in the approached state can be well made. On the other hand, by the composite effects that, when the object 381 is kept far away to observe a wide range, the light amount entering the light receiving device 318 will reduce and, therefore, in response to it, the liquid crystal iris part 325 will open to elevate the brightness and the focus position will shift to the long focus side in the liquid crystal lens part 326, the wide range can be well observed while securing brightness. That is, a favorable observation can be made in response properly to the special observing state of the endoscope 301.

As alternating driving signals of phases inverse to each other are applied to drive the transparent electrodes 333a, 333b, 335a and 335b of the liquid crystal iris part 325 and liquid crystal lens part 26, they can be driven at a low voltage. Therefore, the power source of the conventional endoscope camera can be utilized and all the circuits can be built-in within the endoscope 301.

While the above mentioned endoscope 301 is being used, the lead wires 341 and 342 feeding the driving signals to the transparent electrodes 333a and 333b of the above mentioned liquid crystal iris part 325 may break or other electricity passing systems may break so that no driving signal may be fed to the transparent electrodes 333a and 333b of the liquid crystal iris part 325. Under an abnormal situation, in the above mentioned formation, the liquid crystal molecules 331a held between the transparent electrodes 333a and 333b will be as in FIG. 36. That is, the light passes through the entire range of the liquid crystal part 331 and automatically returns to the relative state that the passing light passes through all the respective polarizing plates 327 and 328 in the front and rear and the liquid crystal iris part 325 fully opens. Therefore, even under the above mentioned abnormal situation, the brightness of the observed image can be secured and the danger of becoming unable to observe can be avoided.

Also, in case the same as this occurs on the liquid crystal lens side, the focus position of the liquid crystal lens part 326 will automatically shift to the far focus side. That is, when the lead wires 341 and 342 feeding the driving signals to the transparent electrodes 335a and 335b of the liquid crystal lens part 326 break or the other electricity passing systems break so that no driving signal may be fed to the transparent electrodes 335a and 335b of the liquid crystal lens part 326, the liquid crystal molecules 332a held between the transparent electrodes 335a and 335b will automatically return to the state shown in FIG. 36 and therefore the focus position of the liquid crystal lens part 326 will automatically shift to the far focus side. As the focus position thus shifts to the far focus side, the danger that only the position adjacent to the object 381 can be observed can be avoided, a wide range away from the object 381 can be observed and the safety can be secured.

Even if an abnormal state such that the driving signals can not be fed to the liquid crystal iris part 325 and liquid crystal lens part 326 or reduced signals occur, the state that the observation can be made will be able to be automatically secured, therefore the endoscope 301 as inserted will be able to be recognized and safety will be able to be secured.

Figure 41:
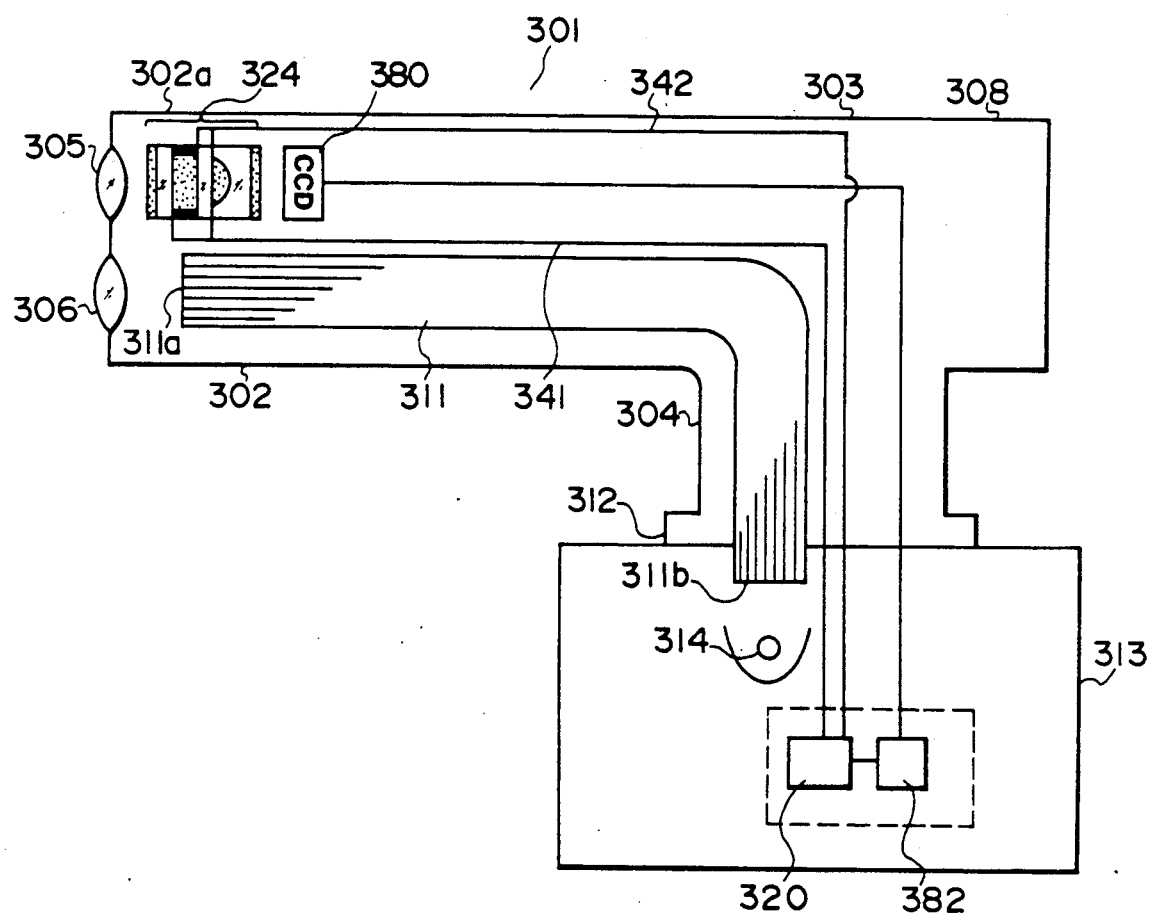

FIG. 41 shows an embodiment different from that shown in FIG. 35. This embodiment is of an electronic endoscope 301 wherein a solid state imaging device 380 consisting of a CCD or the like is set as opposed to an objective lens 305 and the same electric optical device apparatus part as is mentioned above is inserted between the objective lens 305 and solid state imaging device 380 so that the light having formed an image on the imaging surface of the solid state imaging device 380 through the electric optical device apparatus part 324 may be imaged by the solid state imaging device 380 and this imaging signal may be made a video signal by a video signal processing circuit of an image processing apparatus 382 provided within an electric light source apparatus 313. This video signal is transmitted to a monitor (not illustrated) and is made a video image.

On the other hand, the brightness of the observed image is detected by the information in the image processing apparatus 382. For example, its luminance signal is utilized. In this case, the integrated value of the luminance signal of each frame, the integrated value of the luminance signal of 1 frame or the peak value or average value of the luminance signal of 1 field is used. The electric optical device apparatus part 324 is driven the same as is mentioned above by a light amount detecting means provided on this electric light source apparatus 313 side.

The invention is not limited to the embodiments shown in FIGS. 35 to 41. For example, the light amount detecting means may be provided within the endoscope or, for example, in the light path of the observing optical system in the insertable part or hand base operating part or may be incorporated within the electric light source apparatus. Also, the driving circuit may be provided separately from the power source or the like. Further, the electric optical device is not limited to the liquid crystal but may be a PLZT or the like. In the formation shown in FIGS. 35 to 41, even when the signal system transmitting driving signals to the electric optical iris device and electric optical lens device breaks, the driving system fails and the electric optical iris device and electric optical lens device can not normally function, the electric optical iris device will automatically return to the wide caliber side, the focus position of the electric optical lens device will automatically return to the far focus side and therefore a bright wide observing region will be able to be secured. Thus, during the use of the endoscope, even if abnormal situation that driving signals can not be fed to the electric optical iris device and electric optical lens device is produced, the observation will be able to be automatically secured, the operator will be able to recognize the endoscope as inserted and safety will be able to be secured.

On the other hand, usually in response to the output of the light amount detecting means for detecting the amount of the light entering the objective optical system of the endoscope, the electric optical iris device shifts to the small caliber side in response to the light amount level and the electric optical lens device shifts to the near focus side. Thereby, under the quickly varying special observing situation of the endoscope, even when the observed object is approached or separated, the focus will not obscured or darkened, on the contrary, there will be no halation by an excess light amount and an optimum observation will be able to be made with a proper magnification power. This operation is made automatically and the operator need not carry out an adjusting operation. Therefore, in various inspecting operations by using the endoscope, the observing optical system adjusting operation need not be made and therefore the endoscope inspecting operatability improves greatly.

When an electric optical device such as a liquid crystal iris is used, the spectral characteristics of the transmitted light may vary, for example, with the driving voltage.

Figure 42:
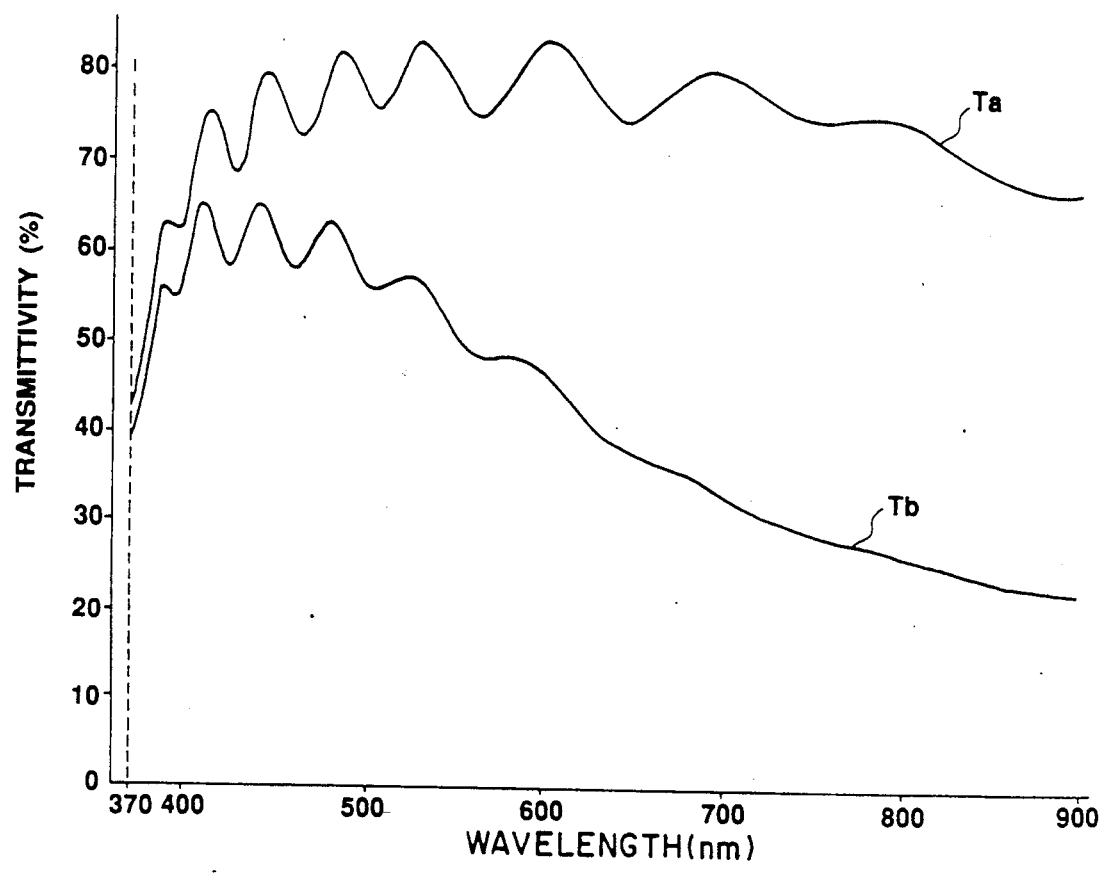
FIG. 42 is a characteristic diagram showing the variations of spectral characteristics when the liquid crystal iris is fully opened and is closed.

FIG. 42 shows transmittivity characteristics Ta in case the liquid crystal iris is fully opened and transmittivity characteristics Tb in case it is throttled.

Thus, in case the spectral characteristics vary with the throttled amount, the formation shown in and after FIG. 43 will be made to prevent or reduce the influence.

Figures 43, 44:
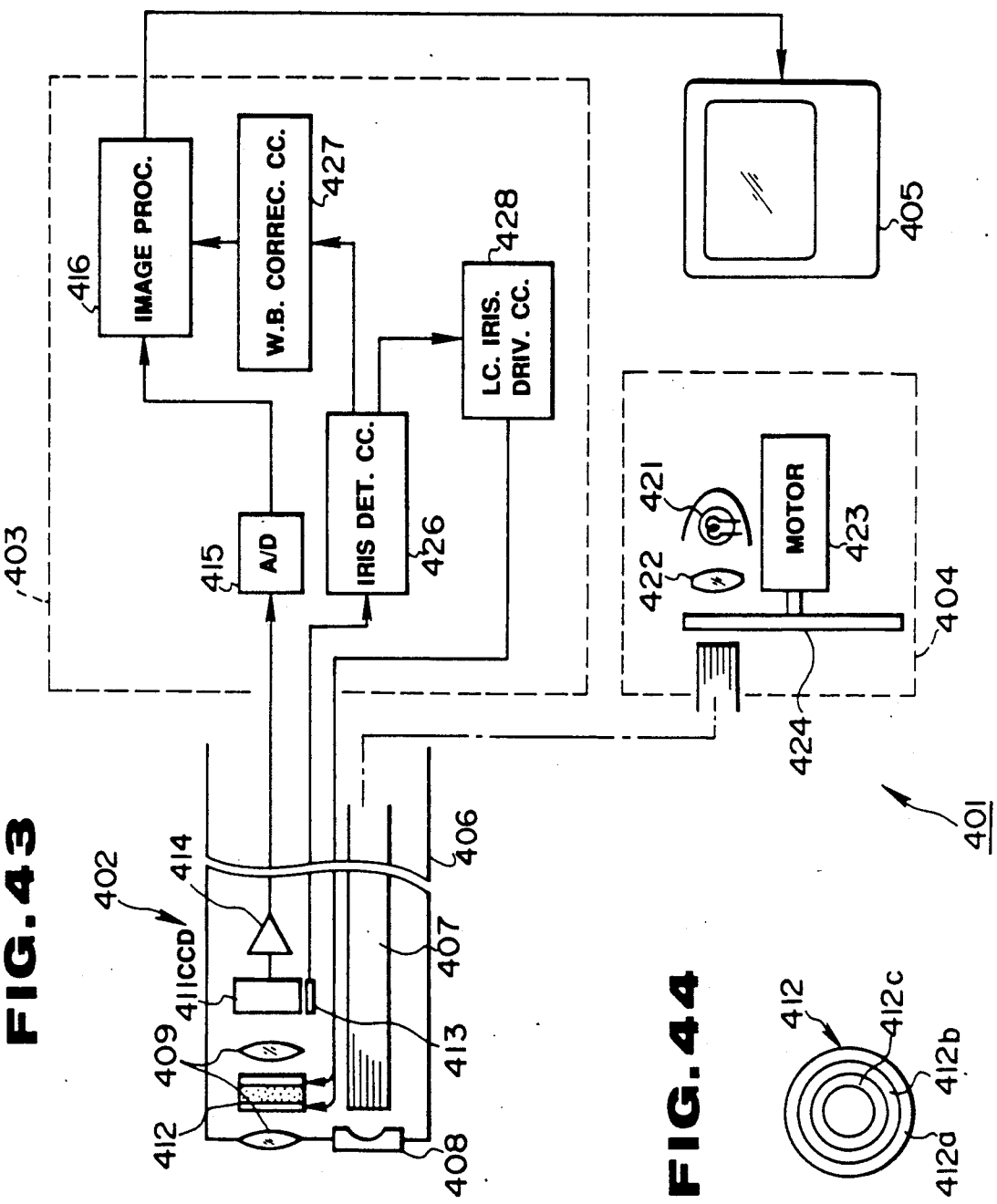
FIGS. 43 to 57 relate to apparatus provided with tone variation preventing functions.

An electronic endoscope apparatus 401 shown in FIG. 43 comprises an electronic endoscope 402 for observing organs within a body cavity, a signal processing apparatus 403 for processing signals of this electronic endoscope 402, a light source apparatus 404 for feeding an illuminating light to the above mentioned endoscope 402 and a color monitor 405 for displaying a video signal output from the above mentioned signal processing apparatus 403.

The above mentioned electronic endoscope 402 has an elongate insertable part 406 through which a light guide 407 for transmitting an illuminating light is inserted so that, when a connector (not illustrated) of this light guide 407 is connected to a light source apparatus 404, the illuminating light may be fed from the light source apparatus to the entrance end surface of the light guide. The illuminating light transmitted by the light guide 407 is radiated to the object side further through a light distributing lens 408 from the exit end surface. The illluminated object is made to form an image on a CCD 411 arranged in the focal plane by an objective optical system 409 fitted to the tip part of the insertable part 406.

The above mentioned objective optical system 409 is formed of a plurality of lens systems so that the light incident through this objective optical system 409 may be varied in the light amount by a liquid crystal iris 412. As shown in FIG. 44, the above mentioned liquid crystal iris 412 is provided concentrically circularly with a plurality of ring electrodes 412a, 412b, . . . (the innermost peripheral one is a disk) so that the iris diameter may be varied by the applied voltage. In this case, in case the incident light amount is large, the iris diameter will be controlled to be small but, on the contrary, in case the incident light amount is small, the iris diameter will be controlled to be large.

A photosensor 413 for measuring the light amount entering the CCD 411 is provided adjacently to the CCD 413.

The signal charge photoelectrically converted by the above mentioned CCD 411 is read out by the application of a CCD driving signal from a CCD driving circuit (not illustrated), is input into an A/D converter 415 within the signal processing apparatus 403 through a buffer 414 and is converted to a digital signal which is then input into an image processing circuit 416 and is processed to produce a video signal of a predetermined system, for example, a composite video signal of an NTSC which is color-displayed on a color monitor 405.

The light source apparatus 404 for feeding an illuminating light to the above mentioned light guide 407 comprises a lamp 421 emitting a white color light, a condenser lens 422 interposed in the light path of the white color light of this lamp 421 and condensing the light and a rotary color filter 424 rotated by a motor 423. This rotary color filter 424 is fitted with filters transmitting light of respective wavelength ranges of red, green and blue so that, when it is rotated by the motor 423, the filters may be sequentially interposed in the light path connecting the condenser lens 422 and the entrance end surface of the light guide 407 and the illuminating lights of red, green and blue may be radiated to the entrance end surface of the light guide 407.

The signal measured by the above mentioned photosensor 413 is input into an iris value determining circuit 426 within the signal processing apparatus 403, a color correcting signal is output in a white balance correcting circuit 427 in response to the photoelectrically converting signal level and an iris value determining signal determining an iris value making a light amount desirable for the observation is output to a liquid crystal iris driving circuit 428.

The above mentioned liquid crystal iris driving circuit 428 applies a liquid crystal iris driving voltage to the electrodes of the liquid crystal iris 412 so as to throttle the light amount transmitted through the entire liquid crystal iris 412 in response to the above mentioned iris value determining signal.

Also, the above mentioned white balance correcting circuit 427 controls the gain of the color signal level when processing the signal in the image processing circuit 416 by the color correcting signal output from the iris value determining circuit 426 so that, even in case the transmittivity (iris value) of the liquid crystal iris 412 varies, the spectral transmittivity variation by the variation of the iris value may be corrected.

The operation of the thus formed apparatus 401 shall be explained in the following.

The light emitted from the lamp 421 is radiated to the object through the light distributing lens 408 fitted to the illuminating window as an illuminating light through the condenser lens 422, rotary color filter 424 and light guide 407, is reflected by the object and is incident upon the CCD 411 through the objective optical system 409 and liquid crystal iris 412. The light, that is, the object image incident upon the CCD 411 is photoelectrically converted and is output to the buffer 414. The signal amplified by the buffer 414 is input into the A/D converter 415 and is converted to a digital signal which is input into the image processing circuit 416.

On the other hand, a part of the light from the object is incident upon the photosensor 413, is photoelectrically converted by this photosensor 413 and is output to the iris value determining circuit 426 which receives this output, calculates an iris value causing no halation, blooming and smearing and giving a light amount desirable for the observation outputs this signal to the liquid crystal iris driving circuit 428 and white balance correcting circuit 427. The liquid crystal iris driving circuit 428 having received the signal from the iris value determining circuit 426 applies to the liquid crystal iris 412 a voltage that the liquid crystal iris 412 at the tip of the endoscope may be of the iris value determined by the iris value determining circuit 426. The liquid crystal iris 412 to which this voltage has been applied varies to be of an iris diameter that the light amount corresponding to this voltage and incident upon the CCD 411 may be an optimum amount. As the spectral transmittive characteristics vary with the iris diameter of the liquid crystal iris 412 as described above, the white balance correcting circuit 427 having received the signal from the iris value determining circuit 426 makes a correction in response to the characteristics and outputs to the image processing circuit 416 a correcting signal which reproduces an optimum color.

The image processing circuit 416 receives the signal from the CCD 411 through the A/D converter 415 and the signal from the white balance correcting circuit 427, processes the image signal and outputs it to the color monitor 405. Therefore, on the color monitor 405, the brightness and tone are corrected to have no halation, blooming and smearing, the tone does not vary with the iris value and an optimum object image can be reproduced. Also, in case the light amount is in excess, the throttling will be larger, therefore the photographed field depth will be deeper and a clear image with a wide focused range will be obtained.

Figure 45:
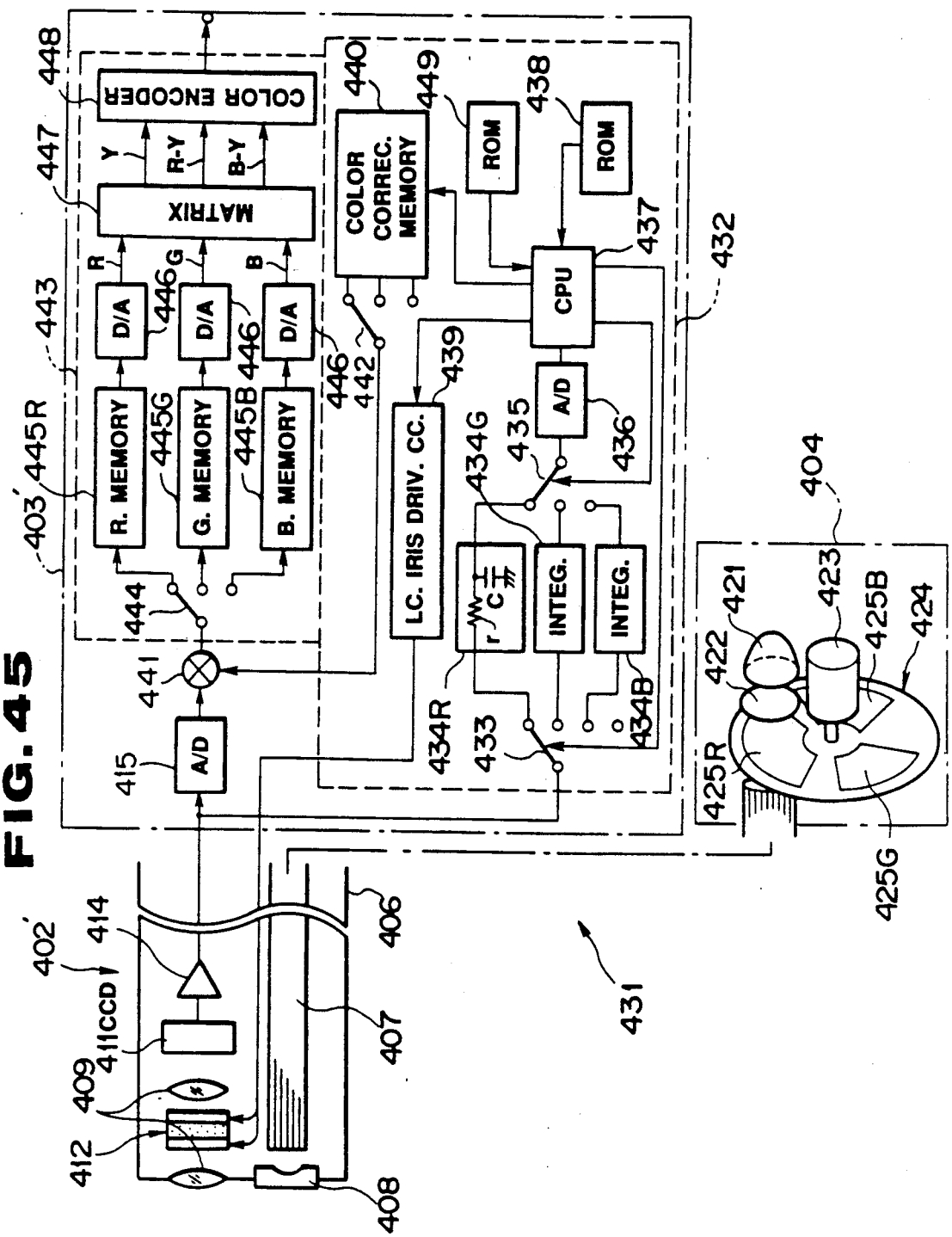

FIG. 45 shows an electronic endoscope apparatus 431 different from that in FIG. 43.

In this apparatus 431, an electronic endoscope 402' provided with no photosensor 413 is used in the electronic endoscope 402 shown in FIG. 43. A signal processing apparatus 403' is formed as follows.

A signal having passed through a buffer 414 is input into an A/D converter 415 and is input into integrating circuits 434R, 434G and 434B through a multiplexer 433 forming an iris controlling and color correction controlling circuit 432. Each of the integrating circuits 434R, 434G and 434B is formed, for example, of a resistance r and capacitor C and the integrated signal is input into a CPU 437 through a multiplexer 435 and A/D converter 436.

The above mentioned multiplexer 433 is controlled in switching, for example, by a CPU 437 and the signals imaged under the respective illuminations of red, green and blue and with the liquid crystal iris 412 opened (maximum transmitted light amount) are integrated by respective integrating circuits 434R, 434G and 434B.

These integrated signals R, G and B are taken into the CPU 437 and the degree of the light amount control or, in other words, the degree of the iris value from these levels is operated and determined. Then, in setting at this iris value, the applied voltage data of the size of the voltage value to be applied to the liquid crystal iris 412 are read out of an ROM 438 into which the relation between the iris value and the voltage value applied to the liquid crystal is stored in advance and are output to a liquid crystal iris driving circuit 439. A 2-valued voltage, that is, a voltage in which the liquid crystal of the electrode part is in a maximum transmitted light amount state or light intercepting state (minimum transmitted light amount state) is applied to the respective ring electrodes 412a, ... so that the iris diameter may be substantially varied.

The data for compensating the spectral transmittivity characteristics by the iris value of the liquid crystal iris 412 are also stored into the above mentioned ROM 438 so that, in case the liquid crystal iris 412 is set at an optimum iris value by the designation of the iris value determined by the operation by the above mentioned CPU 437 and the average value level of the integrating circuits 434R, 434G and 434B, the data for compensating the lag of the white balance caused by the transmittivity dependence for the R, G and B color signals may be read out and may be stored into a color correcting memory 440.

The signal having passed through the above mentioned A/D converter 415 is input into a multiplier 441, is multiplied by color correcting data for R, G and B read out through a multiplexer 442 from a color correcting memory 440, is adjusted in the white balance and is then input into an image processing circuit 443. In this image processing circuit 443, the signal having passed through the multiplier 441 is written into (frame) memories 445R, 445G and 445B respectively for R, G and B through a multiplexer 444. The signal data written into these memories 445R, 445G and 445B are simultaneously read out, are converted to analogue color signals R, G and B respectively through D/A converters 446 and are then input into a matrix circuit 447, a luminance signal y and color difference signals R-y and B-y are produced and further a composite video signal is Produced through a color encoder 448 and is color-displayed on a color monitor (not illustrated).

The above mentioned light source apparatus 404 is of the same formation as is shown in FIG. 43 (in which color transmitting filters 425R, 425G and 425B which are fan-shaped and transmit respectively red, green and blue are shown as fitted to the rotary color filter 424).

In case the liquid crystal iris 412 is set at the maximum transmittivity and yet the transmittivity shows the wavelength dependence, it will be corrected by writing the correcting data into an ROM 449. In case the liquid crystal iris 412 is set as opened, for example, under a white object, the wavelength dependence will be able to be known by whether the output signals of integrating circuits 434R, 434G and 434B are white-balanced or not. Also, from the outputs of the integrating circuits 434R, 434G and 434B in case the iris value is varied under the white object, the wavelength dependence shown by the iris value can be known. In order to make a white balance from these data, the size of the factor to be multiplied for the respective color signals R, G and B is stored into the color correcting memory 440.

In the multiplexers 444 and 442, each color frame is switched by a timing generator (not illustrated) synchronized with the rotation of the rotary color filter 424.

The operation and effect of this apparatus 431 are substantially the same as of the apparatus 401 shown in FIG. 43.

Figure 46:
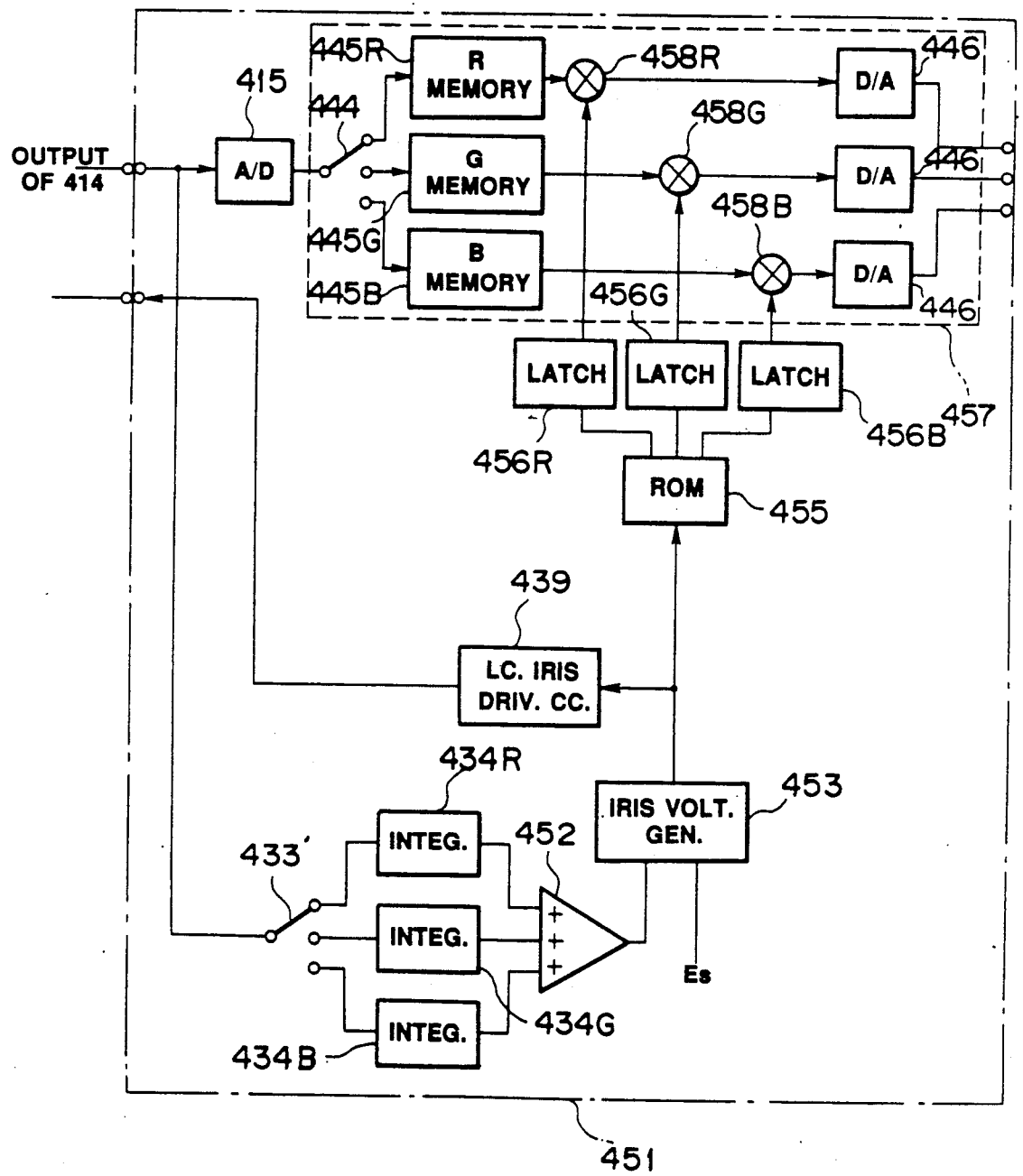

FIG. 46 shows an essential part of a modification of FIG. 45. This modification is a signal processing apparatus 451 of a formation somewhat different from that of the signal processing apparatus 403' shown in FIG. 45.

The output of integrating circuits 434R, 434G and 434B is input into an iris voltage generating circuit 453 through an adder 452. This generating circuit 453 outputs to a liquid crystal iris driving circuit 439 an iris voltage for increasing and decreasing the iris value so as to be of a standard level $E_s$ as compared with the standard level $E_s$. Also, the output of this generating circuit 453 is input into an ROM 455 and color correcting data at the iris value by this liquid crystal iris are read out and are latched in latches 456R, 456G and 456b.

The color correcting data for the R, G and B signals latched by the above mentioned respective latches 456R, 456G and 456B are input respectively into multipliers 458R, 458G and 458B in an image processing circuit 457 and are multiplied by digital color signals read out respectively of memories 445R, 445G and 445B respectively for R, G and B so as to be white-balanced. These white-balanced signals are converted to analogue color signals R, G and B respectively through D/A converters 446 and are output to the monitor side from R, G and B output ends.

A multiplexer 433' into which the output of a buffer 414 is input is switched as synchronized with the respective color frames by a timing generator (not illustrated).

Figure 47:
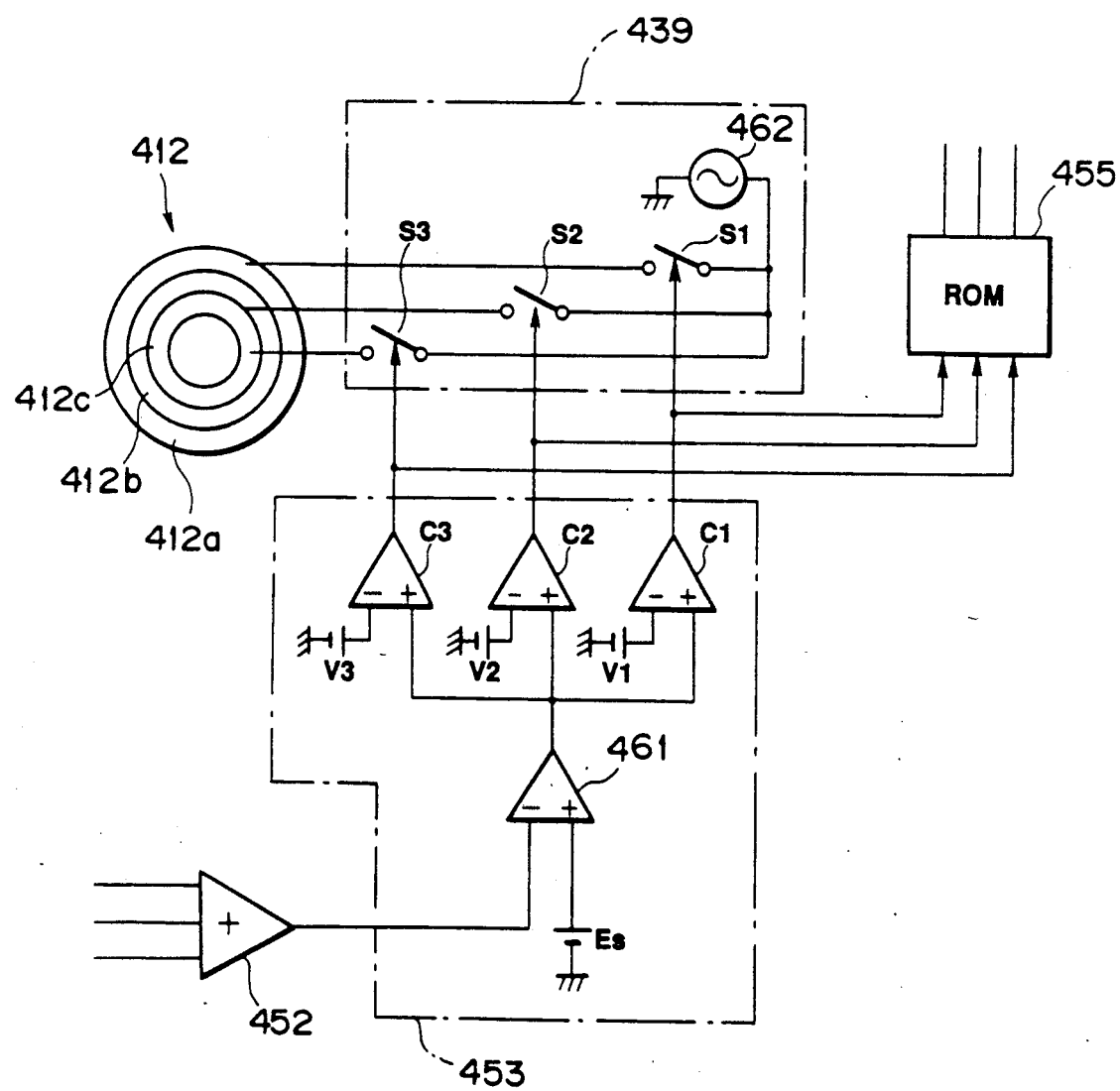

The formation of the above mentioned iris voltage generating circuit 453 and iris driving circuit 439 is shown in FIG. 47.

The output signal of an adder 452 is input into a differential amplifier 461 and a difference signal from a standard level $E_s$ is output, is input into comparators $C_1$, $C_2$ and $C_3$ and is compared respectively with standard voltages $V_1$, $V_2$ and $V_3$. The standard voltages $V_1$, $V_2$ and $V_3$ are set to be $V_1 < V_2 < V_3$. The switches $S_1$, $S_2$ and $S_3$ of a liquid crystal iris driving circuit 439 are controlled to be on/off by the outputs of the comparators $C_1$, $C_2$ and $C_3$.

In this example, in case the output level of the adder 452 is somewhat larger than the standard level, for example, only the output of the comparator $C_1$ will be "H", the driving signal of a driving signal generator 462 will be applied to an electrode 412a on the outermost periphery of the liquid crystal iris 412 by switching on the switch $S_1$ and the liquid crystal part opposed to this electrode 412a will be in a light intercepting state.

In case the level of the output signal of the adder 452 is larger, the output of the comparator C, will be also "H". Thus, the throttling of the liquid crystal iris 412 is controlled.

The outputs of the above mentioned comparators $C_1$, $C_2$ and $C_3$ are input into an ROM 455 and color correcting data are read out with the outputs corresponding to the throttled states of the liquid crystal iris 412 to correct colors.

The operation and effect of this apparatus 451 are substantially the same as in FIG. 43.

Figure 48:
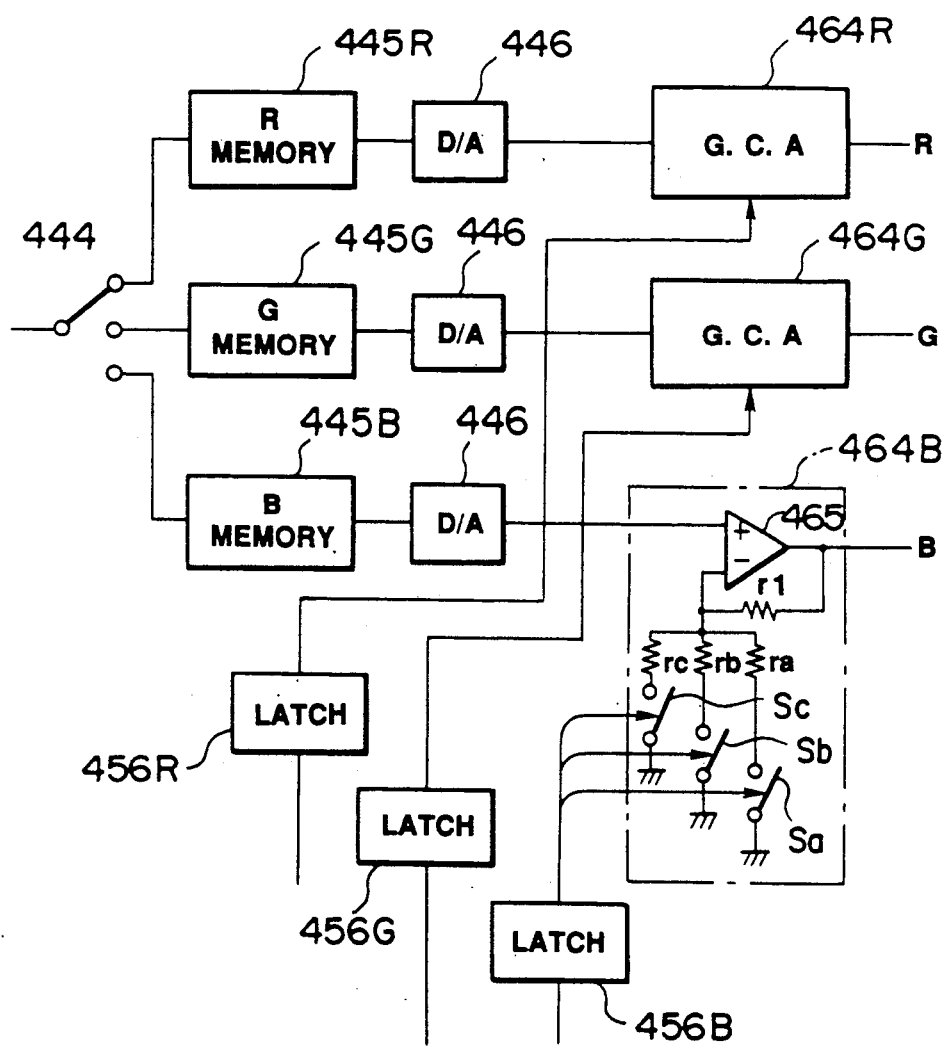

In the apparatus 451 in FIG. 46, the outputs of the latches 456R, 456G and 456B are multiplied by digital color signals to correct colors but, as shown in FIG. 48, the gains of gain controlling amplifiers 464R, 464G and 464B may be controlled.

The gain controlling amplifier (for example, 464B) comprises an operational amplifier (abbreviated as the OP amplifier hereinafter) 465, a resistance $r_1$ provided between the input terminal and output terminal of the OP amplifier, resistances ra, rb and rc varying the gain and switches Sa, Sb and Sc.

For example, the larger the output of the latch 456B, with the switches Sa, Sb and Sc off, the smaller the gain to correct colors.

Figure 49:
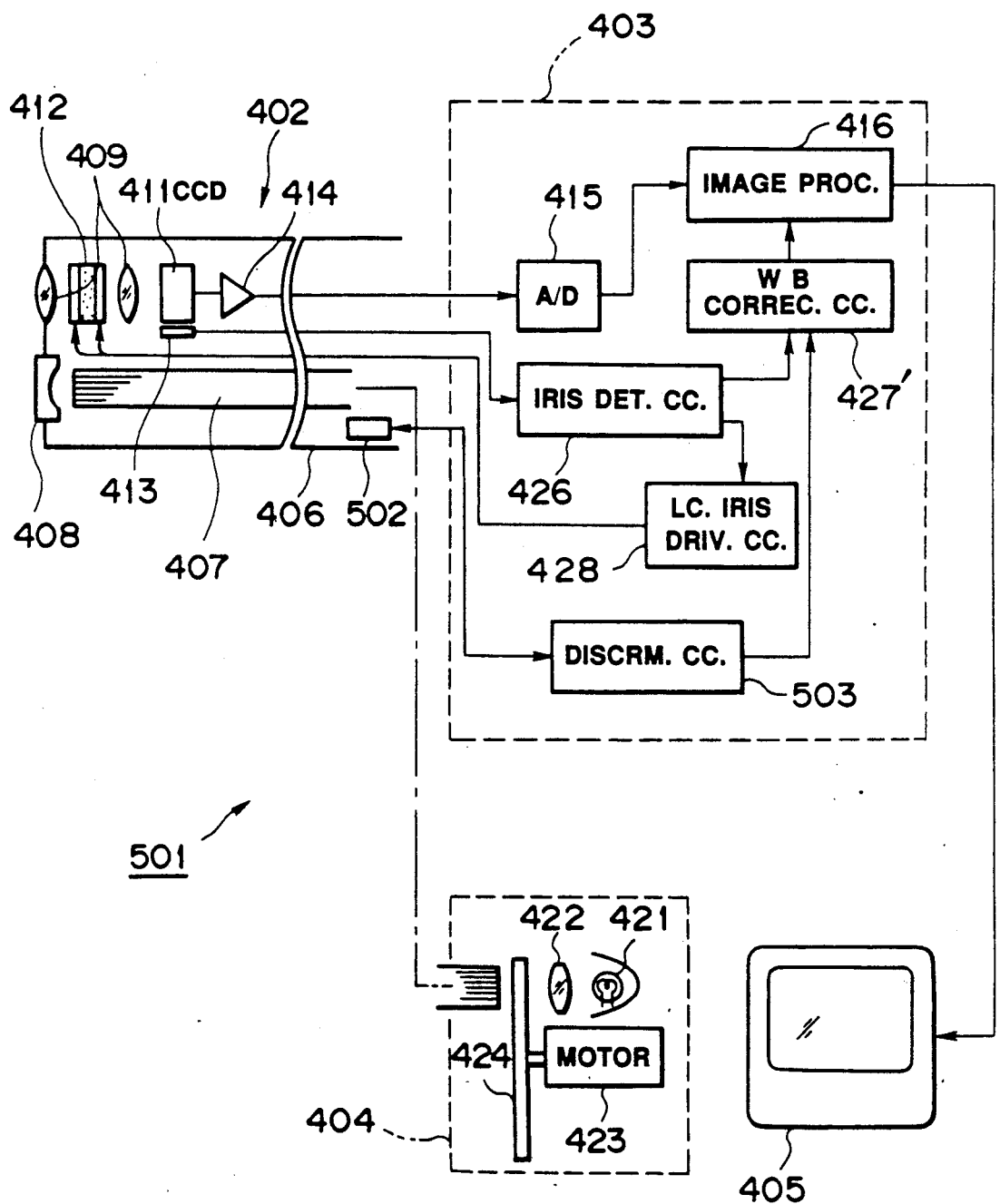

Generally, the spectral characteristics vary with the kind of the endoscope, that is, the objective optical system or imaging means. Therefore, in order to make an optimum correction in response to the kind of the endoscope to be used, a formation as is shown in FIG. 49 may be made.

In this apparatus 501, in the apparatus 401 shown in FIG. 43, the electronic endoscope 402 is provided with a kind signal generating means 502 corresponding to the kind. This kind of endoscope signal generating means 502 can be formed, for example, of a resistance of a resistance value corresponding to the kind, is built-in, for example, in a connector and is connected to a signal processing apparatus 403 so that the resistance value may be detected by a discriminating circuit 503 provided within the signal processing apparatus 403, the kind may be thereby discriminated and this discriminating signal may be output to a white balance correcting circuit 427'.

This white balance correcting circuit 427' is provided with a white balance correcting circuit for all kinds so that a white balance correcting signal of a kind determined by a discriminating signal may be output and a white balance correction adapted to the kind may be made.

The others are of the same formation as of the apparatus 401 shown in FIG. 43. The kind signal generating means may be formed not only of a resistance but also of a capacitor, coil or whether short-circuited or not. Also, the endoscope may be provided with bar codes so that the codes may be read out by licensers. The endoscope may have an ROM representing the kind built-in so that the contents of the ROM may be read out by the signal processing apparatus and the white balance correcting amount may be varied in response to the signal read out.

Figure 50:
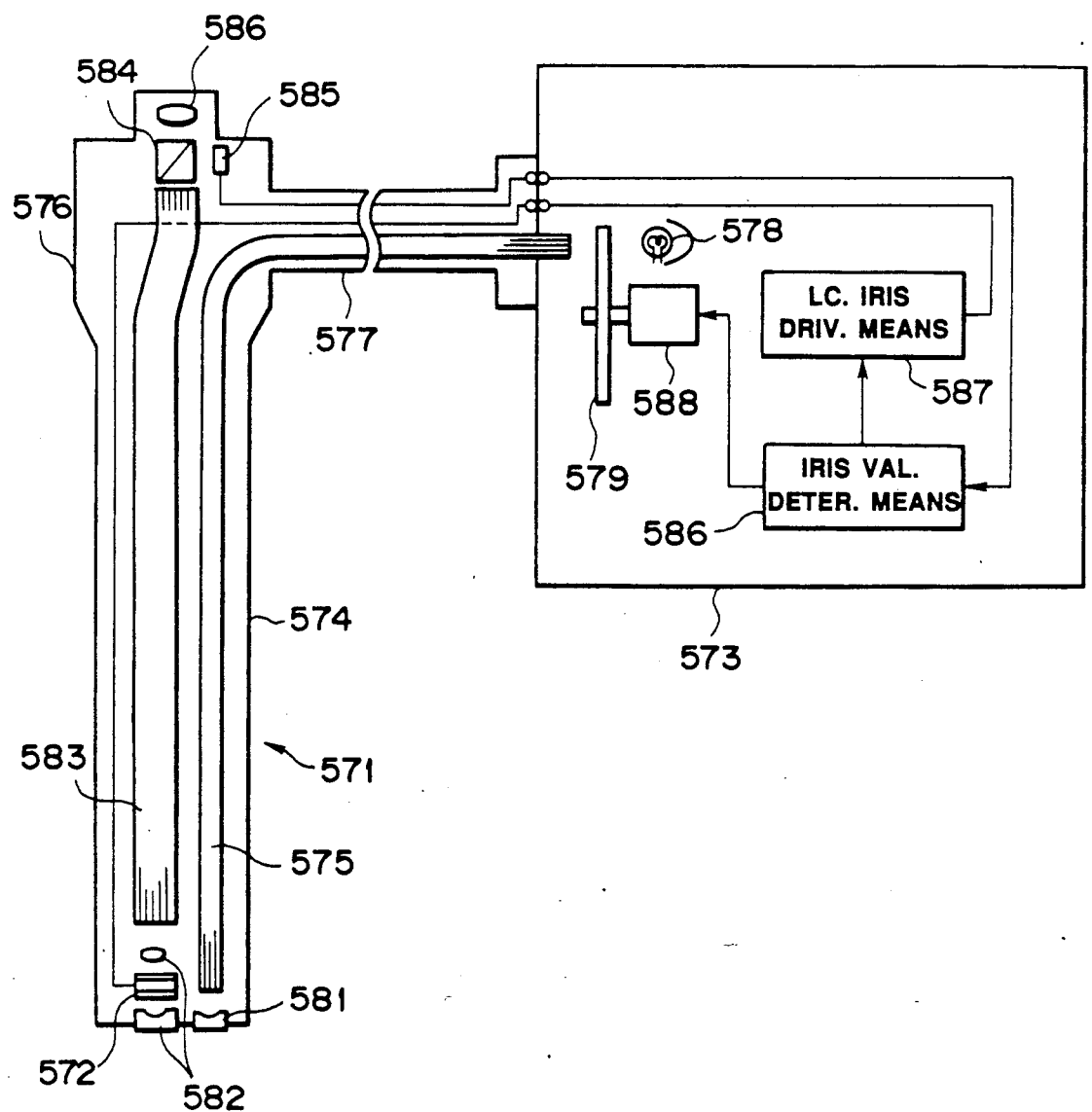

As shown in FIG. 50, in case a liquid crystal iris 572 is used in an optical endoscope 571, a white balance will be able to be made in a light source apparatus 573.

The optical endoscope 571 has an elongate insertable part 574 through which a light guide 575 is inserted. This light guide 575 is further inserted through a light guide cable 577 extended out of an operating part 576 and can be connected to a light source apparatus 573. A white color light of a light source lamp 578 of this light source apparatus 573 is radiated to the entrance end surface of the light guide 575 through a color correcting filter 579 and this radiated illuminating light is transmitted to the exit end surface side and is emitted to the object side through a light distributing lens 581 fitted to an illuminating window from the exit end surface. The illuminated object image is formed on the entrance end surface of an image guide 583 through an objective optical system 582 and liquid crystal iris 572 and is transmitted to the exit end surface side of this image guide 583. A light branching prism 584 is arranged as opposed to this exit end surface so that a part of the light may be reflected and may be led to a light measuring means 585 and the rest may be led to an eyepiece lens 586. The output of this light measuring means 585 is input into an iris value determining means 586 within the light source apparatus 573. This iris value determining means 586 determines an iris value adapting the liquid crystal iris 572 to observation by the output of the light measuring means 585 and outputs a signal therefor to a liquid crystal iris driving means 587. The liquid crystal iris 572 is set at an iris value adapted to observation by the output voltage output from this liquid crystal iris driving means. Also, the above mentioned iris value determining means 586 outputs to a color correcting filter driving means 588 a signal for dissolving the spectral transmittive characteristics of the liquid crystal iris 572 in case it is set at an iris value adapted to observation. By this signal, for example, the rotation angle of the color correcting filter 579 is varied, the position of the color correcting filter 579 interposed in the light path connecting the lamp 578 and the entrance end of the light guide 575 is variably controlled, the spectral transmittivity of the color correcting filter in that position is varied, the spectral transmittive characteristics of the liquid crystal iris 572 are compensated and the liquid crystal iris 572 is set at a fixed transmittivity having no wavelength dependence.

In case the liquid crystal iris 572 shows such spectral transmittive characteristics as well transmit, for example, a blue color component, a filter of a characteristic of reducing a color of a blue series, that is, of a yellow series will be used as a color correcting filter.

FIG. 50 is a formation and operation as are mentioned above. Thus, the tone variation with the variation of the iris value of the liquid crystal iris 542 can be prevented.

For example, in the apparatus 431 in FIG. 45, by varying the voltage applied to the liquid crystal iris 412 for each color frame, the spectral transmittivity can be controlled to be a transmittivity having no wavelength dependence.

The present invention can be applied not only to the frame sequential type electronic endoscope apparatus but also to the case of using an imaging means having a color filter built-in Also, the present invention can be applied not only to the electronic endoscope provided with an imaging means on the tip side of the insertable part but also to the optical type endoscope fitted with a TV camera in the eyepiece part.

It can be applied not only to the case of using a liquid crystal iris but also to the case of utilizing such other physical optical devices which the phototransmittivity varies with the size of the electric field or magnetic field as, for example, a catheter, transparent strong dielectric body (for example, a PLZT), Faraday device or electrochromic device utilizing a double refractive phenomenon.

Figure 51:
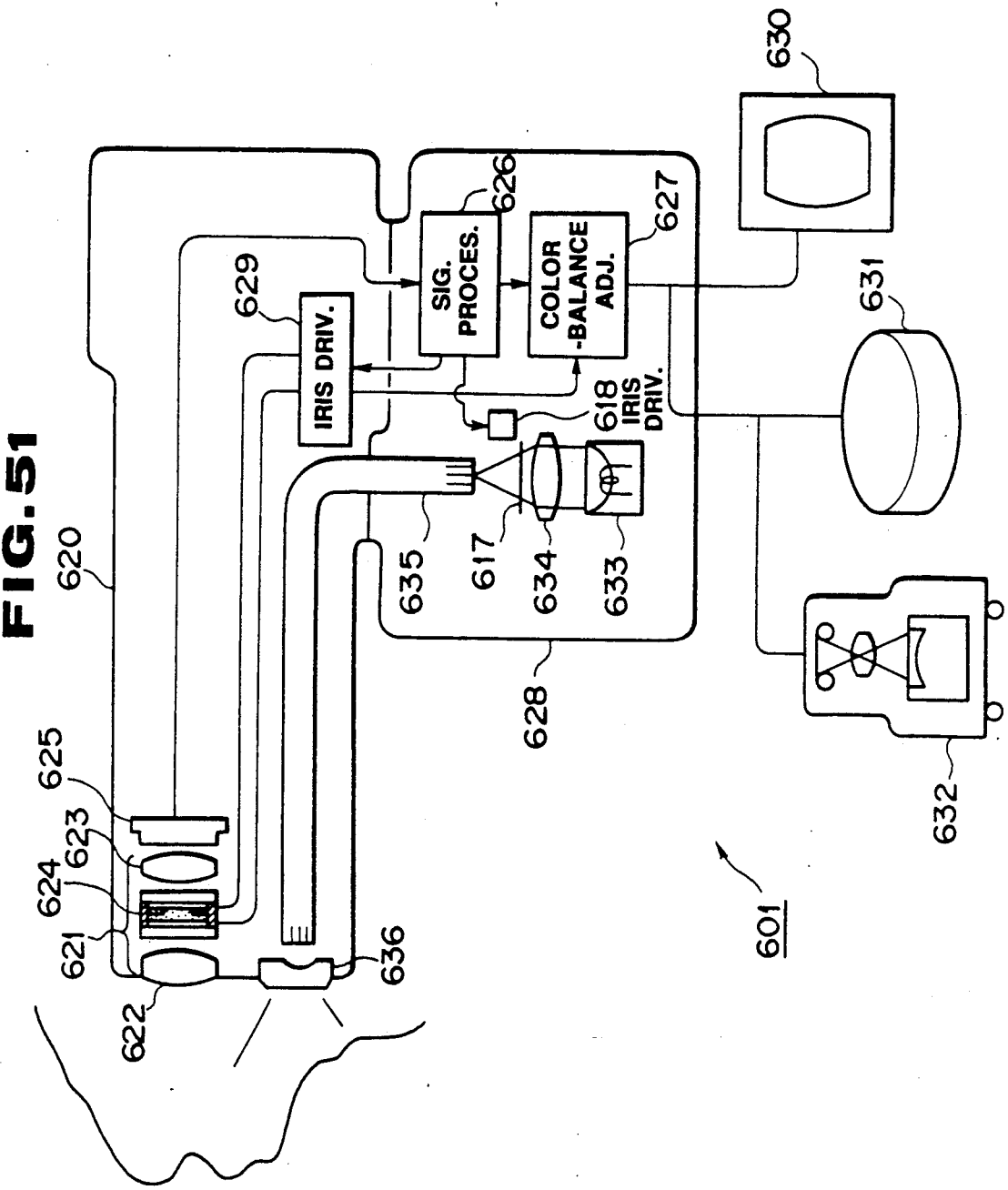

An endoscope apparatus 601 using, for example, an electrochromic device for the iris is shown in FIG. 51.

In the endoscope apparatus 601 in FIG. 51, a color imaging apparatus using an electrochromic iris is applied to an electronic endoscope. The reference numeral 621 represents an objective lens consisting of two positive lenses 622 and 623 between which an electrochromic iris 624 is placed. A solid state imaging device 625 is arranged on the image forming surface of the objective lens 621. The reference numeral 626 represents a signal processing circuit receiving an output signal from a solid state imaging device 625, forming an image signal and detecting the brightness of the image, 627 represents a color balance adjusting circuit correcting the image signal from the signal processing circuit 626 on the basis of the signal from a later described iris driving circuit and adjusting the color balance and these are arranged within a control unit 628. The reference numeral 629 represents an iris driving circuit arranged within an endoscope body 620, receiving an object brightness controlling signal from the signal processing circuit 626, adjusting the opening of the electrochromic iris 624 and outputting a color compensating signal to a color balance adjusting circuit 627. The above mentioned members form a color imaging apparatus.

The reference numeral 630 represents a television monitor receiving and video-displaying the signal from the color balance adjusting circuit 627, 631 represents an image filing apparatus receiving the signal from the color balance adjusting circuit 627 and recording the television image and 632 represents a photographing apparatus receiving the signal also from the color balance adjusting circuit 627 and photographing the television image on a film. They form an observing and recording system.

The reference numerals 633 and 634 represent respectively a light source lamp and a condenser lens, 635 represents a light guide fiber bundle leading the light condensed by a condenser lens 634 to the tip part of the endoscope body 620, 636 represents an illuminating lens expanding the light emitted from the light guide fiber bundle 635 and radiating it to the object, 617 represents a light source iris arranged between the condenser lens 634 and the entrance end of the light guide fiber bundle 635 and 618 represents a light source iris driving circuit receiving the light source brightness controlling signal from the signal processing circuit 626 and adjusting the opening of the light source iris 617. These form an illuminating system.

Figure 52:
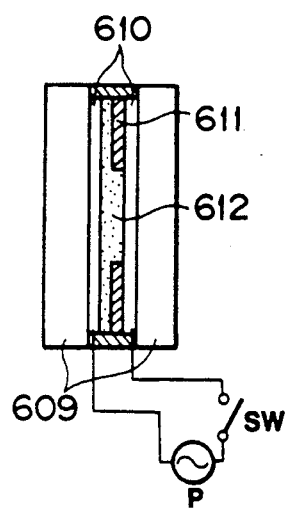

The formation of the above mentioned electrochromic iris 624 is shown in FIG. 52. Two transparent substrates 609 each having a transparent electrode 610 formed on the surface as glass plates are prepared. A ring-like electrochromic layer 611 made of an electrochromic substance is formed- on one of them. These two plates are opposed to each other to form a minute air gap in which an electrolyte 612 is enclosed to form the electrochromic iris 624. When the switch SW is on, by the movement (oxidation-reduction) of the electrons between the electrochromic layer 611 and electrolyte 612, the ring-like part will be colored and the transmittivity will greatly reduce but, when the switch SW is off, the original state will return.

The operation of this apparatus shall be explained in the following. The light incident from the object into the objective lens 621 is made to form an image on the solid state imaging device 625 by the objective lens 621 while passing through the electrochromic iris 624. The output signal from the solid state imaging device 625 is converted to an image signal by the signal processing circuit 626, is adjusted by the color balancing circuit 627 and is then input into the television monitor 630 and the object image is displayed on the television monitor 630. At the same time, the output signal from the color balance adjusting circuit 627 is input also into the image filing apparatus 631 and photographing apparatus 632 to respectively record and photograph the object image.

The output signal from the solid state imaging device 625 is input into the signal processing circuit 626 and the brightness of the object is detected here. If the brightness is too bright, an object brightness controlling signal will be issued from the signal processing circuit 626, the iris driving circuit will receive this signal and will throttle the electrochromic iris 624 and the tone of the transmitted light through the electrochromic iris 624 will vary. However, simultaneously with throttling the electrochromic iris 624, a color correcting signal will be input into the color balance adjusting circuit 627 from the iris driving circuit 629, therefore the color balance adjusting circuit 627 will correct the image signal and, as a result, an image of the same tone as before throttling the electrochromic iris 624 will be displayed in the television monitor 630.

Figure 53:
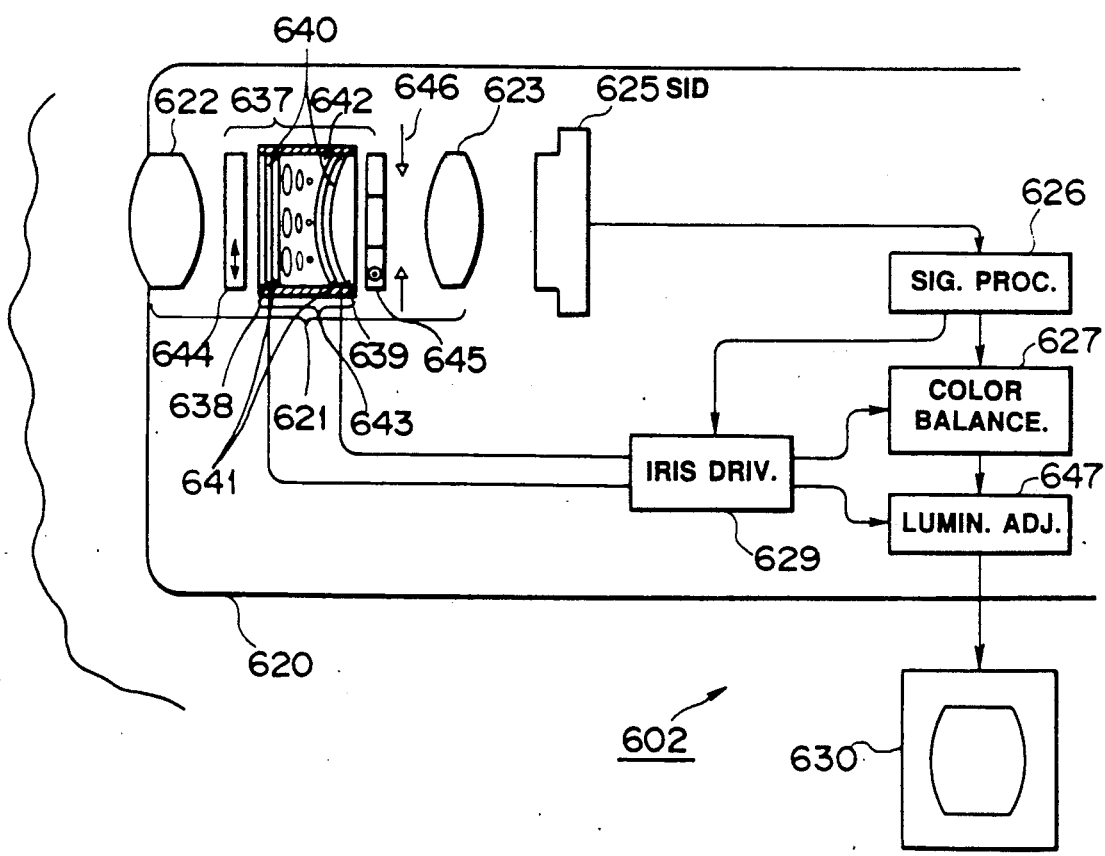

When the light amount is too bright even if the electrochromic iris 624 is most throttled, a light source brightness controlling signal will be issued from the signal processing circuit 626, the light source iris driving circuit 618 will receive this signal and will throttle the light source iris 617 and therefore an image of a proper brightness will be obtained In an endoscope apparatus 602 in FIG. 53, a color imaging apparatus using a liquid crystal iris combined liquid crystal lens is applied to an electronic endoscope.

Figure 54:
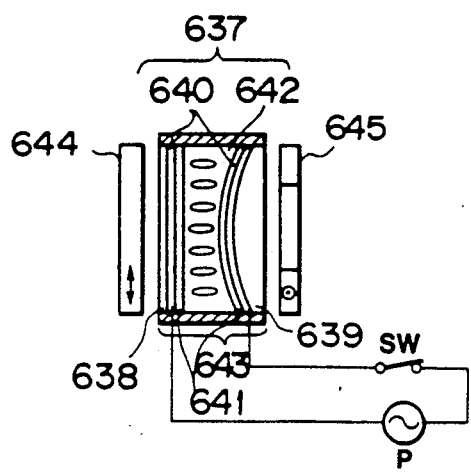

The reference numeral 637 represents a liquid crystal iris combined liquid crystal lens arranged between positive lenses 622 and 623 forming an objective lens 622. Therein, transparent electrodes 640 and orienting membranes 641 twisted by 90 degrees in the orienting direction are applied to coat respectively the surfaces opposed to each other of a transparent substrate 638 and positive lens 639, a nematic liquid crystal 642 is enclosed within a concave lens-like hollow chamber formed by these opposed surfaces to form a twisted nematic (TN) liquid crystal cell 643 and this liquid crystal cell 643 is held by two polarizing plates 644 and 645 which intersect at right angles in the polarizing direction and at least one of which is formed like a ring. When no voltage is applied to the transparent electrodes 641, as the molecule arrangement of the liquid crystal 642 is a twisted nematic arrangement as shown in FIG. 53, the linear polarized light having entered the TN liquid crystal cell through the polarizing plate 644 will be able to pass through the polarizing plate 645 with the polarizing plane rotated by 90 degrees by the TN liquid crystal cell 643 and, as a result, the opening of the iris will become large. Also, as the major axis direction of the molecules of the liquid crystal 642 coincides with the oscillating direction of the linear polarization, the liquid crystal cell 643 will act as a strong concave lens, as a result, the focal distance of the liquid crystal lens 637 will become long and the optical system as a whole will be focused at a far focus. On the other hand, when a voltage is applied to the transparent electrodes 641, as the molecule arrangement of the liquid crystal 642 will become a homeotropic arrangement as shown in FIG. 54, the linear polarization having entered the TN liquid crystal cell 643 through the polarizing plate 644 will not have the polarizing plane rotated, will be intercepted by the polarizing plate 645 and, as a result, the iris opening will become small. Also, as the oscillating direction of the linear polarization will intersect at right angles with the major axis direction of the molecules of the liquid crystal 642, the liquid crystal cell 643 will act as a weak concave lens, as a result, the focal distance of the liquid crystal lens 637 will become short and the optical system as a whole will be focused at a near focus.

The reference numeral 646 represents a brightness iris arranged between the liquid crystal lens 637 and a solid state imaging device 625 and 647 represents a luminance adjusting circuit provided between a color balance adjusting circuit 627 and a television monitor 630 and correcting the luminance signal among the image signals from the color balance adjusting circuit 627.

Figure 55:
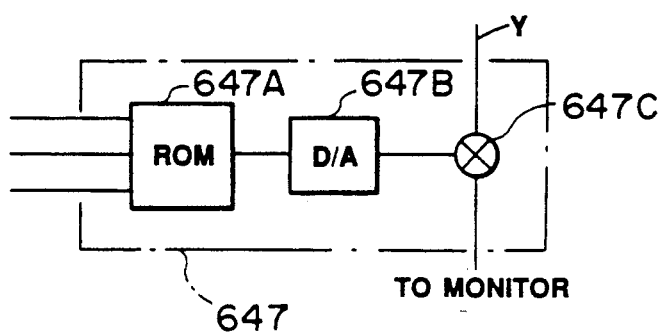

The formation of this luminance adjusting circuit 647 is shown, for example, in FIG. 55. The signal corresponding to the iris amount output from the iris driving circuit 629 is applied to the address end of an ROM 647A having stored the data correcting the luminance unevenness and reads out the correcting data. The data thus read out is converted to an analogue signal by a D/A converter 647B and this analogue signal is multiplied by a composite video signal output through the color balancing circuit 627 in a multiplier 647C. The luminance unevenness is corrected by this multiplication and then the image is displayed in a television monitor 630.

According to this apparatus 602, as the spectral transmittivity of the non-light transmitting part of the liquid crystal iris combined liquid crystal lens 637 varies with the wavelength of the light and varies with the variation of the incident angle of the light, when the iris is throttled in, as compared with that before it is throttled in, the tone vary and a luminance unevenness will be produced but, after the signal from the solid state imaging device 625 passes through the signal processing circuit 626, as the tone is corrected by the color balance adjusting circuit 627 and the luminance unevenness is corrected by the luminance adjusting circuit, an image having the same tone as before the iris is throttled and having no luminance unevenness will be displayed in the television monitor 630.

The iris driving circuit 629 which stores in an internal memory the information of the tone variation and luminance unevenness with the throttling of the liquid crystal iris combined liquid crystal lens 637 may be provided preferably within the endoscope body 620 because the degree of the tone variation and luminance unevenness with the throttling is different depending on the kind of electronic endoscope and the difference in solid state imaging devices. Needless to say, the iris driving circuit 629 may be provided within the control unit or light source apparatus. Also, the formation of the iris driving circuit 629 may be divided into the part of storing the tone variation and luminance unevenness with the throttling and the part of driving the liquid crystal lens 637, the former may be provided within the endoscope body 620 and the latter may be provided within the control unit. The signal processing circuit 626, iris driving circuit 629, color balance adjusting circuit 627 and luminance adjusting circuit 647 may be provided within the endoscope body 620.

In the case of incorporating an auto white balance adjusting function or the into this apparatus 602, the adjustment may be made with the liquid crystal iris combined liquid crystal lens 637 fully opened. Needless to say, the tone variation and luminance unevenness when the iris is fully opened can be corrected by the color balance adjusting circuit 627 and luminance adjusting circuit 647. Also, the produced color shading and luminance shading may be corrected by a color mosaic fitted solid state imaging device.

The illuminating system is omitted in FIG. 53.

Figure 57:
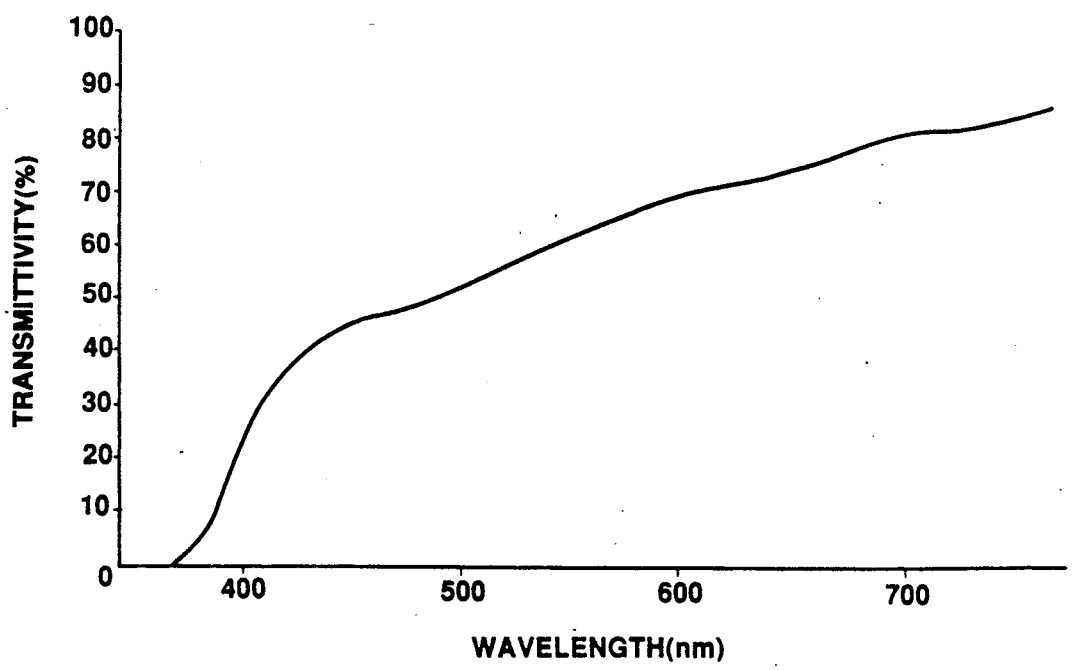
Figure 56:
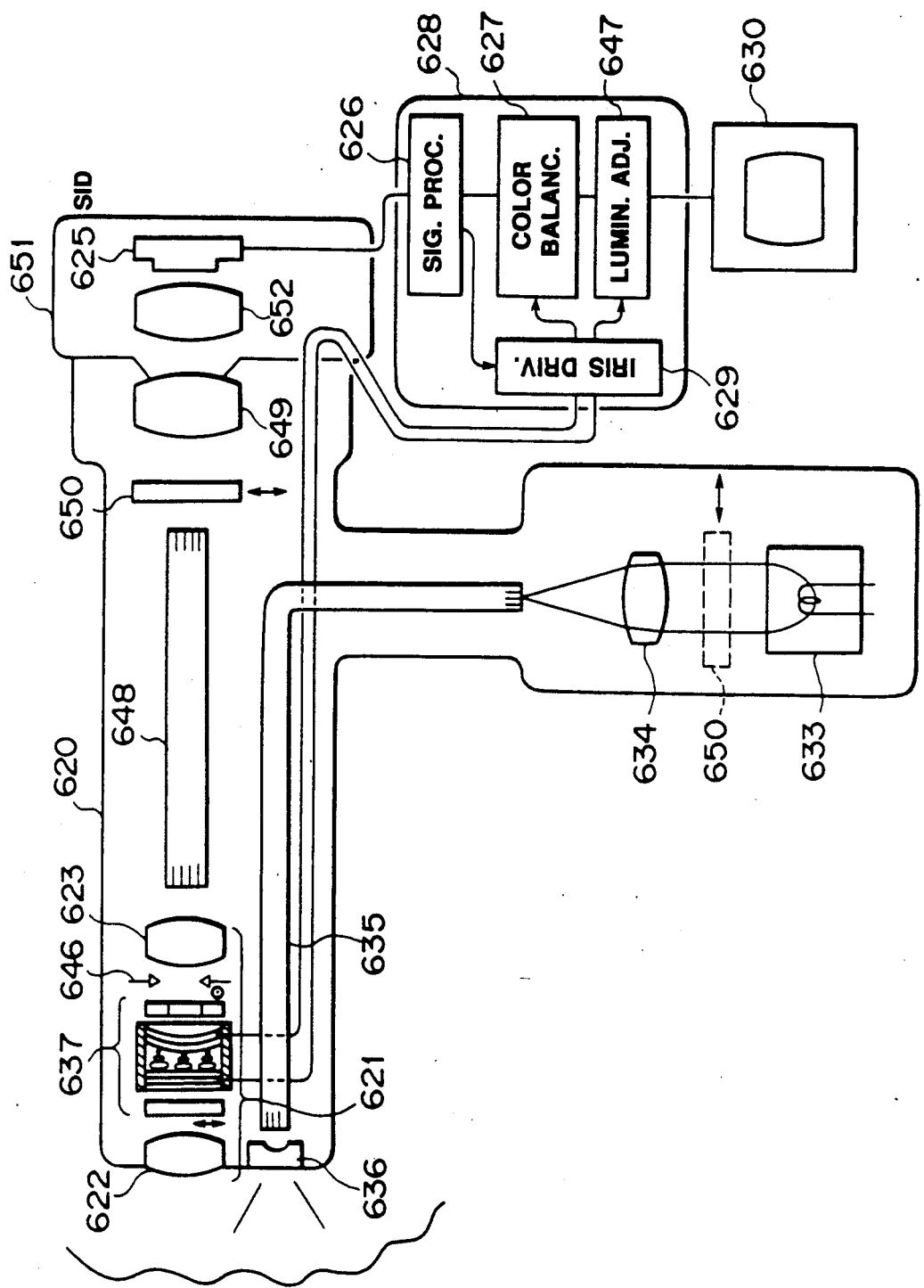

In FIG. 56, a color imaging apparatus using a liquid crystal iris combined liquid crystal lens is applied to a fiber-scope. The same as in the apparatus 602 shown in FIG. 53, a liquid crystal combined liquid crystal lens 637 is arranged between positive lenses 622 and 623 forming an objective lens 621. The reference numeral 648 represents an image guide fiber bundle, 649 represents an eyepiece lens and 650 represents a correcting filter removably arranged between the exit end of the image guide fiber bundle 648 and an eyepiece lens 649 and having a transmittivity characteristic capable of correcting the transmittivity characteristic at the time of throttling, just as in FIG. 42, as shown in FIG. 57. This correcting filter 650 may be removably arranged between a light source lamp 633 and condenser lens 634. The reference numeral 651 represents a television camera removably fitted to the eyepiece part of an endoscope body 620, having an image forming lens 652 arranged within it and having an electric circuit formed the same as in FIG. 53.

As this apparatus is formed as described above, when the television camera 651 is fitted, the object image formed by the objective lens 621 and liquid crystal lens 637 and transmitted by the image guide fiber bundle 648 will be imaged on a solid state imaging device 625 through an image forming lens 652. The output signal from the solid state imaging device 625 is processed the same as in FIG. 53 and the tone variation and luminance unevenness accompanying the throttling of the liquid crystal iris combined liquid crystal lens 637 are corrected.

When the television camera 651 is not used, the observation will be made directly with a naked eye. In such a case, too, the tone variation and luminance unevenness will be produced by the throttling of the liquid crystal iris combined liquid crystal lens 637. Then, if a correcting filter 650 is inserted into the light path, the transmittivity characteristics (See FIG. 42) at the time of throttling the liquid crystal lens 637 will be corrected by the transmittivity characteristic of the correcting filter 650 and therefore the tone variation and luminance unevenness will be corrected.

Even when the television camera 651 is fitted, the output signals may be corrected with the correcting filter 650.

The correcting system using the correcting filter 650 may be used in place of the electric correction in FIGS. 51 and 53 or both of them may be used.

In the apparatus 602 shown in FIG. 53, the luminance adjusting circuit shown in FIG. 55 is provided as a means for dissolving the luminance unevenness but, by providing, for example, three such adjusting circuits as are shown in FIG. 55, the color unevenness can be dissolved.

If the correcting data of the color unevenness as divided into R, G and B for the throttling amounts are stored into, for example, three ROM's and are read out for the correction, the color unevenness will be able to be corrected in each pixel unit. When the correction data of R, G and B are stored into a single ROM, the read out data as divided into R, G and B may be corrected.

A different embodiment can be formed by partly combining the above described respective embodiments.

What is claimed is:
1. An endoscope apparatus comprising:
   an endoscope provided with
      an elongate insertable part,
      a light emitting means for emitting an illuminating light from a tip side of said insertable part,
      an objective optical system arranged on the tip side of said insertable part and forming an optical image of an object to be image,
      a liquid crystal assembly forming at least a part of said objective optical system and formed of a plurality of liquid crystals showing a refractive index anisotropy for an incident light depending on molecule orientation and different response frequencies to driving signals for controlling said molecule orientation, and
      two signal lines inserted through said insertable part and feeding said driving signals to said liquid crystal assembly;
   a signal generating means for selectively outputting said driving signals of at least two frequencies in response to said response frequencies; and
   a control means for varying optical characteristics of said liquid crystal assembly by switching at least a frequency of the driving signals applied to said liquid crystal assembly through said signal lines.
2. An endoscope apparatus according to claim 1 wherein said endoscope is an optical type endoscope in which one front surface of an image guide is arranged on an image forming surface of said objective optical system.

3. An endoscope apparatus according to claim 1 wherein said endoscope is an electronic type endoscope in which a solid state imaging device, provided with a photoelectric converting function, is arranged on an image forming surface of said objective optical system for an object at a fixed distance.

4. An endoscope apparatus according to claim 1 wherein said control means further has an amplitude controlling means for varying an amplitude of said driving signals.

5. An endoscope apparatus according to claim 1 or 4 wherein said liquid crystal assembly has a liquid crystal lens provided with a lens function varying a focal distance by said controlling means.

6. An endoscope apparatus according to claim 1 or 4 wherein said liquid crystal assembly has a liquid crystal iris provided with an iris function varying a light transmitting area by said control means.

7. An endoscope apparatus according to claim 1 or 4 wherein said liquid crystal assembly has a liquid crystal lens and liquid crystal iris formed respectively of liquid crystals with different response frequencies of said molecule orientation.

8. An endoscope apparatus according to claim 3 wherein said liquid crystal lens is formed of a plurality of liquid crystal device lenses enclosing respectively in separate cell liquid crystals with respectively different response frequencies of said molecule orientation.

9. An endoscope apparatus according to claim 6 wherein said liquid crystal iris is formed of a plurality of liquid crystal device irises enclosing respectively in separate cell liquid crystals with respectively different response frequencies of said molecule orientation.

10. An endoscope apparatus according to claim 3 wherein one of said two signal lines is made common with a ground line of said solid state imaging device.

11. An endoscope apparatus according to claim 1 or 4 wherein, in said liquid crystal assembly, a pair of electrodes provided to hold respective liquid crystals are connected in series by lead wires so that said driving signals may be applied as divided.

12. An endoscope apparatus according to claim 1 or 4 wherein, in said liquid crystal assembly, a pair of electrodes provided to hold respective liquid crystals are connected in parallel by lead wires so that said driving signals of a same amplitude may be applied.

13. An endoscope apparatus according to any one of claims 1, 2 or 3 wherein said control means is provided in operating part of said endoscope.

14. An endoscope apparatus according to claim 5 wherein, in said liquid crystal lens, when said driving signals are not applied, the liquid crystal molecules forming said liquid crystal lens will be in a homogeneous arrangement.

15. An endoscope apparatus according to claim 6 wherein, in said liquid crystal iris, when said driving signals are not applied, liquid crystal molecules forming said liquid crystal iris will be in a twisted nematic arrangement.

16. An imaging apparatus comprising:
an image forming optical system for forming an optical image of an object to be imaged;
an image receiving means arranged in a focal plane of said image forming optical system;
a liquid crystal assembly forming at least a part of said image forming optical system, said liquid crystal assembly formed of a plurality of liquid crystals showing a refractive index anisotropy for an incident light depending on molecule orientation and each liquid crystal having a different response frequency to driving signals for controlling said molecule orientation;
two signals lines for feeding said driving signals to said liquid crystal assembly;
a signal generating means for selectively outputting said driving signals different, at least, in frequency to said liquid crystal assembly through said signal lines; and
a control means for varying optical characteristics of said liquid crystal assembly by switching at least the frequency of the driving signals output from said signal generating means.

17. An imaging apparatus according to claim 16 wherein said control means further has an amplitude controlling means for varying amplitude of said driving signals output from said signal generating means. controlling means for varying amplitude of said driving signals output from said signal generating means.

18. An imaging apparatus according to claim 16 wherein said liquid crystal assembly has a liquid crystal lens which can vary the focal distance by said driving signal.

19. An imaging apparatus according to claim 16 wherein said liquid crystal assembly has a liquid crystal iris which can vary a transmitted light amount by said driving signals.

20. An imaging apparatus according to claim 16 wherein said image receiving means is an imaging device having a photoelectric converting function.

* * * * *